(12) United States Patent
Mori et al.

(10) Patent No.: US 12,146,143 B2
(45) Date of Patent: Nov. 19, 2024

(54) METHOD FOR PRODUCING TRANSFORMED PLANT AND TRANSFORMATION AGENT

(71) Applicant: Masashi Mori, Ishikawa (JP)

(72) Inventors: Masashi Mori, Ishikawa (JP); Kanako Nishizawa, Ishikawa (JP); Tomohiro Imamura, Ishikawa (JP); Hiroki Takagi, Ishikawa (JP); Hiroharu Mizukoshi, Ishikawa (JP)

(73) Assignee: Masashi Mori, Ishikawa (JP)

( * ) Notice: Subject to any disclaimer, the term of this patent is extended or adjusted under 35 U.S.C. 154(b) by 223 days.

(21) Appl. No.: 17/440,239

(22) PCT Filed: Mar. 19, 2020

(86) PCT No.: PCT/JP2020/012253
§ 371 (c)(1),
(2) Date: Sep. 17, 2021

(87) PCT Pub. No.: WO2020/189756
PCT Pub. Date: Sep. 24, 2020

(65) Prior Publication Data
US 2022/0090103 A1    Mar. 24, 2022

(30) Foreign Application Priority Data
Mar. 21, 2019    (JP) .................................. 2019-053945

(51) Int. Cl.
*C12N 15/82*    (2006.01)
(52) U.S. Cl.
CPC ..... *C12N 15/8205* (2013.01); *C12N 15/8241* (2013.01)
(58) Field of Classification Search
CPC .............................................. C12N 15/8205
See application file for complete search history.

(56) References Cited

U.S. PATENT DOCUMENTS

2016/0115500 A1*  4/2016  Cutler ................ C12N 15/8273
                                                     536/23.6

FOREIGN PATENT DOCUMENTS

| JP | 3-272682 A | 12/1991 |
| JP | 2007300903 A | * 11/2007 |
| JP | 2010-161989 A | 7/2010 |
| JP | 2014-3976 A | 1/2014 |
| JP | 2016-111926 A | 6/2016 |

OTHER PUBLICATIONS

Clough et al (Floral dip: a simplified method for Agrobacterium-mediated transformation of *Arabidopsis thaliana*. The Plant Journal. 16, 735-743, 1998) (Year: 1998).*
Haseloff et al (Removal of a cryptic intron and subcellular localization of green fluorescent protein are required to mark transgenic *Arabidopsis* plants brightly. Proc. Natl. Acad. Sci. 94, pp. 2122-2127, 1997) (Year: 1997).*
Komari (Transformation of cultured cells of Chenopodium quinoa by binary vectors that carry a fragment of DNA from the virulence region of pTiBo542. Plant Cell Reports, 9:303-306, 1990) (Year: 1990).*
Sawada (Changing Situation Relevant to the Taxonomy of Phytopathogenic *Rhizobium* Species and Their Re-Identification in NIAS Genebank. Microbial. Cult. Coll. 30: 13-27. 2014) (Year: 2014).*
Sawada_2014_English_Translation (Year: 2014).*
Mara et al (Floral-dip Transformation of *Arabidopsis thaliana* to Examine pTSO2::β-glucuronidase Reporter Gene Expression. Journal of Visualized Experiments. p. 1-3, 2010). (Year: 2010).*
JP-2007300903_English_Translation (Year: 2007).*
Knight et al (Investigating Agrobacterium-Mediated Transformation of Verticillium albo-atrum on Plant Surfaces. PLOS ONE vol. 5, Issue 10, p. 1-5, 2010) (Year: 2010).*
International Search Report and Written Opinion issued in corresponding International Patent Application No. PCT/JP2020/012253 (with English translation of International Search Report) mailed Jul. 14, 2020 (14 pages).
Komari, "Transformation of cultured cells of Chenopodium quinoa by binary vectors that carry a fragment of DNA from the virulence region of pTiBo542," Plant Cell Reports, 1990, vol. 9, pp. 303-306.
Imamura et al., "Isolation and characterization of the betalain biosynthesis gene involved in hypocotyl pigmentation of the allotetraploid chenopodium quinoa," Biochemical and Biophysical Research Communications, 2018, vol. 496, pp. 280-286.
Sawada et al., "Changing situation relevant to the taxonomy of phytopathogenic *Rhizobium* species and their re-identification in NIAS Genebank," Microbial. Cult. Coll., 2014, vol. 30, No. 1, pp. 13-27, tables 3, 4, Fig. 6 (partial English translation only).
Sawada et al., "Simultaneous identification of phytopathogenic *Rhizobium* species (former *Agrobacterium* species) using multiplex colony-direct PCR," Japanese Journal of Phytopathology, 2015, vol. 81, pp. 332-340, table 1 (partial English translation only).
Ezura et al., "Factors affecting the Agrobacterium-mediated transformation of melon (*Cucumis melo* L.)," Breeding Science, 1996, vol. 46, separate vol. 1, p. 263, results and discussion (partial English translation only).

* cited by examiner

*Primary Examiner* — Charles Logsdon
*Assistant Examiner* — Wayne Zhong
(74) *Attorney, Agent, or Firm* — Kilyk & Bowersox, P.L.L.C.

(57) ABSTRACT

Provided is a method of transforming *quinoa*. It has been found that a female organ of *quinoa* can be transformed by adding sealing treatment to a floral dip method.

7 Claims, 38 Drawing Sheets
Specification includes a Sequence Listing.

SMOOTH MUTANT

REBC GENE IS DYSFUNCTION
BLADDERS ARE NOT FORMED
CHLOROPLASTS ARE YELLOW GREEN

INTRODUCTION OF NORMAL REBC GENE INTO rebc MUTANT BY NOVEL TRANSFORMATION METHOD (PATENT PENDING)

SUCCESSFULLY TRANSFORMED INDIVIDUAL
BLADDERS ARE FORMED
GREEN COLOR OF LEAVES IS RESTORED

TRANSFORMANT

METHOD FOR PRODUCING TRANSFORMED PLANT AND TRANSFORMATION AGENT

TECHNICAL FIELD

The present application is a National Stage Application of PCT/JP2020/012253, filed Mar. 19, 2020, which claims priority from Japanese Patent Application No. 2019-053945, which is incorporated herein by reference. The present invention relates to a method of producing a transformed plant and a transformation agent.

BACKGROUND ART

Quinoa (*Chenopodium quinoa*) is an allopolyploid plant native to the Andes, belonging to the genus *Chenopodium* of the subfamily Chenopodioideae of the family Amaranthaceae.

Seeds of *quinoa* are rich in proteins, essential amino acids, and minerals, and are expected to potentially serve as an alternative to rice (Non Patent Literature 1 and Non Patent Literature 2).

Further, with its excellent environmental stress tolerance, such as salt tolerance and cold tolerance, *quinoa* can be expected to be cultivated under a harsh environment (Non Patent Literature 3), and the Food and Agriculture Organization (FAO) of the United Nations evaluated *quinoa* as having a potential to be an important solution to the world's food crisis (Non Patent Literature 4). *Quinoa*, which has been an important food in the Andes, has now spread to the rest of the world, where *quinoa* is cultivated for research and commercial use. Further, decoding of a genome of *quinoa* (Non Patent Literature 5) has led to research on genes involved in the excellent environmental stress tolerance of *quinoa* (Non Patent Literature 6). It is conceived that a further environmental stress tolerance ability can be imparted to *quinoa* through use of a transformation technology.

Currently, an *Agrobacterium* (*Rhizobium radiobacter*; former name: *Agrobacterium tumefaciens*) method, which involves utilizing an ability of the bacterium to incorporate its DNA into a plant cell, is a mainstream method of transforming a plant. The DNA to be incorporated into a plant cell by the *Agrobacterium* is called transferred DNA (T-DNA), and transfer of the T-DNA is carried out through actions of a virulence (vir) gene cluster on a plasmid. When a phenolic compound is secreted as a result of damage to a host plant, the *Agrobacterium* is attracted to a cell of the plant and adheres to a surface of the plant. In the bacterium, VirA that has detected the phenolic compound phosphorylates VirG to activate other members of the vir gene cluster. Activated VirD1/D2 produce nicks in a T-DNA region on the plasmid, and VirD2 binds to a 5' end thereof. Further, VirE2, which serves to protect the T-complex, binds thereto. The complex of the T-strand with VirD2 and VirE2 is transported into the plant cell through an action of VirB, is transferred into a nucleus of the plant, and is finally incorporated into a chromosome (Non Patent Literature 7).

In many of transformation systems based on the *Agrobacterium* method, a gene is introduced into a plant of interest under an aseptic condition in vitro, followed by selection using a drug resistance gene. Then, cells having introduced therein the gene need to be redifferentiated by a tissue culture technology. The redifferentiation has the following disadvantages: an advanced technology and a long period of time are required; mutations occur in genes during a process of the redifferentiation; and applicable plant species are limited (Non Patent Literature 8).

Transformation with the *Agrobacterium* using a redifferentiation system has also been attempted in the genus *Chenopodium* including *quinoa*. There are reports of: transformation of cultured cells of *quinoa* using a binary vector (Non Patent Literature 9); transformation of *Chenopodium rubrum* seedlings with the *Agrobacterium* using a sonication (SAAT) method (Non Patent Literature 10); and induction of hairy roots of *Chenopodium rubrum* and *Chenopodium murale* L. with *Rhizobium rhizogenes* (Non Patent Literature 11 and Non Patent Literature 12). In those investigations, gene introduction was successfully performed through use of an *Agrobacterium* A281 strain having high transformation efficiency called supervirulence or hypervirulence (Non Patent Literature 9 and Non Patent Literature 13). However, no redifferentiation system for *quinoa* has been established, and a method of transforming *quinoa* has yet to be established.

Since the first transformed plant bodies were reported in tobacco (Non Patent Literature 14 and Non Patent Literature 15), highly efficient and stable transformation systems have been established in various plants, especially model plants, and have become indispensable methods in plant science. *Quinoa* has potentially excellent traits. In addition, it is desired that even better traits be imparted in order to elucidate functions of unknown genes and to cope with environmental and social changes. It is conceived that establishment of a transformation method is essential for progress of *quinoa* research.

CITATION LIST

Non Patent Literature

[NPL 1] Vega-Galvez A, Miranda M, Vergara J, Uribe E, Puente L, Martinez E A (2010) Nutrition facts and functional potential of *quinoa* (*Chenopodium quinoa* willd.), an ancient Andean grain: a review. Journal of the Science of Food and Agriculture 90:2541-2547

[NPL 2] Mota C, Santos M, Mauro R, Samman N, Matos A S, Torres D, Castanheira I (2016) Protein content and amino acids profile of pseudocereals. Food Chemistry 193: 55-61

[NPL 3] Hinojosa L, Gonzalez J A, Barrios-Masias F H, Fuentes F, Murphy K M (2018) *Quinoa* Abiotic Stress Responses: A Review. Plants 7 (4)

[NPL 4] Food and Agriculture Organization of the United Nations (2013) State of the Art Report on *Quinoa* Around the World in 2013.

[NPL 5] Jarvis D E, Ho Y S, Lightfoot D J, Schmockel S M, Li B, Borm T J, Ohyanagi H, Mineta K, Michell C T, Saber N, Kharbatia N M, Rupper R R, Sharp A R, Dally N, Boughton B A, Woo Y H, Gao G, Schijlen E G, Guo X, Momin A A, Negrao S, Al-Babili S, Gehring C, Roessner U, Jung C, Murphy K, Arold S T, Gojobori T, Linden C G, van Loo E N, Jellen E N, Maughan P J, Tester M (2017) Thegenome of *Chenopodium quinoa*. Nature 542 (7641): 307-312

[NPL 6] Morton M J L, Awlia M, Al-Tamimi N, Saade S, Pailles Y, Negrao S, Tester M (2019) Salt stress under the scalpel-dissecting the genetics of salt tolerance. The Plant Journal 97 (1): 148-163

[NPL 7] Zupan J R, Zambryski P (1995) Transfer of T-DNA from *Agrobacterium* to the plant cell. Plant Physiol 107 (4): 1041-1047

[NPL 8] Seki Shimizu, Susumu Kubota, and Takane Fujimori, (1987) Plant Biotechnology, Ohmsha, Ltd.

[NPL 9] Komari T (1990) Transformation of cultured cells of Chenopodiumquinoa by binary vectors that carry a fragment of DNA from the virulence region of pTiBo542. Plant Cell Reports 9:303-306

[NPL 10] Flores Solis J. I, Mlejnek P, Studena K, Prochazka S (2003) Application of sonication-assisted *Agrobacterium*-mediated transformation in *Chenopodium rubrum* L. Plant, Soil and Environment 49:255-260

[NPL 11] Mitic N, Dmitrovic S, Djordjevic M, Zdravkovic-Korac S, Nikolic, Raspor M, Djordjevic T, Maksimovic V, Zivkovic S, Krstic-Milosevic D, Stanisic M, Ninkovic S, (2012) Use of *Chenopodium murale* L. transgenic hairy root invitro culture system as a new tool for allelopathic assays. Journal of Plant Physiology 169:1203-1211

[NPL 12] Dmitrovic S, Mitic N, Zdravkovic-Korac S, Vinterhalter B, Ninkovic Sand Culafic L. J (2010) Hairy roots formation inrecalcitrant-to-transform plant *Chenopodium rubrum*. Biologia Plantarum 54 (3): 566-570

[NPL 13] Jin S G, Komari T, Gordon M P, Nester E W (1987) Genes responsible for the supervirulence phenotype of *Agrobacterium tumefaciens* A281. Journal of Bacteriology 169 (10): 4417-4425

[NPL 14] Block M D, Herrera-Estrella L, Montagu M V, Schell J, Zambryskil P (1984) Expression of foreign genes in regenerated plants and in their progeny. The EMBO Journal 3 (8): 1681-1689

[NPL 15] Horsch R B, Fraley R T, Rogers S G, Sanders P R, Lloyd A, Hoffmann N (1984) Inheritance of functional foreign genes in plants. Science 223 (4635): 496-498

SUMMARY OF INVENTION

Technical Problem

In order to solve the problems of the related art as described above, an object of the present invention is to provide a method of transforming *quinoa*.

Solution to Problem

The inventors of the present invention have made extensive investigations in order to achieve the above-mentioned object. As a result, the inventors have found that a female organ of *quinoa* can be transformed by adding sealing treatment to a floral dip method, and have further recognized that a gene introduced through the transformation can be inherited by progeny. Thus, the present invention has been completed.

That is, the present invention is as described below.

1. A method of producing a transformed plant, a seed of the plant, or a callus of the plant, the method including the following steps:
    (1-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
    (1-2) a step of cutting the plant body; and
    (1-3) a step of placing the cut plant body including a site having introduced therein the gene of interest under high-humidity and dark conditions to obtain a plant body having introduced therein the gene of interest; or (2-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
    (2-2) a step of cutting the plant body;
    (2-3) a step of placing the cut plant body including a site having introduced therein the gene of interest under high-humidity and dark conditions; and (2-4) a step of growing the plant body until a seed is ready to be harvested, to thereby obtain a seed having introduced therein the gene of interest; or (3-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
    (3-2) a step of placing the inoculated plant body under high-humidity and dark conditions;
    (3-3) a step of cutting the plant body;
    (3-4) a step of placing the cut plant body including a site having introduced therein the gene of interest under high-humidity and dark conditions; and
    (3-5) a step of producing a callus from the plant body.

2. The method according to Item 1, wherein the *Agrobacterium* is an MAFF301276 strain or an MAFF311303 strain.

3. The method according to Item 1 or 2, wherein the *Agrobacterium* is an *Agrobacterium* further transformed with a Ti plasmid which is derived from an *Agrobacterium* strain MAFF301276 and from which a T-DNA region has been removed.

4. The method according to any one of Items 1 to 3, wherein the plant body is *quinoa*.

5. The method according to any one of Items 1 to 4, wherein the plant body is a *quinoa* mutant ghy or a *quinoa* mutant ghy/rebc.

6. The method according to any one of Items 1 to 5, further including a step of bringing abscisic acid into contact with the target plant body before the step (1-1) or the step (2-1), simultaneously with the step (1-1) or the step (2-1), or between the step (1-1) and the step (1-2) or between the step (2-1) and the step (2-2).

7. A transformation agent, including an *Agrobacterium* strain MAFF311303 transformed with:
    a Ti plasmid which is derived from an *Agrobacterium* strain MAFF301276 and from which a T-DNA region has been removed; and
    an expression vector carrying a gene of interest under control of a promoter capable of inducing expression of the gene of interest in a plant body.

8. A female organ-specific transformation agent, including an *Agrobacterium* strain MAFF311303.

9. A plant transformation aid using an *Agrobacterium*, including abscisic acid.

10. A *quinoa* transformation agent, including an *Agrobacterium* strain MAFF301276.

11. A method of producing a transformed plant, including the following step:
    (1) a step of bringing an *Agrobacterium* strain MAFF311303 transformed with an expression vector carrying a gene of interest under control of a promoter capable of inducing expression of the gene of interest in a plant body and with a Ti plasmid which is derived from an *Agrobacterium* strain MAFF301276 and from which a T-DNA region has been removed into contact with a target plant body to inoculate the *Agrobacterium* thereinto.

12. A method of producing a transformed plant, including the following steps:
   (1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto; and
   (2) a step of bringing abscisic acid into contact with the target plant body before the step (1), simultaneously with the step (1), or after the step (1).

13. A method of producing a transformed plant, including the following steps:
   (1) a step of bringing an *Agrobacterium* strain MAFF311303 transformed with an expression vector carrying a gene of interest under control of a promoter capable of inducing expression of the gene of interest in a plant body and with a Ti plasmid which is derived from an *Agrobacterium* strain MAFF301276 and from which a T-DNA region has been removed into contact with a target plant body to inoculate the *Agrobacterium* thereinto; and
   (2) a step of bringing abscisic acid into contact with the target plant body before the step (1), simultaneously with the step (1), or after the step (1).

14. The method according to Item 12, wherein the *Agrobacterium* is an MAFF301276 strain or an MAFF311303 strain.

15. A method of producing a seed of a transformed plant, including the following steps:
   (1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
   (2) a step of bringing abscisic acid into contact with the target plant body before the step (1), simultaneously with the step (1), or after the step (1); and
   (3) a step of growing the plant body until a seed is ready to be harvested, to thereby obtain a seed having introduced therein the gene of interest.

16. The method according to Item 15, wherein the *Agrobacterium* is an MAFF301276 strain or an MAFF311303 strain.

17. The method according to any one of Items 11 to 16, wherein the plant body is *quinoa*.

18. The method according to any one of Items 11 to 17, wherein the plant body is a *quinoa* mutant ghy or a *quinoa* mutant ghy/rebc.

Advantageous Effects of Invention

According to the present invention, the method of producing a transformed plant and the transformation agent can be provided.

BRIEF DESCRIPTION OF DRAWINGS

FIG. 12 show calluses at 6 weeks after infection treatment. The scale bars each represent 1 cm.

15 show calluses (hypocotyl sections) at 6 weeks after infection treatment. The scale bars each represent 1 cm.

Figure 16:
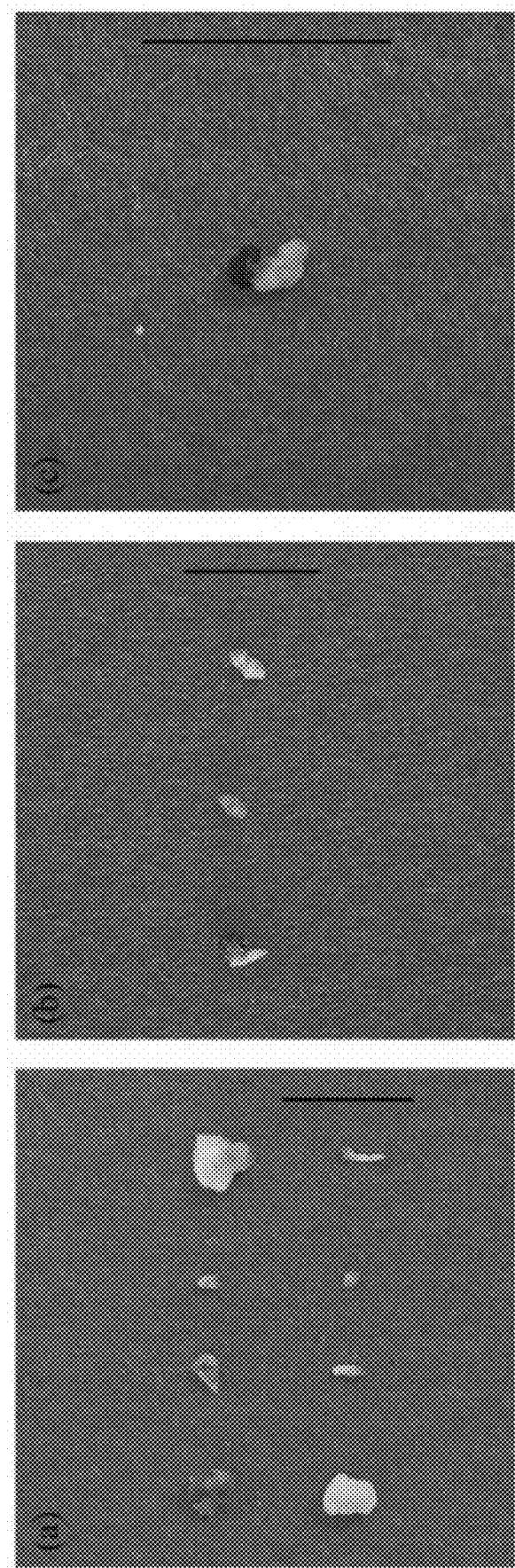

FIG. 16 show GUS expression in calluses induced from hypocotyl sections of *quinoa* infected with the *Agrobacterium* GV3101 strain. (a) Calluses of the 85 variety; (b) calluses of the mutant rebc; and (c) a callus of the mutant ghy. GUS staining was performed for calluses at 6 weeks after infection treatment. The scale bars each represent 1 cm.

Figure 17:
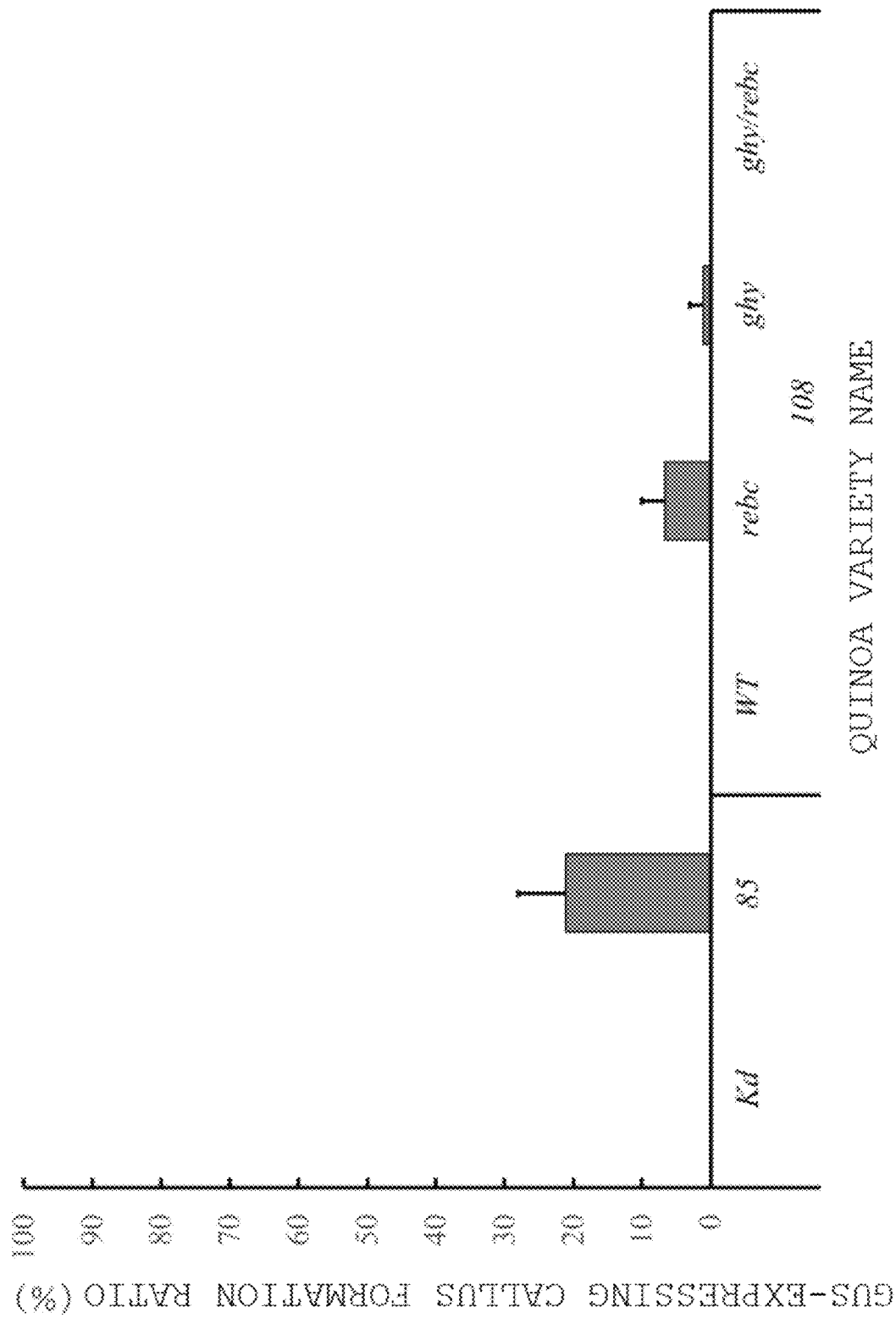

FIG. 17 shows transformed callus formation ratios of six varieties of *quinoa* infected with the *Agrobacterium* GV3101 strain. GUS staining was performed for calluses at 6 weeks after infection treatment. The graph shows the mean±standard deviation of three infection experiments in which hypocotyl sections (n=30) of *quinoa* were tested.

Figure 18:
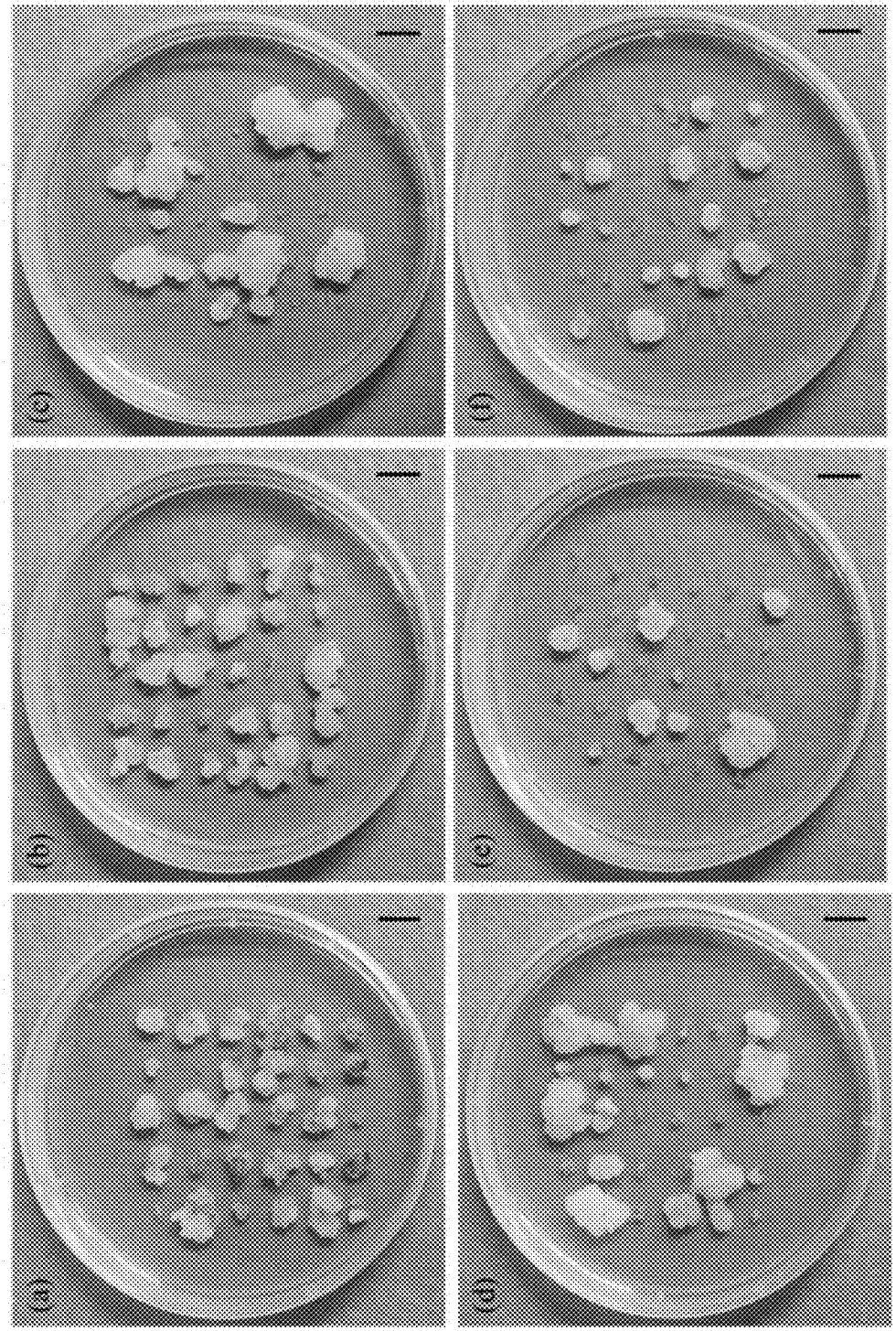

FIG. 18 show calluses induced from hypocotyl sections of *quinoa* infected with the *Agrobacterium* strain MAFF301276. (a) Calluses of the Kd variety; (b) calluses of the 85 variety; (c) calluses of the 108 variety; (d) calluses of the mutant rebc; (e) calluses of the mutant ghy; and (f) calluses of the mutant ghy/rebc. FIG. 18 show calluses (hypocotyl sections) at 6 weeks after infection treatment. The scale bars each represent 1 cm.

Figure 19:
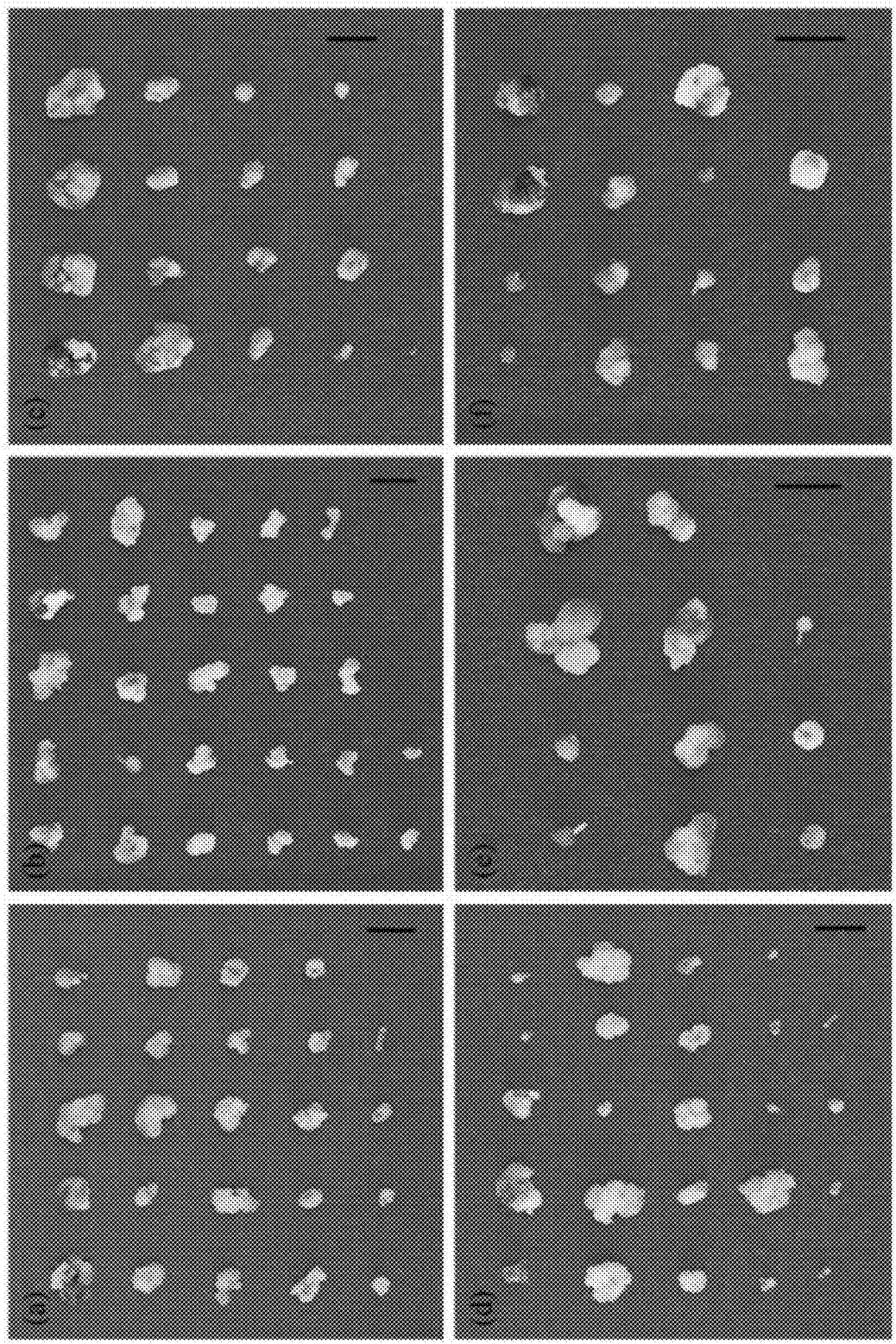

FIG. 19 show GUS expression in calluses induced from hypocotyl sections of *quinoa* infected with the *Agrobacterium* strain MAFF301276. (a) Calluses of the Kd variety; (b) calluses of the 85 variety; (c) calluses of the 108 variety; (d) calluses of the mutant rebc; (e) calluses of the mutant ghy; and (f) calluses of the mutant ghy/rebc. GUS staining was performed for calluses at 6 weeks after infection treatment. The scale bars each represent 1 cm.

Figure 20:
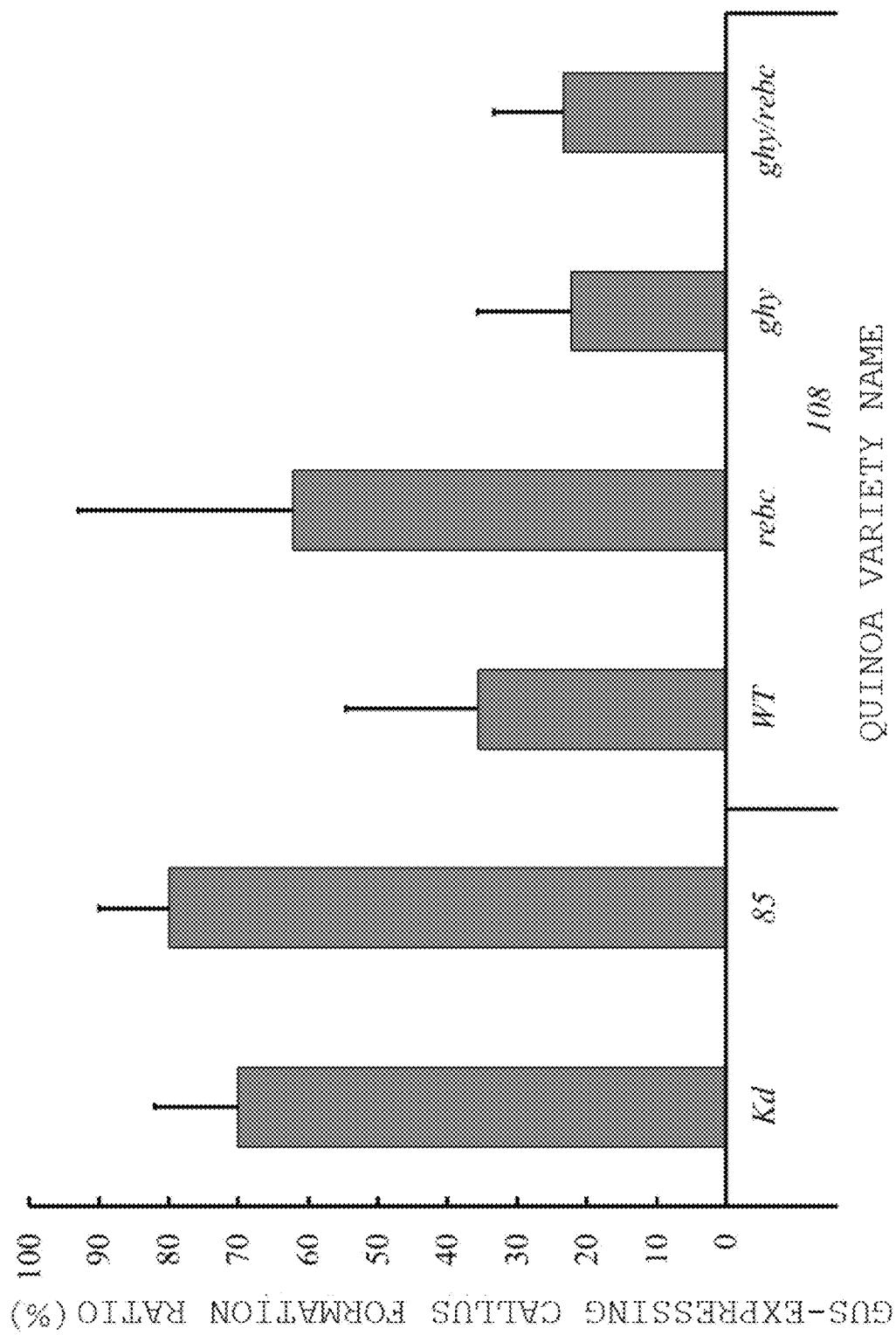

FIG. 20 shows transformed callus formation ratios of six varieties of *quinoa* infected with the *Agrobacterium* strain MAFF301276. GUS staining was performed for calluses at 6 weeks after infection treatment. The graph shows the mean±standard deviation of three infection experiments in which hypocotyl sections (n=30) of *quinoa* were tested.

Figure 21:
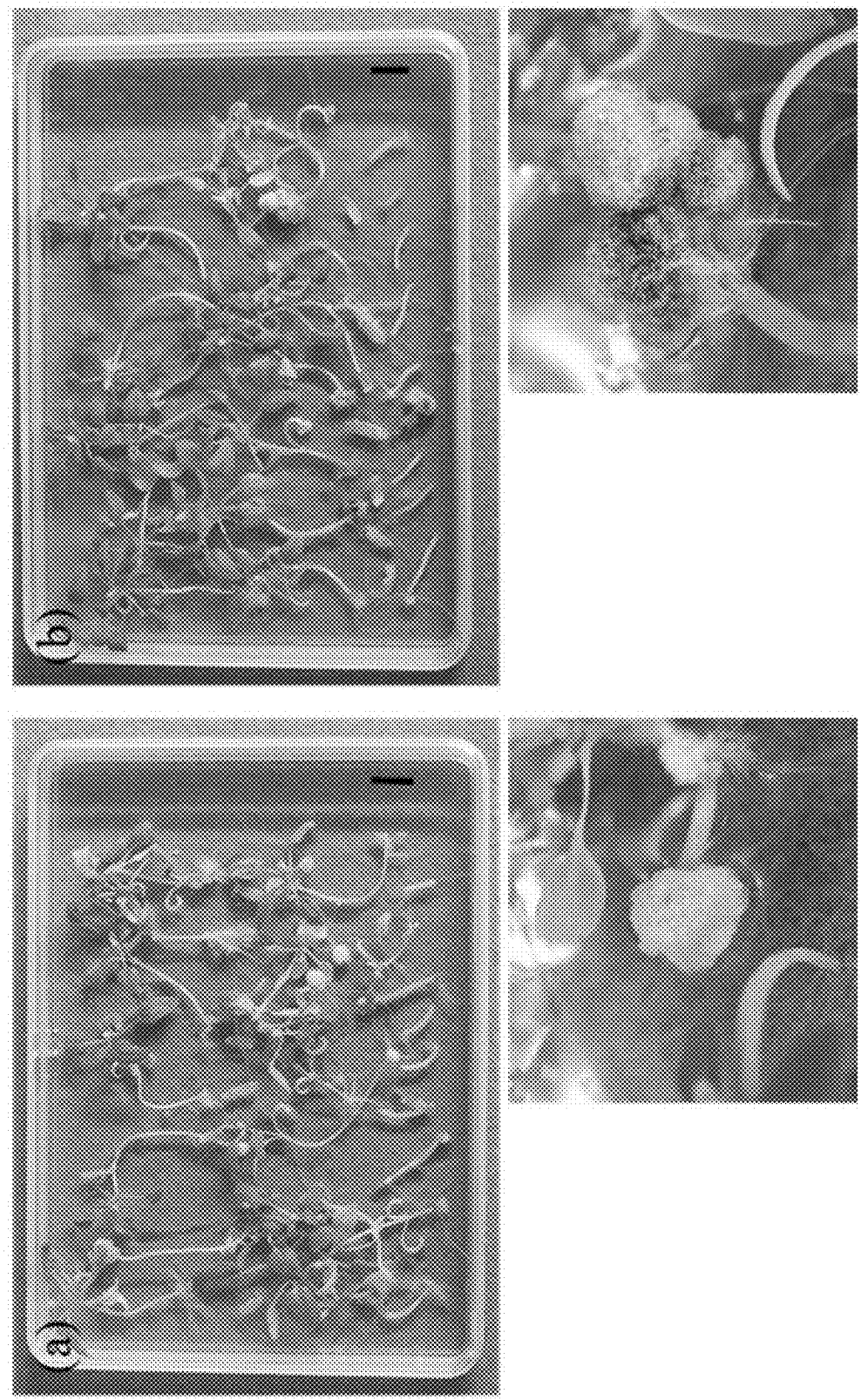

FIG. 21 show galls induced in seedlings of the mutant ghy/rebc with the *Agrobacterium* strain MAFF301276. (a) Seedlings infected with a bacterial strain harboring a binary vector pCAMBIA1301; and (b) seedlings infected with a bacterial strain harboring a binary vector pCAMBIA-CqCYP76AD1-1. FIG. 21 show seedlings at 6 weeks after infection treatment. The scale bars each represent 1 cm.

Figure 22:
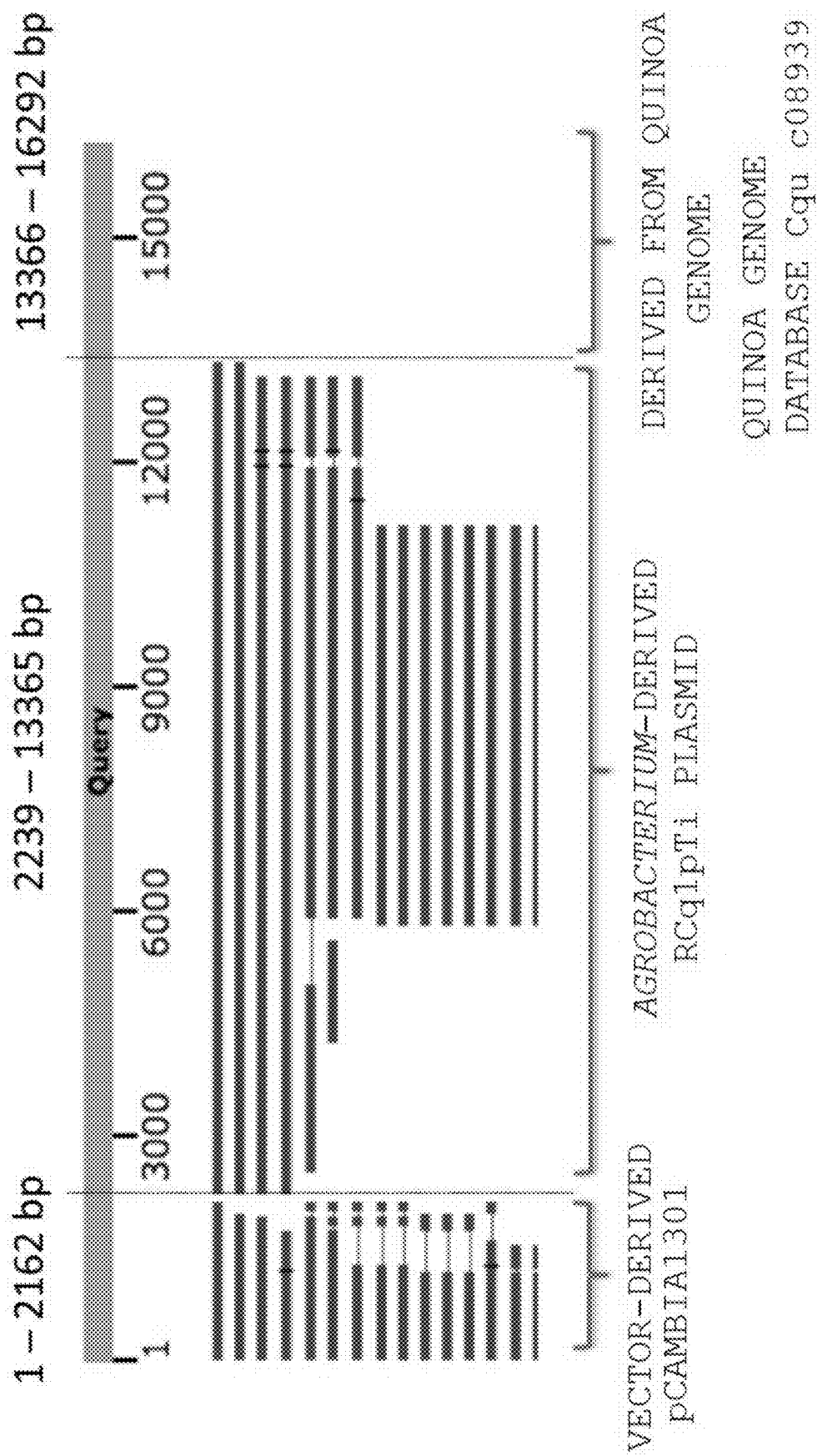

FIG. 22 is an illustration of a mode of introduction of an MAFF301276pTi plasmid and a pCAMBIA1301-derived plasmid into a *quinoa* genome. The T-DNA region of the binary vector pCAMBIA1301 and T-DNA derived from the MAFF301276 strain are inserted into the *quinoa* genome in the form of a fusion.

Figure 1:
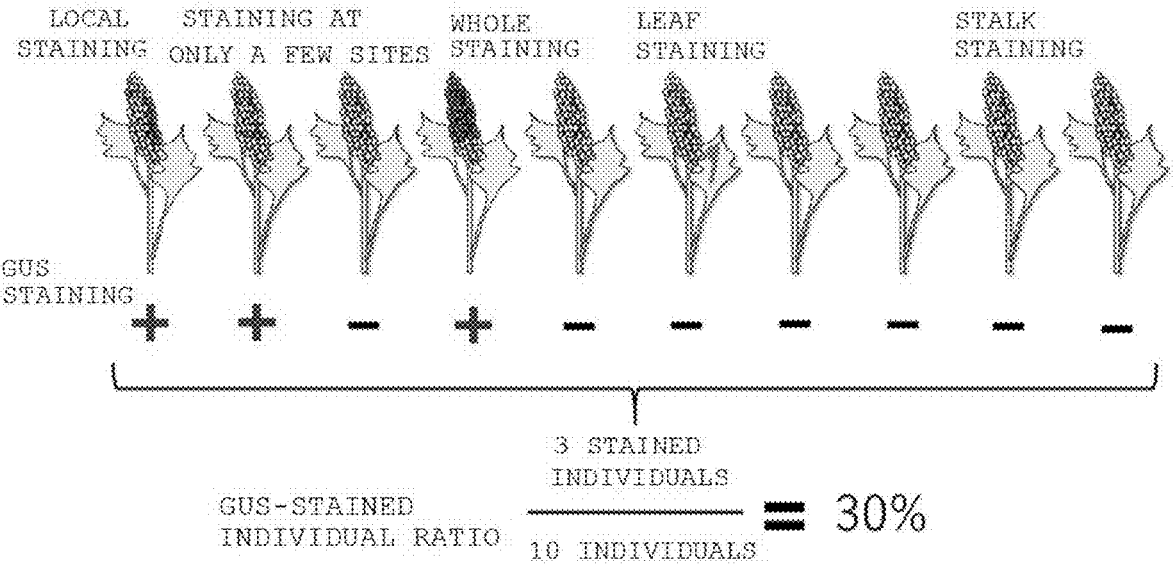
FIG. 1 includes illustrations of methods of measuring a ratio of GUS-expressing individuals.
Figure 1:
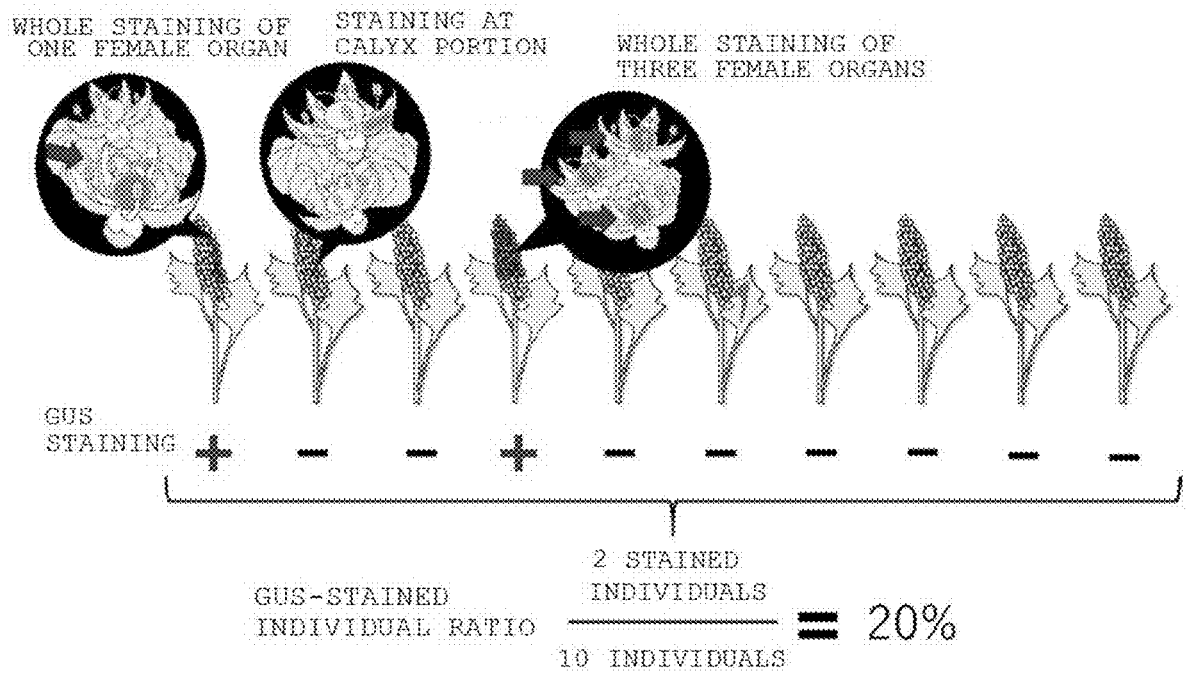
Figure 23:
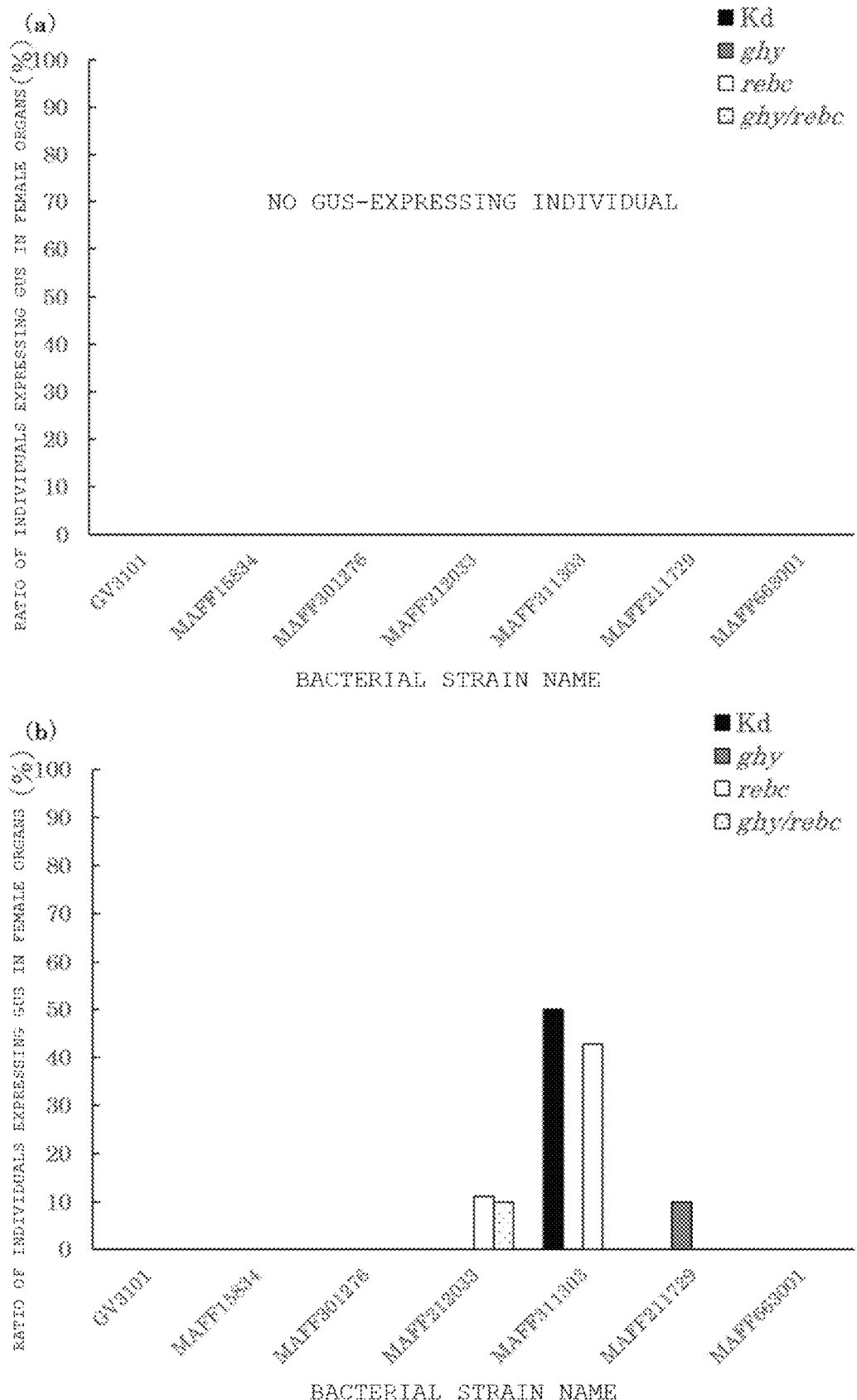

FIG. 23 show ratios of individuals found to exhibit GUS expression in their female organs through the floral dip/cutting-sealing method using four varieties of *quinoa* and seven bacterial strains. (a) staining GUS results for cutting-sealing treatment (−); and (b) GUS staining results for cutting-sealing treatment (+). The measurement method is illustrated in FIG. 1.

Figure 24:
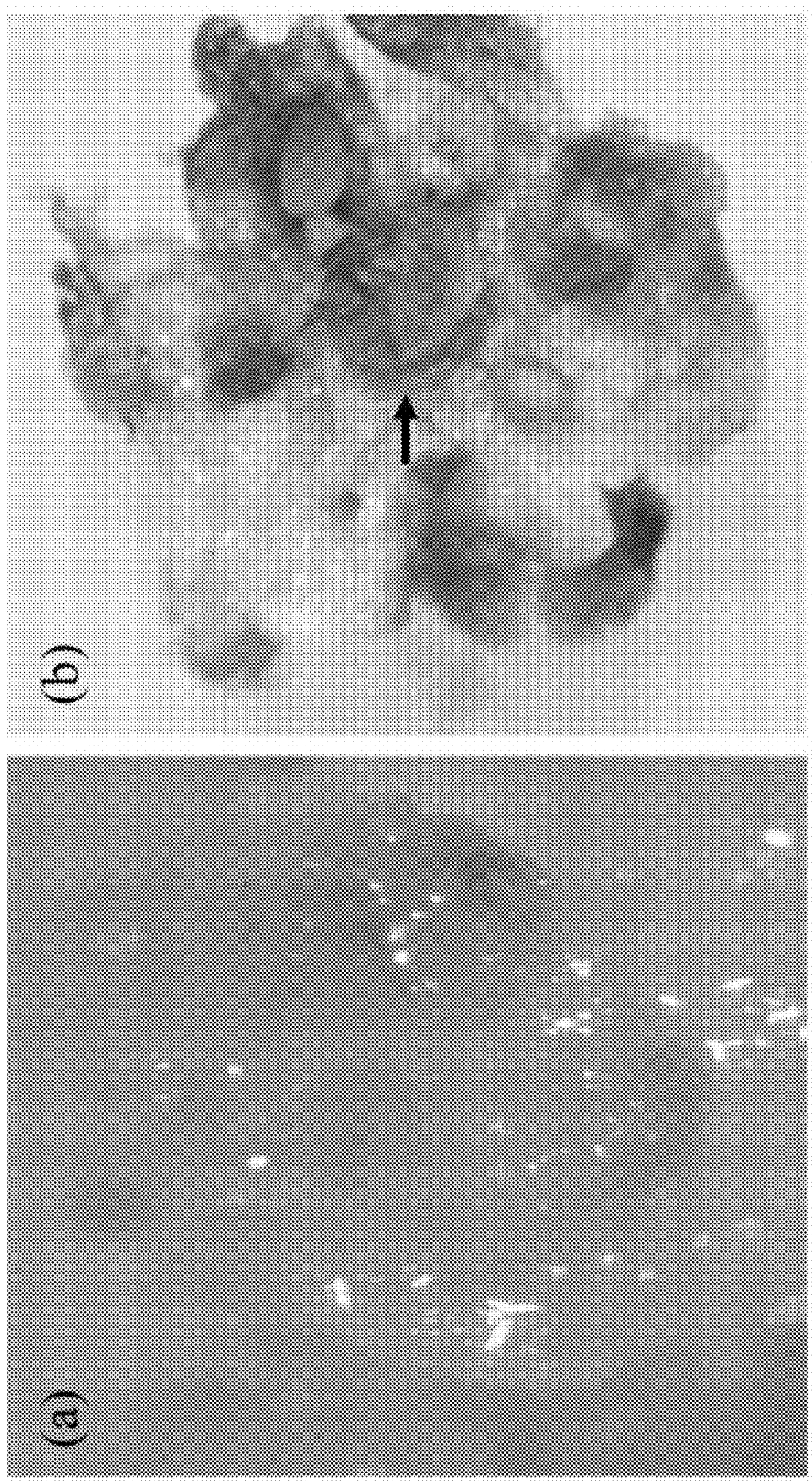

FIG. 24 show Kd variety *quinoa* subjected to a floral dip/cutting-sealing experiment. (a) A calyx found to exhibit GUS expression using the MAFF301276 strain; and (b) a female organ found to exhibit GUS expression using the MAFF311303 strain. The arrow indicates the female organ of *quinoa*.

Figure 25:
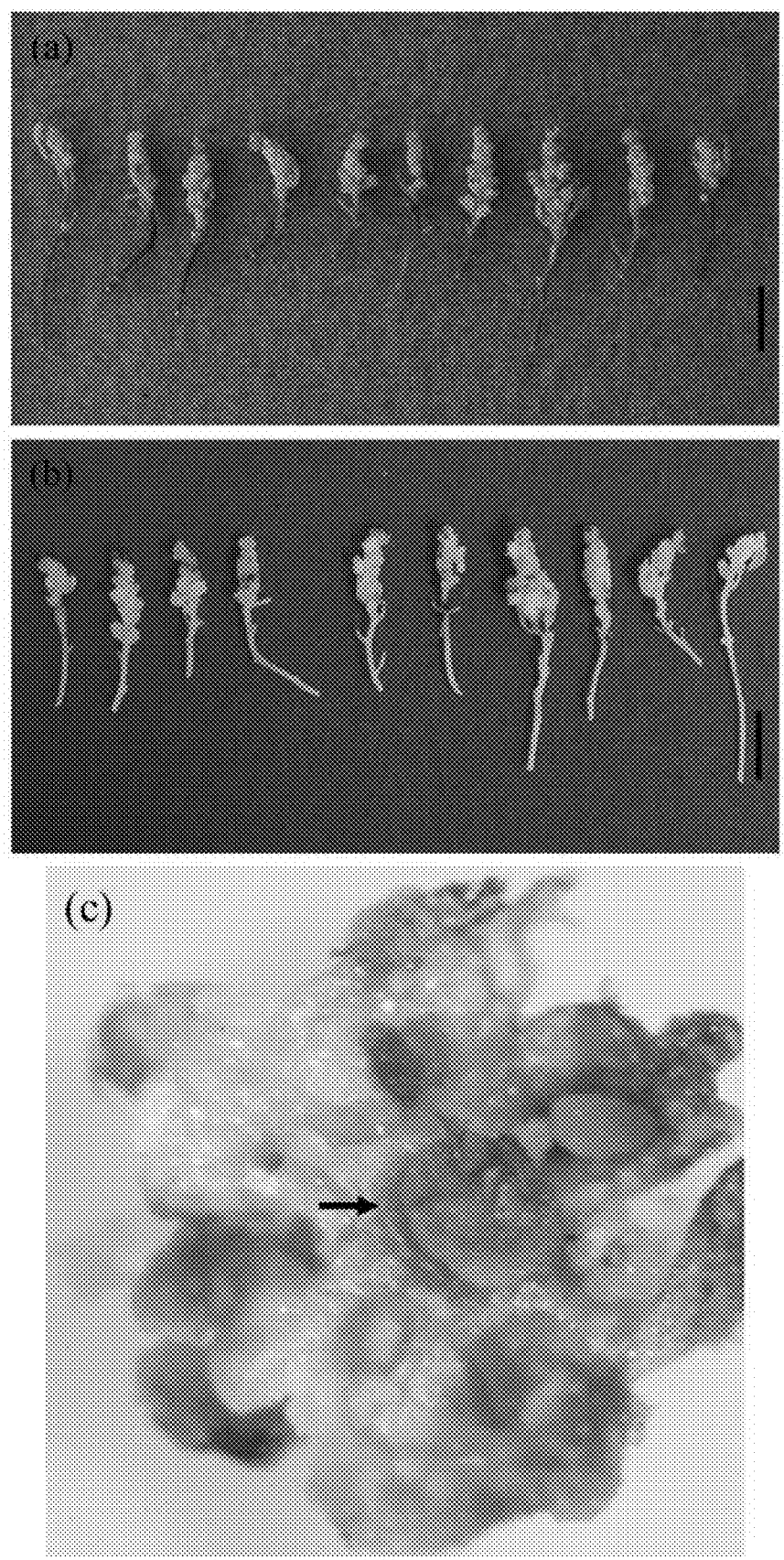

FIG. 25 show the Kd variety subjected to a floral dip/cutting-sealing experiment using the MAFF311303 strain. (a) *Quinoa* before GUS staining; (b) *quinoa* after GUS staining; and (c) a female organ found to exhibit GUS expression. The scale bars each represent 1 cm. The arrow indicates the female organ of *quinoa*.

Figure 2:
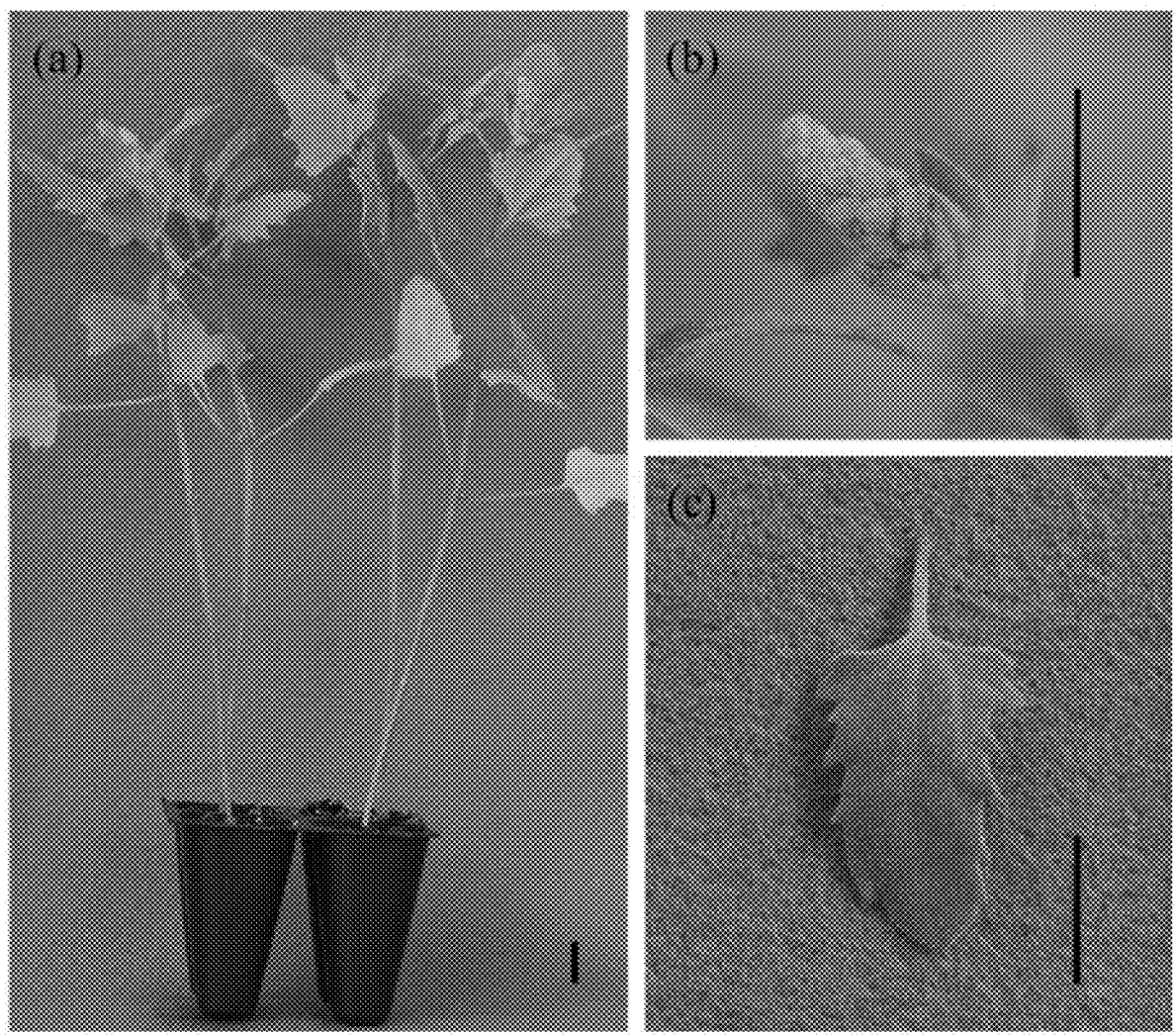
FIG. 2 show a Kd variety grown in sowing soil. (a) Full-length *quinoa*; (b) an ear; and (c) a leaf. The scale bars each represent 1 cm.
Figure 3:
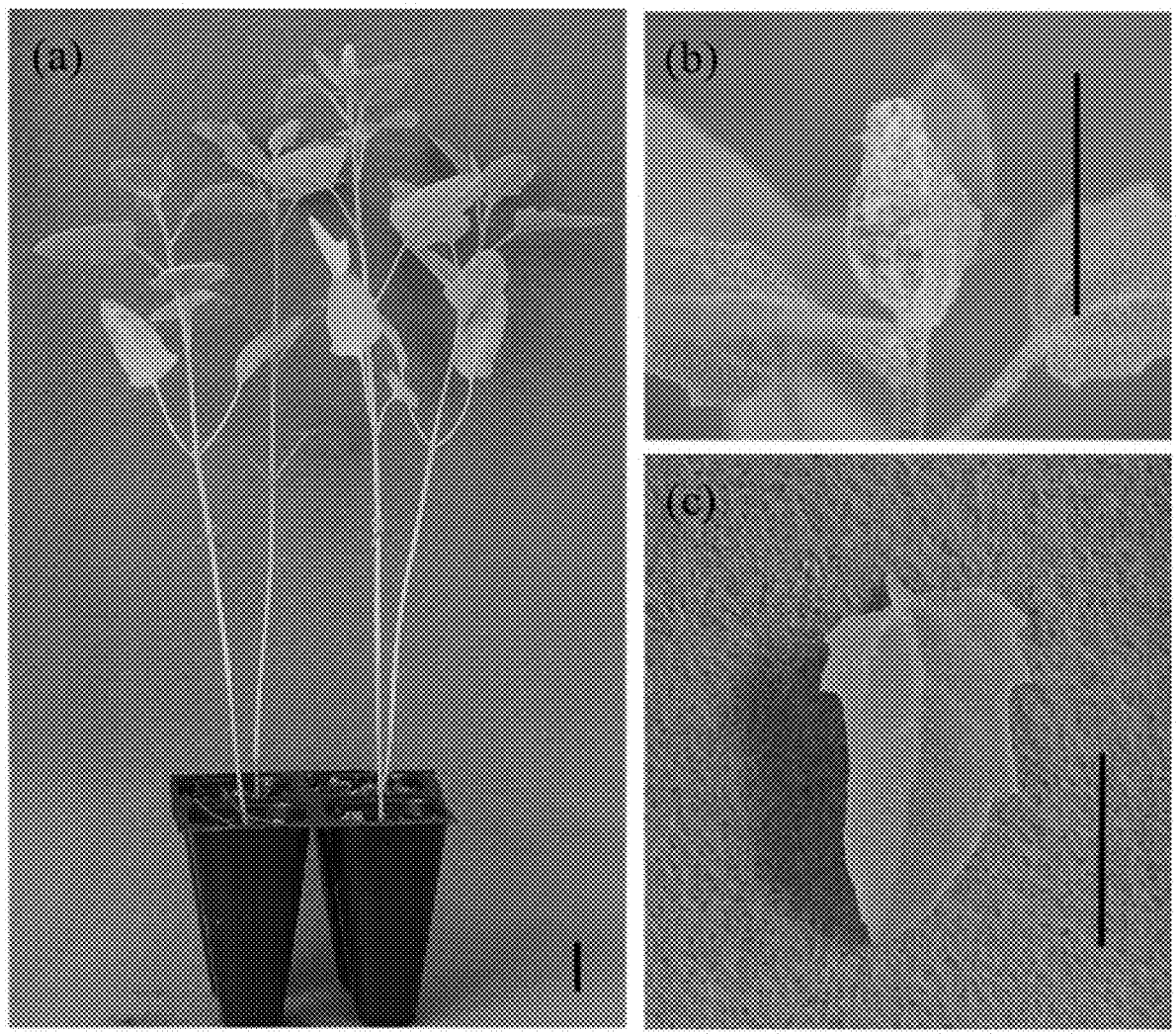
FIG. 3 show a mutant ghy grown in sowing soil. (a) Full-length *quinoa*; (b) an ear; and (c) a leaf. The scale bars each represent 1 cm.
Figure 4:
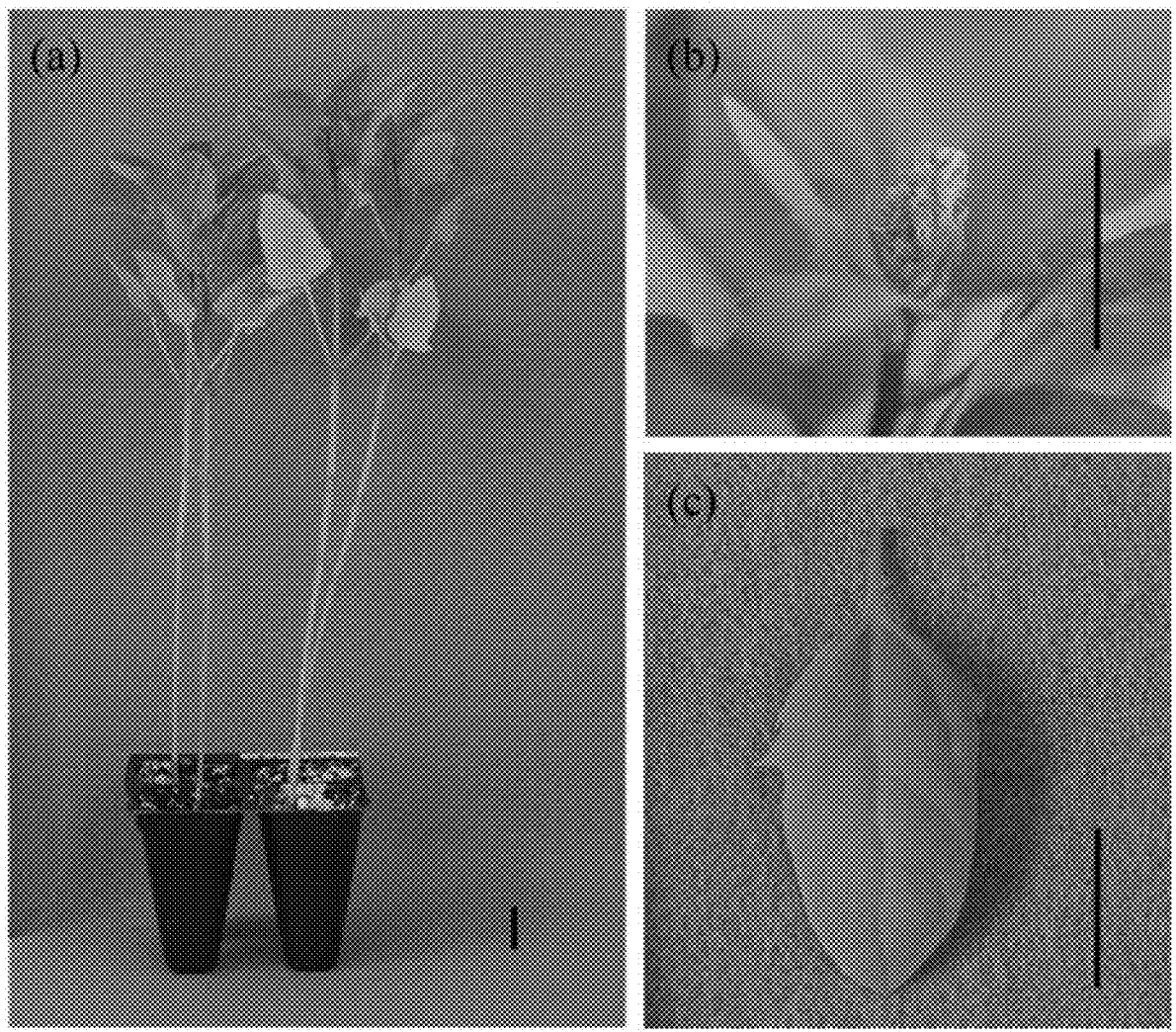
FIG. 4 show a mutant rebc grown in sowing soil. (a) Full-length *quinoa*; (b) an ear; and (c) a leaf. The scale bars each represent 1 cm.
Figure 5:
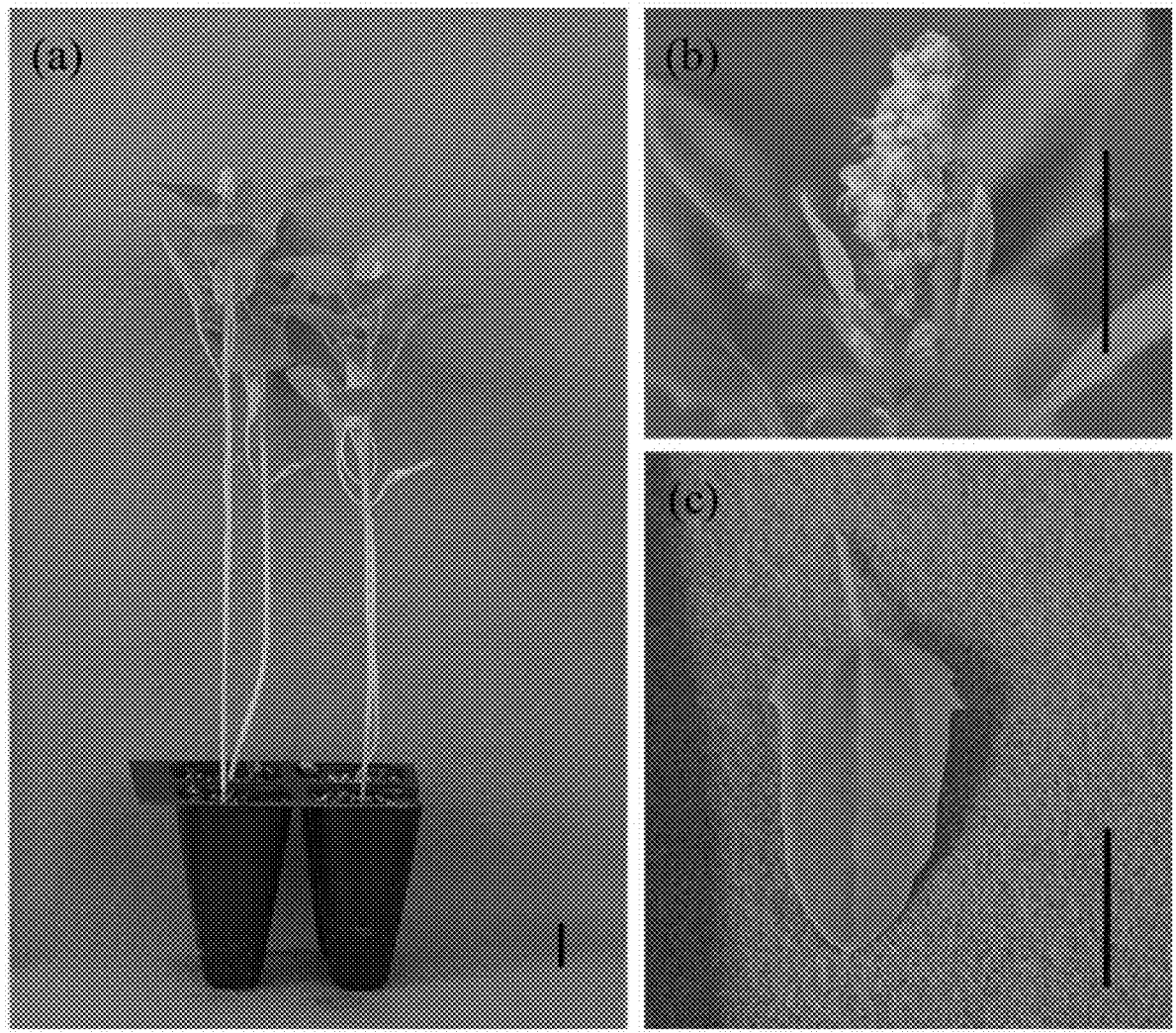
FIG. 5 show a mutant ghy/rebc grown in sowing soil. (a) Full-length *quinoa*; (b) an ear; and (c) a leaf. The scale bars each represent 1 cm.
Figure 26:
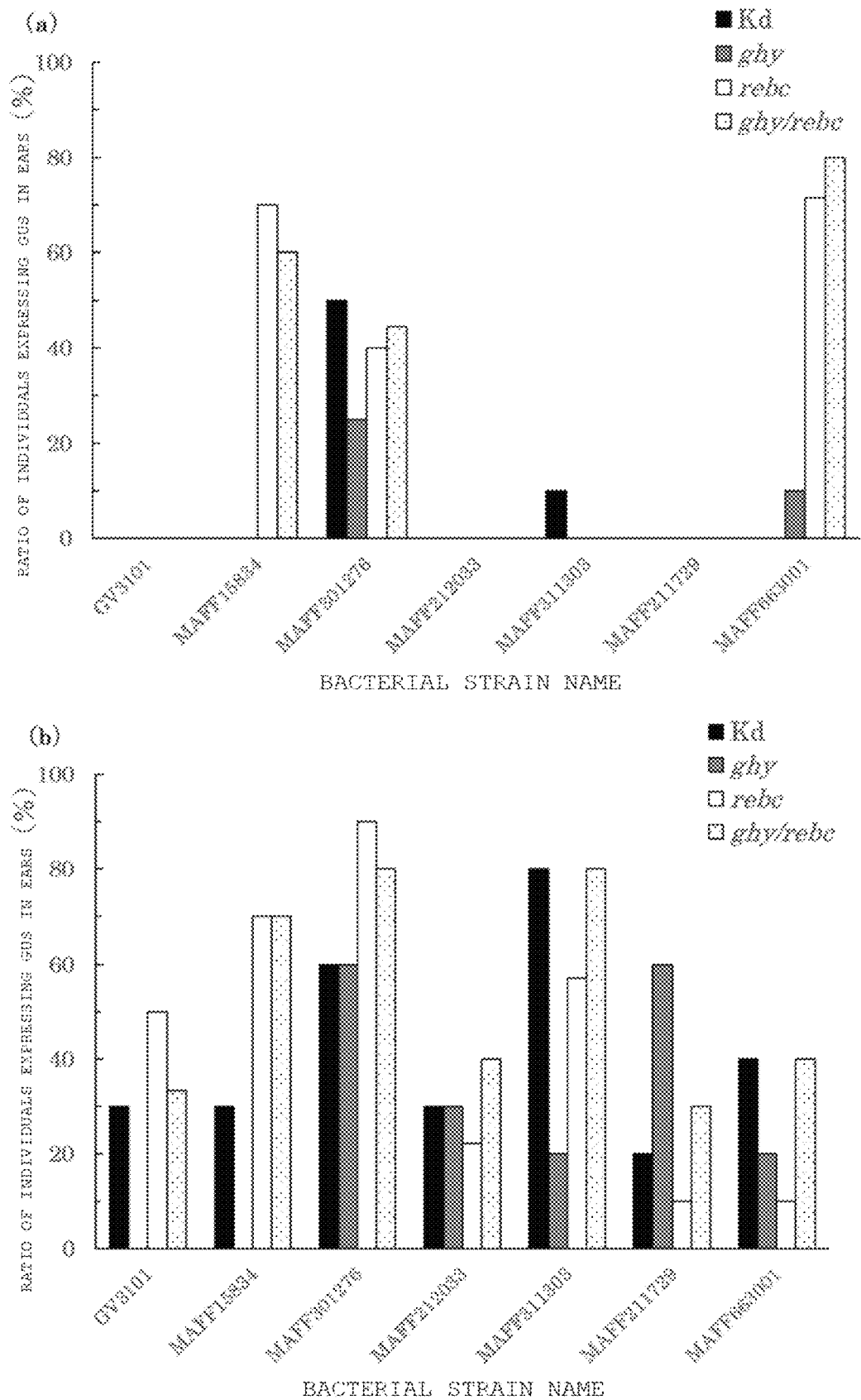

FIG. 26 show ratios of individuals found to exhibit GUS expression in their ears through the floral dip/cutting-sealing method using four varieties of *quinoa* and seven bacterial strains. (a) GUS staining results for cutting-sealing treatment (−); and (b) GUS staining results for cutting-sealing treatment (+). The measurement method is shown in FIG. 2.

Figure 27:
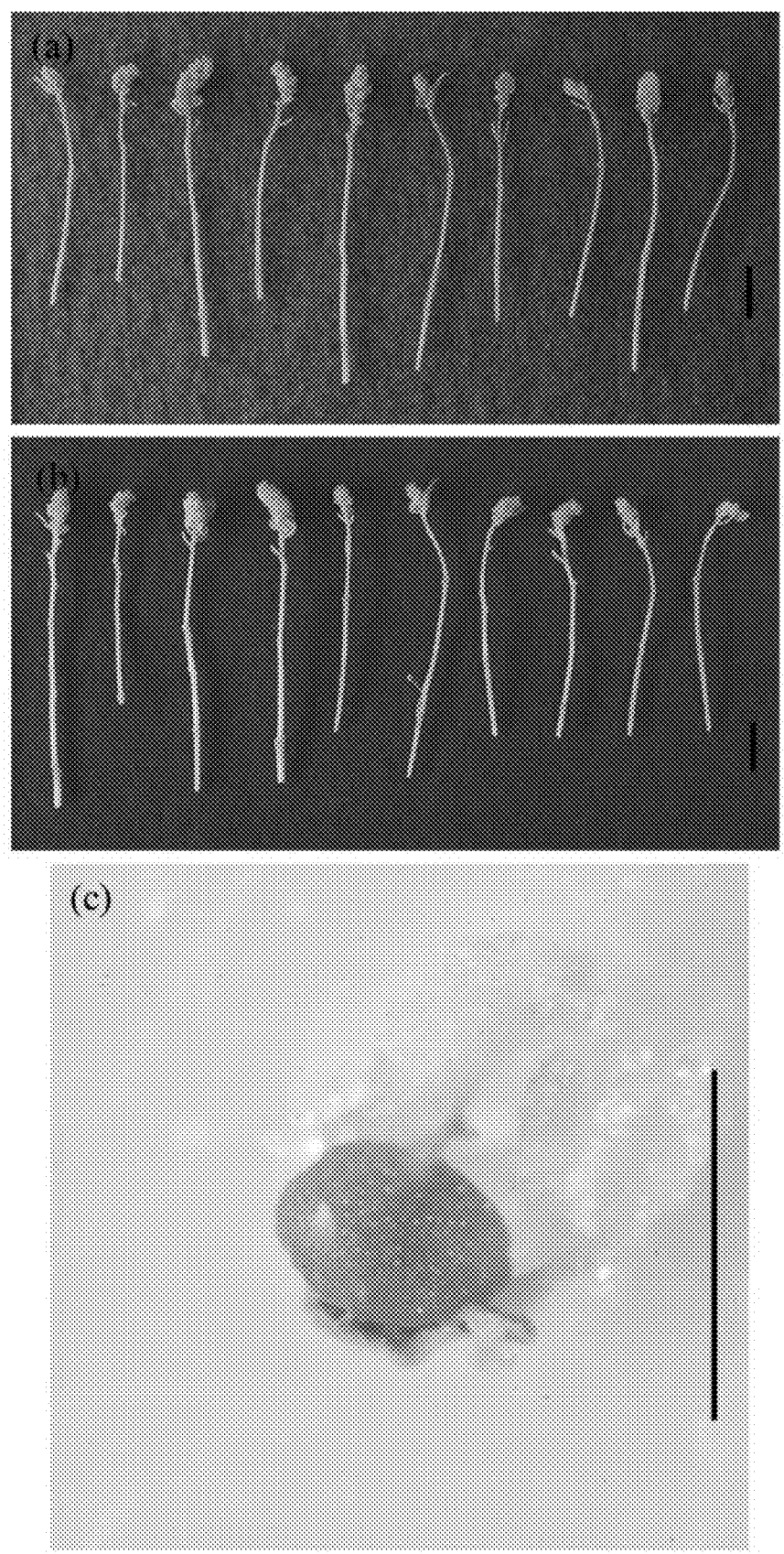

FIG. 27 show the mutant ghy subjected to a floral dip experiment using MAFF311303pTi301276ΔT-DNA. (a) *Quinoa* before GUS staining; (b) *quinoa* after GUS staining; and (c) a female organ found to exhibit GUS expression. The scale bars in (a) and (b) each represent 1 cm, and the scale bar in (c) represents 1 mm.

Figure 28:
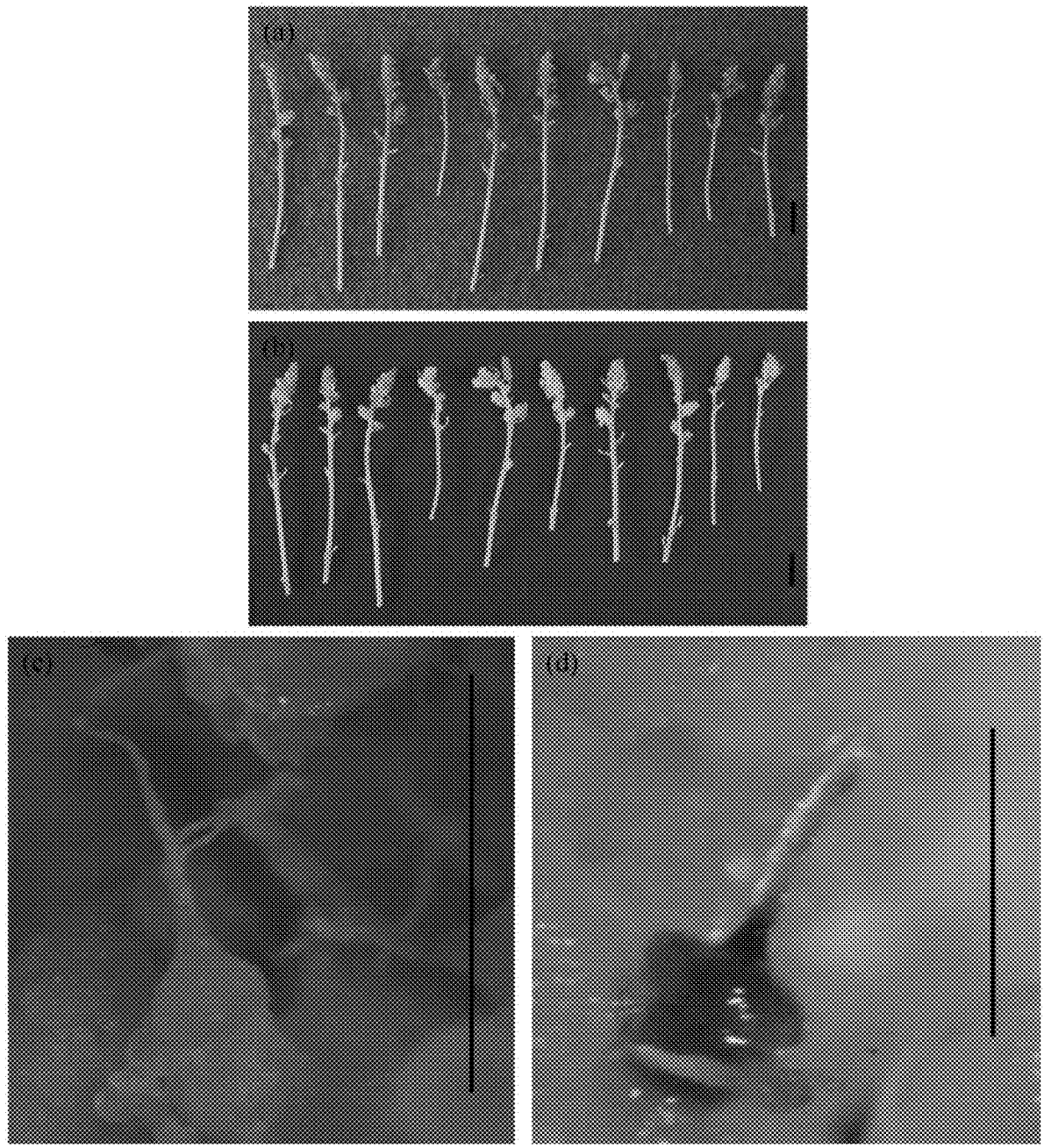

FIG. 28 show the mutant ghy/rebc subjected to a floral dip experiment using MAFF311303pTi301276ΔT-DNA. (a) *Quinoa* before GUS staining; (b) *quinoa* after GUS staining; (c) a non-GUS-expressing female organ; and (d) a female organ found to exhibit GUS expression. The scale bars in (a) and (b) each represent 1 cm, and the scale bars in (c) and (d) each represent 1 mm.

Figure 29:
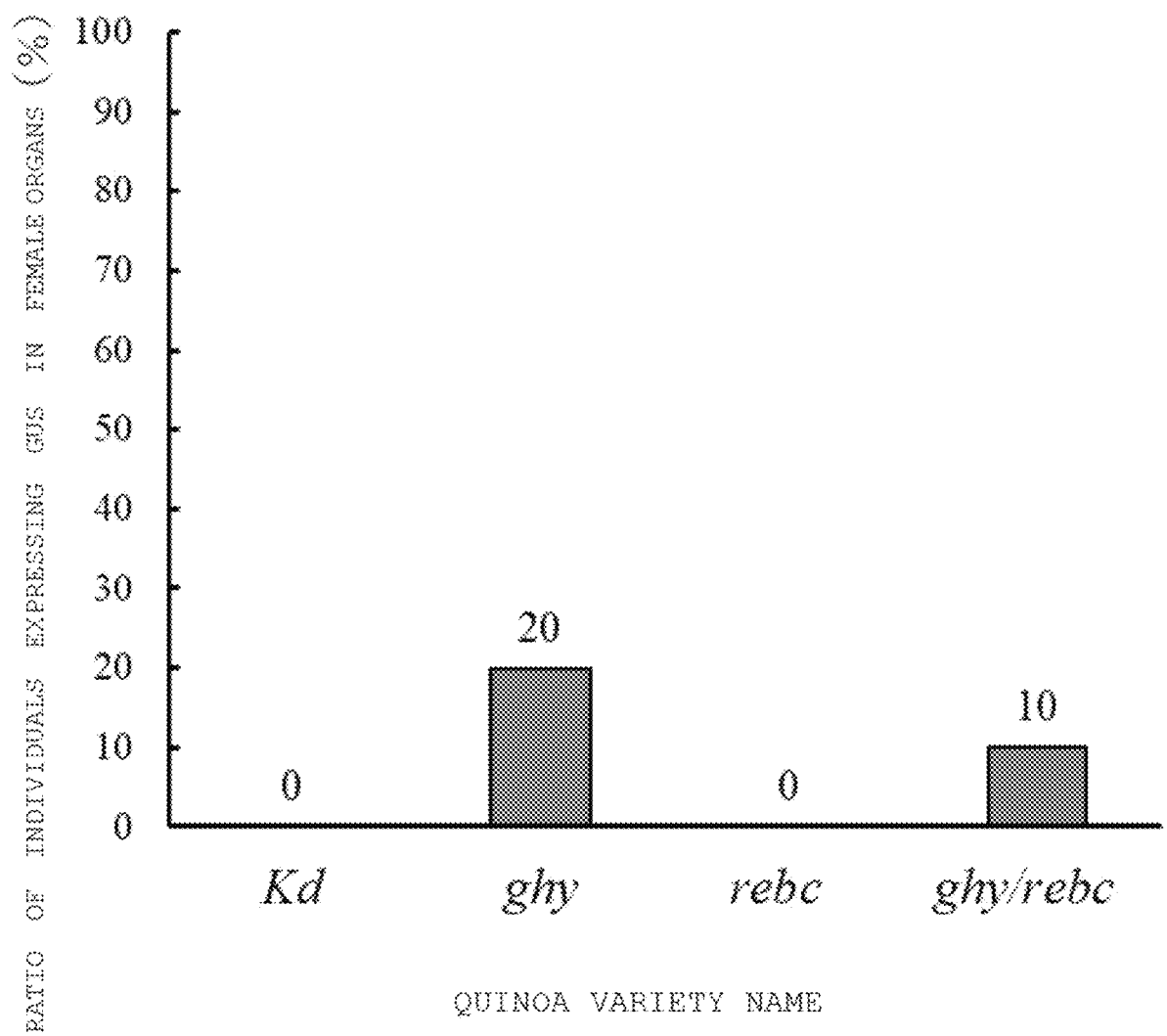

FIG. 29 shows ratios of individuals found to show GUS staining in their female organs through a floral dip experiment using MAFF311303pTiMAFF301276ΔT-DNA. An infection experiment was performed using four varieties of *quinoa*, and 10 individuals of each variety were subjected to GUS staining. A number shown above a *quinoa* variety name or above the graph represents a ratio of individuals found to exhibit GUS expression in their female organs.

Figure 30:
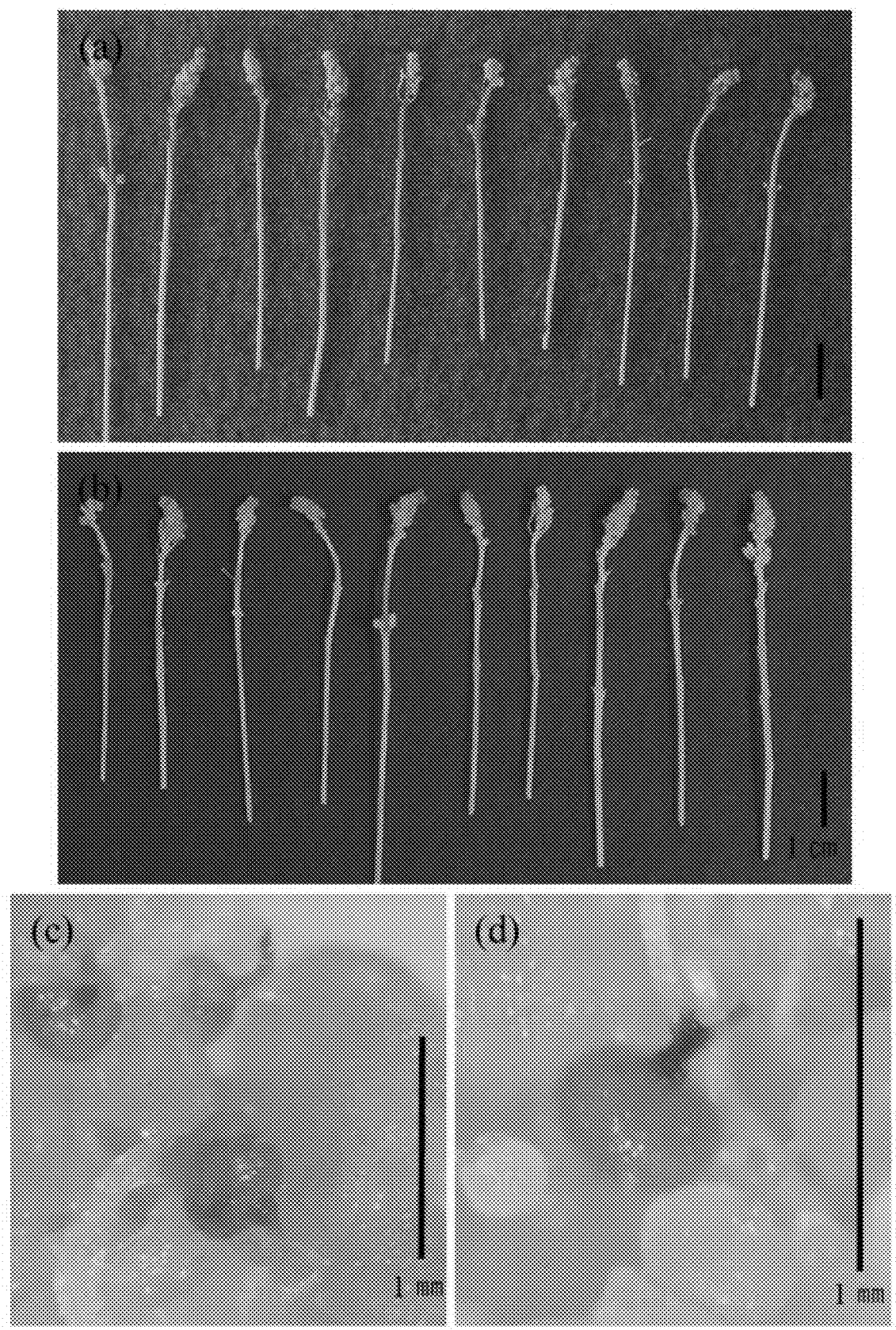

FIG. 30 show the mutant ghy/rebc subjected to a floral dip experiment using MAFF311303pTiMAFF301276ΔT-DNA and 500 mM ABA. (a) *Quinoa* before GUS staining; (b) *quinoa* after GUS staining; and (c) and (d) female organs found to exhibit GUS expression. The scale bars in (a) and (b) each represent 1 cm, and the scale bars in (c) and (d) each represent 1 mm.

Figure 31:
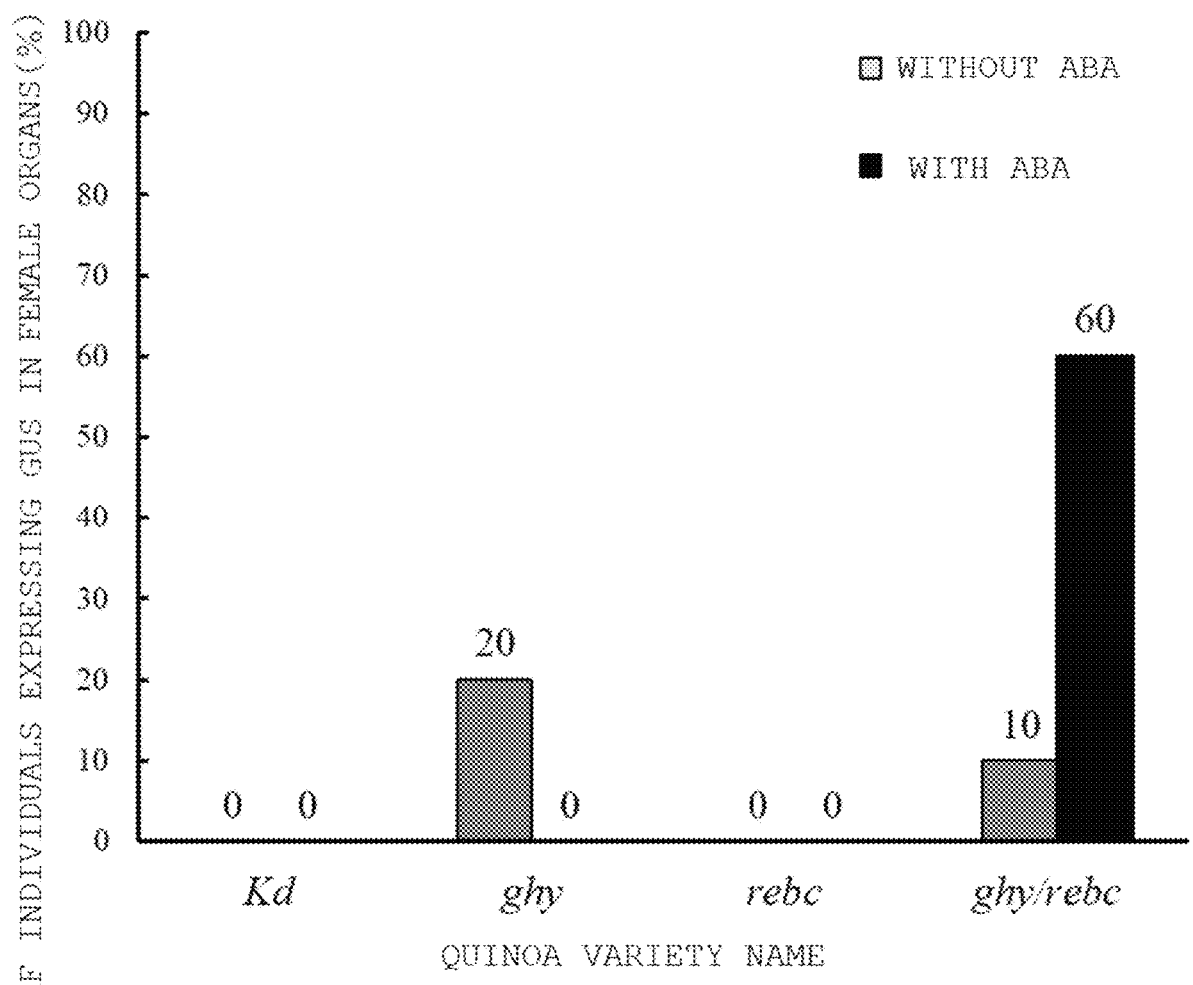

FIG. 31 shows ratios of individuals found to show GUS staining in their female organs through a floral dip experiment using MAFF311303pTiMAFF301276ΔT-DNA and 500 mM ABA. An infection experiment was performed using four varieties of *quinoa*, and 10 individuals of each variety were subjected to GUS staining. A number shown above a *quinoa* variety name or above the graph represents a ratio of individuals found to exhibit GUS expression in female organs.

Figure 32:
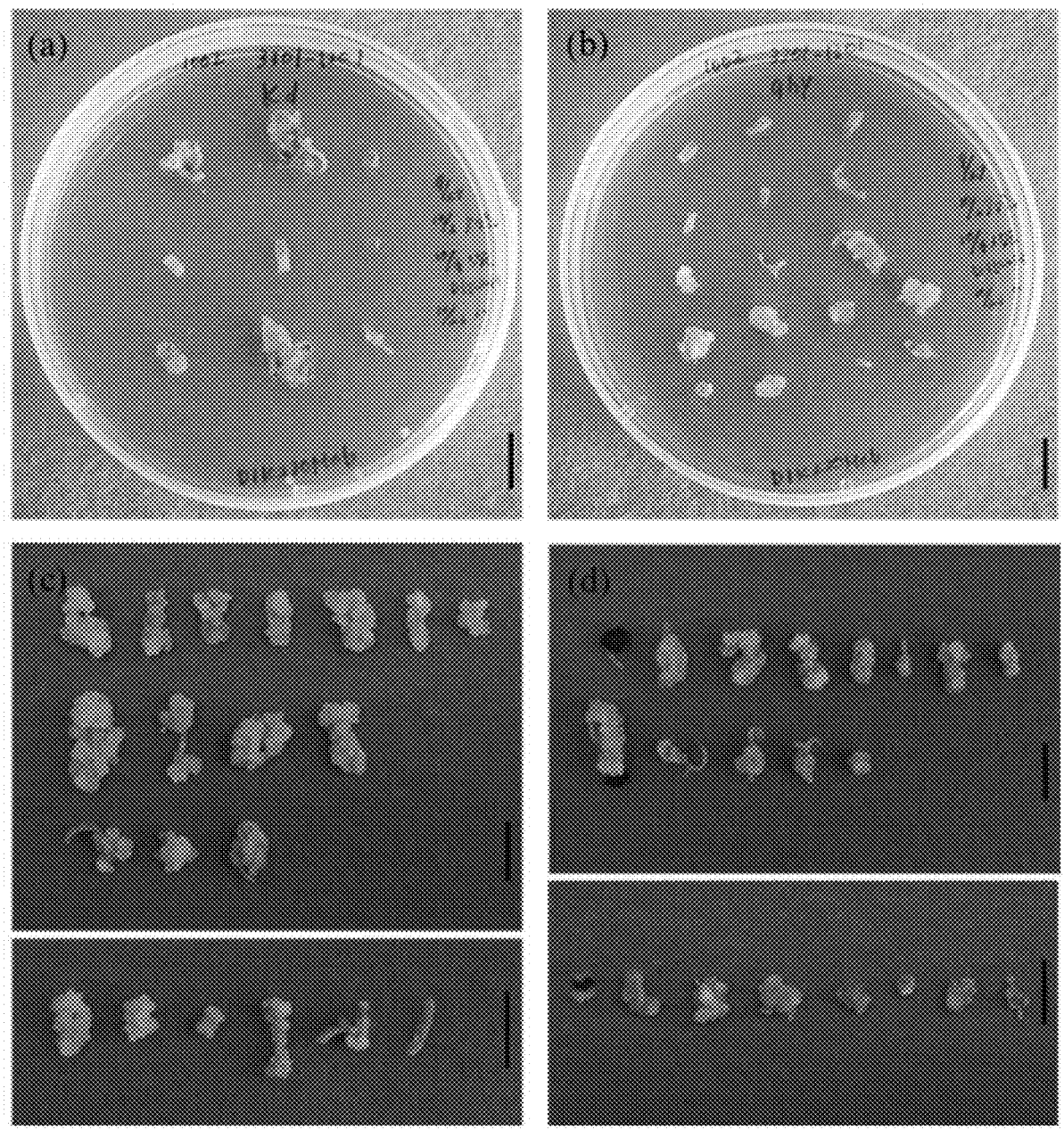

FIG. 32 show calluses induced from seedling sections of the Kd variety and the mutant ghy infected using the GV3101 strain. (a) Calluses of the Kd variety, (b) calluses of the mutant ghy, (c) GUS expression in calluses of the Kd variety, and (d) GUS expression in calluses of the mutant ghy. GUS staining was performed at 6 weeks after infection treatment. The scale bars each represent 1 cm.

Figure 33:
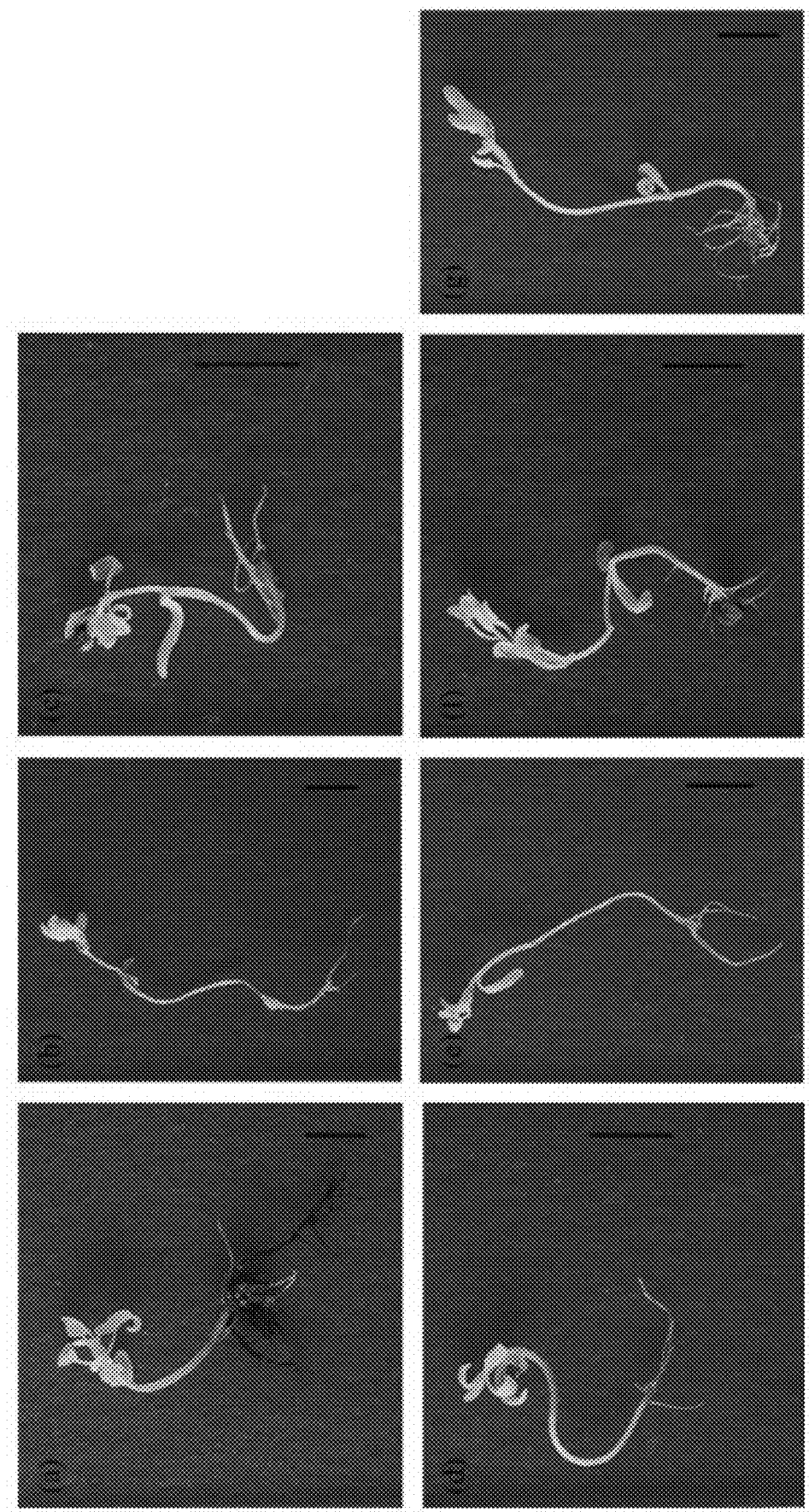

FIG. 33 show GUS expression in seedlings of the Kd variety infected with six *Agrobacterium* strains. (a) A seedling infected with the ATCC15834 strain; (b) and (c) seedlings infected with the MAFF301276 strain; (d) a seedling infected with the MAFF212033 strain; (e) a seedling infected with the MAFF311303 strain; (f) a seedling infected with the MAFF211729 strain; and (g) a seedling infected with the MAFF663001 strain. GUS staining was performed for seedlings at 5 weeks after infection treatment. The scale bars each represent 1 cm.

Figure 34:
Figure 34:
Figure 34:
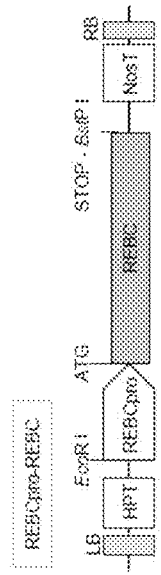
Figure 34:
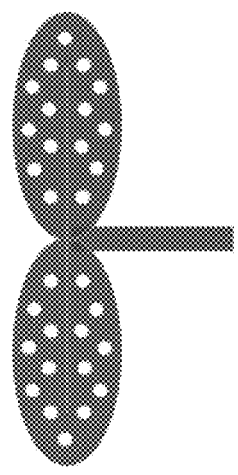

FIG. 34 is the outline of transformation of rebc mutant *quinoa* with a wild-type REBC gene by the floral dip/cutting-sealing method.

Figure 35:
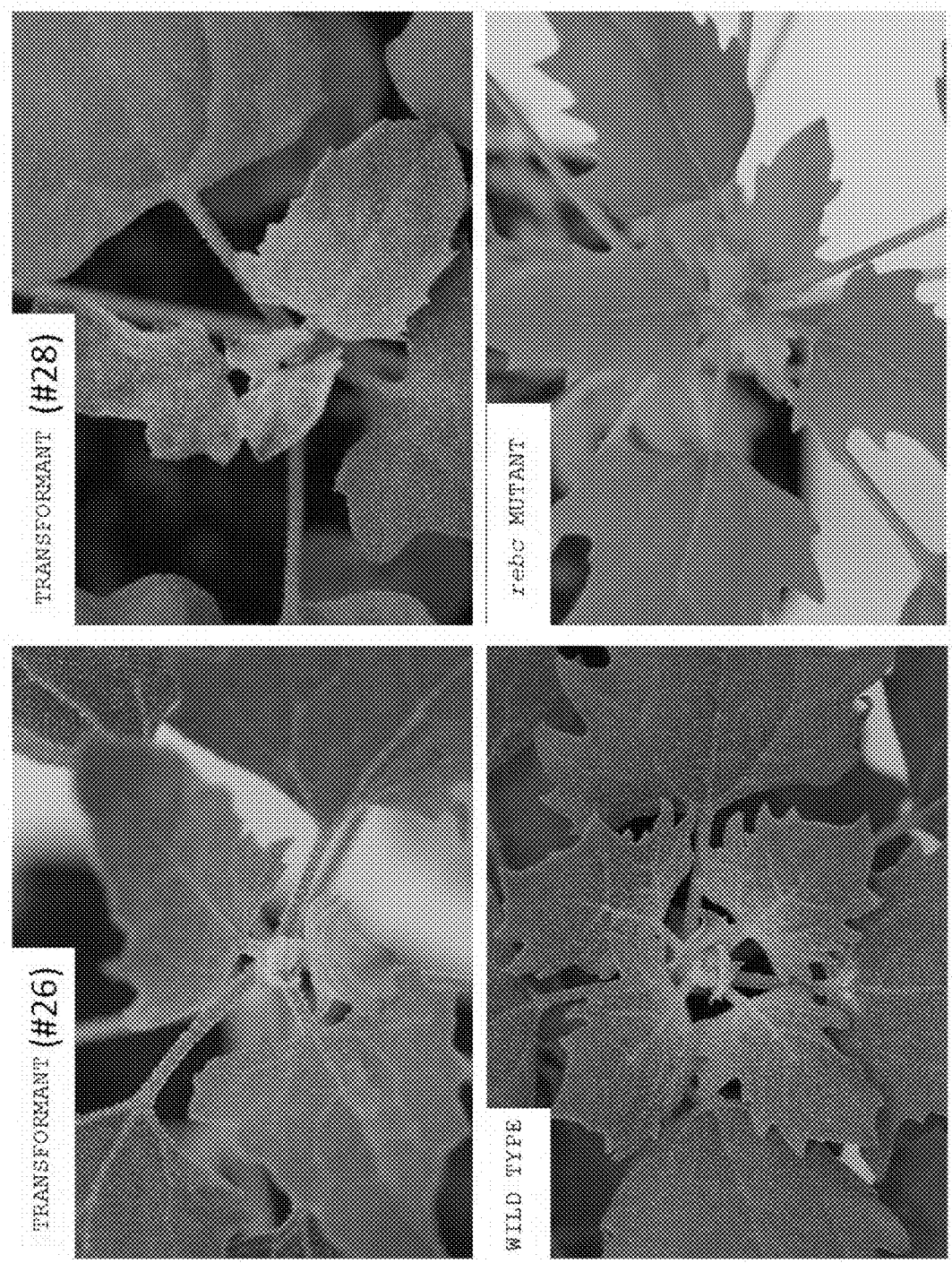

FIG. 35 shows the results of the transformation of rebc mutant *quinoa* with the wild-type REBC gene by the floral dip/cutting-sealing method. The upper panels show transformants (rebc mutation-complemented individuals) of a wild-type phenotype having bladders, and the lower panels show a wild type and the rebc mutant. The bladders were restored in the transformants.

Figure 36:
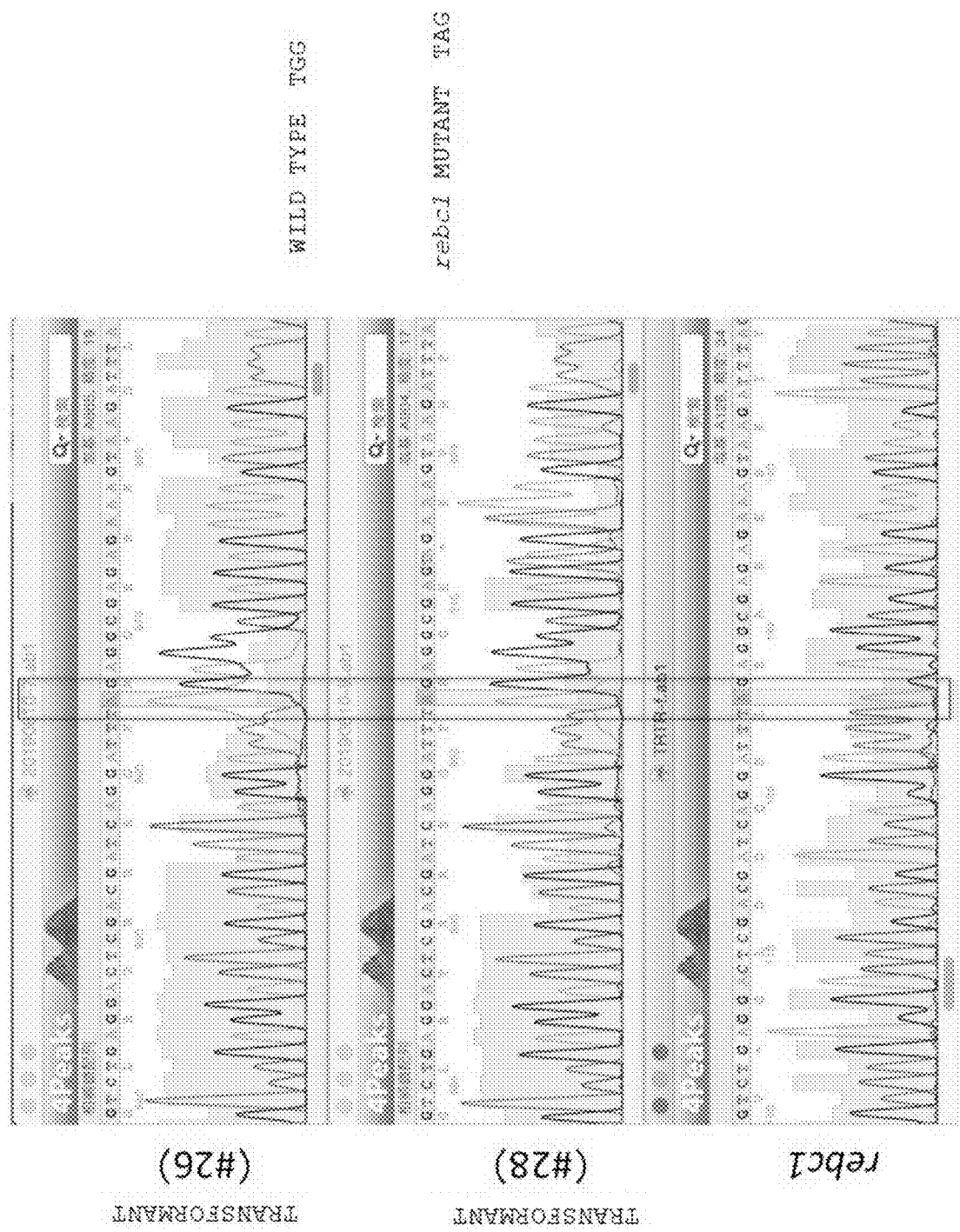

FIG. 36 shows the results of sequencing of the REBC genes of transformants.

Figure 37:
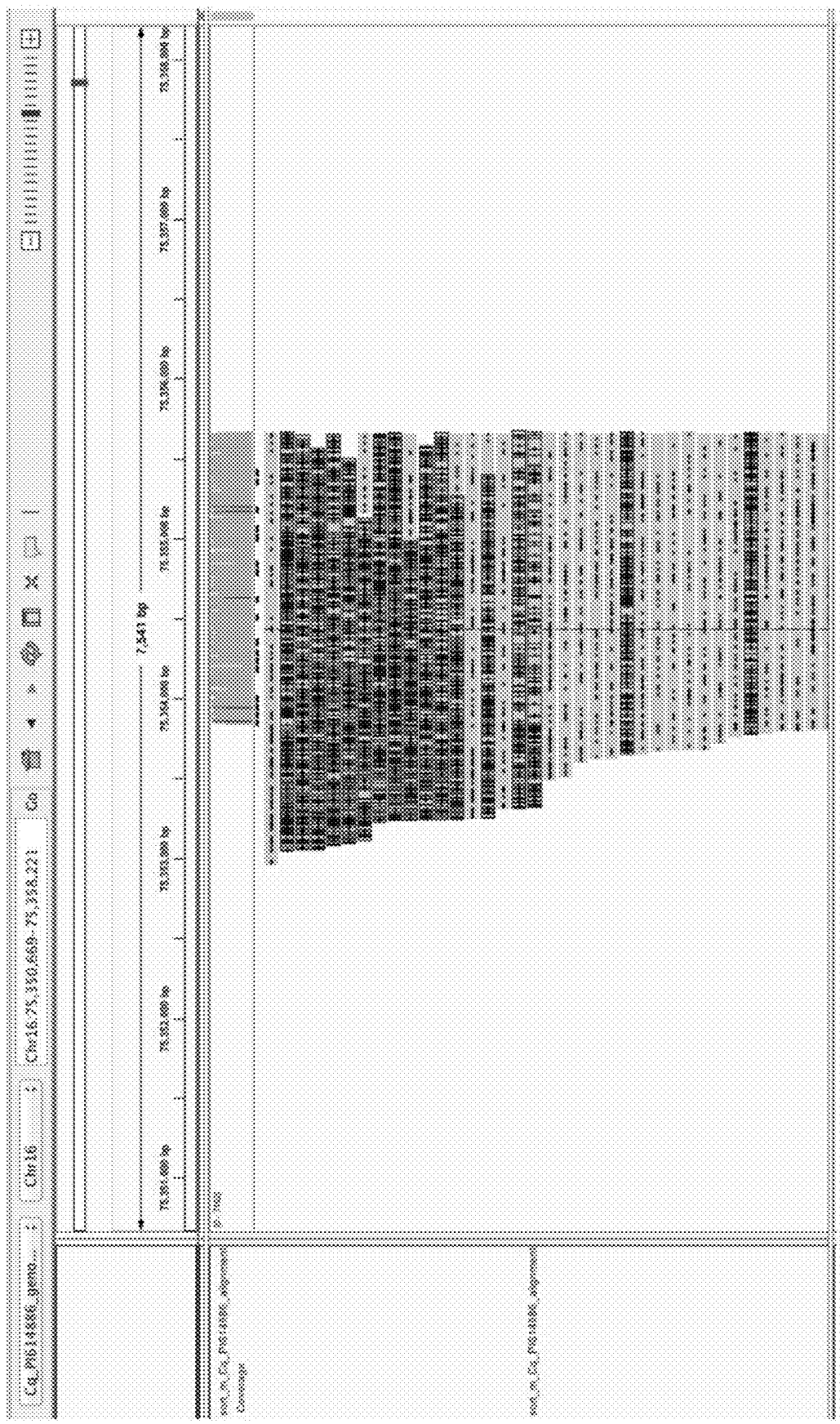

FIG. 37 shows the results of analysis of a transformant using a next-generation sequencer. The introduction of the gene of interest into the *quinoa* genome was recognized.

Figure 38:
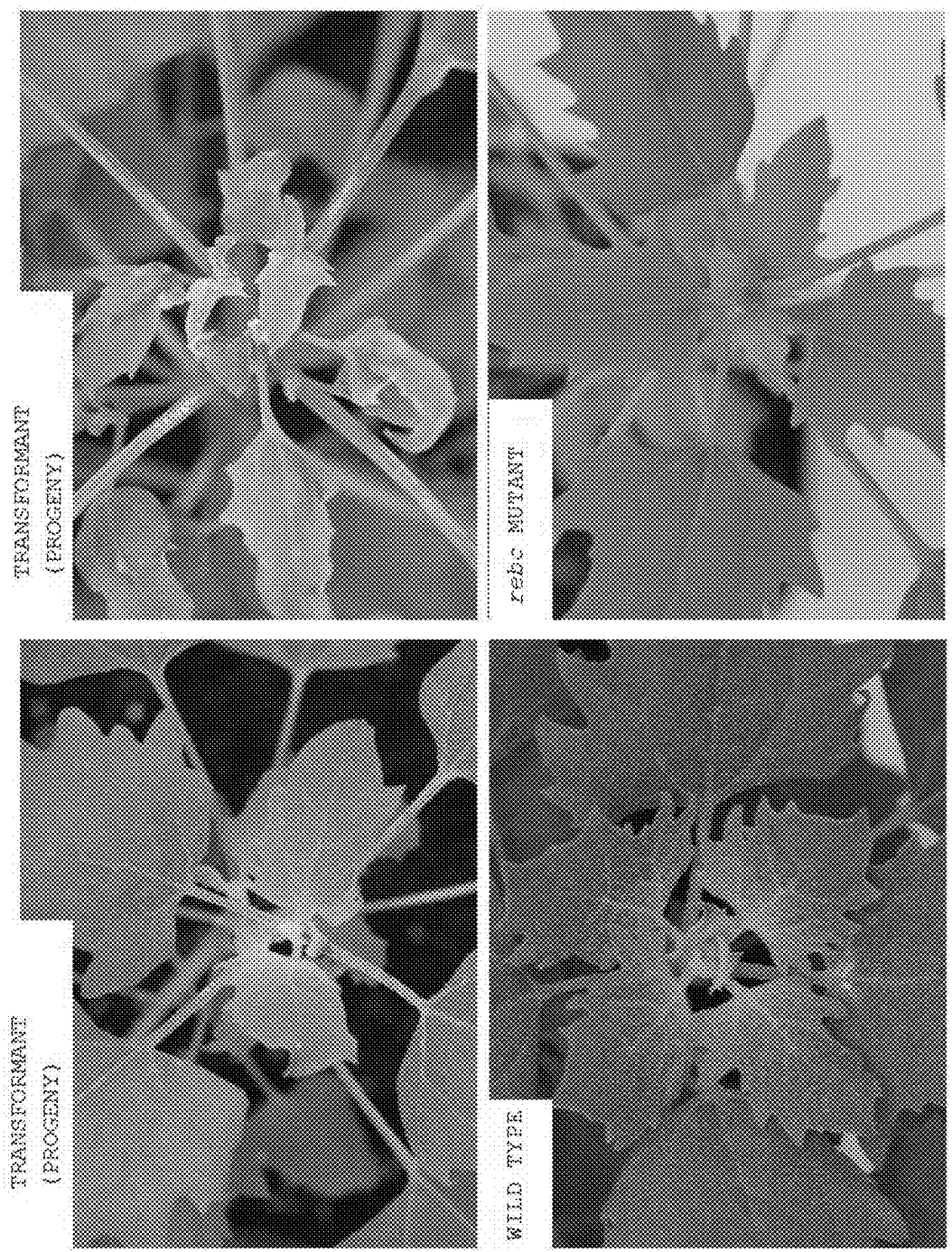

FIG. 38 shows the results of an investigation of the phenotypes of transformant progeny. The upper panels show transformants (progeny), and the lower panels show the wild type and the rebc mutant. The transformed progeny of the upper left panel was of the wild type having bladders (with the introduced gene), and the transformed progeny of the upper right panel was of the rebc mutant type (without the introduced gene). It was recognized that the phenotype of the transformant was inherited.

DESCRIPTION OF EMBODIMENTS

A method of producing a transformed plant (floral dip/cutting-sealing method) of the present invention is a method aimed at: (1) facilitating infection with an *Agrobacterium* by cutting a plant body; (2) installing the plant body, for example, in a sealed container to keep a high-humidity condition, the high humidity enhancing the growth/proliferation of the *Agrobacterium*, to thereby facilitate infection with the *Agrobacterium*; and (3) placing the plant body under a dark condition to reduce its resistance to the *Agrobacterium* and growth, thereby facilitating infection with the *Agrobacterium*, and to suppress damage to the cut plant body by light. That is, the method and its steps cannot be particularly limited as long as any one, two, or all of (1) to (3) can be carried out.

[Method of Producing Transformed Plant of the Present Invention]

The method of producing a transformed plant of the present invention encompasses any one or more of the following.

(Floral Dip/Cutting-Sealing Method)

A method of producing a transformed plant, a seed of the plant, or a callus of the plant, the method including the following steps:

(1-1) a step of bringing an *Agrobacterium* transformed with an expression vector carrying a gene of interest, or the gene of interest and a drug resistance gene, under control of a promoter capable of inducing expression of the gene of interest in a plant body into contact with a target plant body to inoculate the *Agrobacterium* thereinto;

(1-2) a step of cutting the plant body; and (1-3) a step of placing the cut plant body including a site having introduced therein the gene of interest under high-humidity and dark conditions to obtain a plant body having introduced therein the gene of interest;

or (2-1) a step of bringing an *Agrobacterium* transformed with an expression vector carrying a gene of interest, or the gene of interest and a drug resistance gene, under control of a promoter capable of inducing expression of the gene of interest in a plant body into contact with a target plant body to inoculate the *Agrobacterium* thereinto;

(2-2) a step of cutting the plant body;

(2-3) a step of placing the cut plant body including a site having introduced therein the gene of interest under high-humidity and dark conditions; and (2-4) a step of growing the plant body until a seed is ready to be harvested, to thereby obtain a seed having introduced therein the gene of interest.

The target plant body in the step (1-1) and/or the step (2-1) is not particularly limited in terms of the number of days after its germination. Although the number of days varies depending on cultivation conditions, the number of days after the germination may be from 10 days to 100 days, or from 30 days to 60 days, and is preferably from 40 days to 50 days.

In the "bringing an *Agrobacterium* into contact to inoculate the *Agrobacterium*" in the step (1-1) and/or the step (2-1), the *Agrobacterium* is brought into contact with the target plant body to be introduced into the plant body. A method for the contact is not particularly limited, but the contact is performed by, for example, dropping a bacterial suspension obtained by suspending the *Agrobacterium* in a liquid (which is, for example, sterile water or a sucrose solution, and may contain, for example, any additive, such as Silwet L-77) onto a female organ (e.g., an ear) of the plant body, immersing the female organ of the plant body in the bacterial suspension, or spraying or applying the bacterial suspension onto the female organ of the plant body.

The *Agrobacterium* to be used may be cultured in, for example, a liquid medium, such as LB medium, to have any appropriate OD (e.g., an $O_{D600}$ of about 2.0), and collected by centrifugation before suspension.

The *Agrobacterium* in the step (1-1) and/or the step (2-1) may be further transformed with a Ti plasmid which is derived from an *Agrobacterium* strain MAFF301276 and from which a T-DNA region has been removed.

The method of producing a transformed plant may further include a step of bringing abscisic acid into contact with the target plant body before the step (1-1) and/or the step (2-1), simultaneously with the step (1-1) and/or the step (2-1), or between the step (1-1) and/or the step (2-1) and the step (1-2) and/or the step (2-2).

In the "placing the cut plant body under high-humidity and dark conditions" in the step (1-3) and/or the step (2-3), it is only required that the plant body with which the *Agrobacterium* has been brought into contact can be placed under such high-humidity and dark conditions as described below. For example, the plant body may be left to stand, installed, or stirred under such high-humidity and dark conditions as described below, and is preferably left to stand under such high-humidity and dark conditions as described below.

The high-humidity (high-humidity condition) only needs to be a humidity of 50% or more, and is preferably a humidity of from 90% to 100%.

The dark condition is not particularly limited, but is, for example, such darkness that the plant is reduced in resistance without being damaged, such as from 0 lux to 0.5 lux, from 0 lux to 1 lux, or from 0 lux to 2 lux.

A method of achieving the high-humidity and dark conditions is not particularly limited, but it is preferred that the plant body and water be installed (left to stand) in a container having low air permeability, such as a sealed container, to thereby achieve the high-humidity and dark conditions. It is more preferred that the plant body (which may include a flowerpot, soil, a fertilizer, and the like) be installed in a sealed container, and that the sealed container be filled with 5 mL to 5,000 mL, 10 mL to 2,000 mL, 50 mL to 1,000 mL, 100 mL to 1,000 mL, or 500 ml to 1,000 mL of water.

The sealed container is not particularly limited as long as the inside of the container can be kept at a humidity of from 90% to 100% and can be made a dark place, but an example thereof is a container sealed with a rubber seal, such as Mippail (Fuji System Pack).

A temperature at which the plant body is placed under the high-humidity and dark conditions is not particularly limited as long as the plant can survive at the temperature, but is preferably from 15° C. to 30° C., more preferably from 20° C. to 25° C., most preferably about 22° C.

A period of time for which the plant body is placed under the high-humidity and dark conditions is not particularly limited, but may be from 1 hour to 2 weeks, or from 12 hours to 1 week, and is preferably from 1 day to 6 days, more preferably from 1 day to 5 days, still more preferably from 1 day to 4 days.

The method of producing a transformed plant of the present invention may further include a "step of growing the plant body under any appropriate conditions" between the step (1-1) and the step (1-2) or between the step (2-1) and the step (2-2). The "growing the plant body under any appropriate conditions" is not particularly limited as long as the plant body can be grown until the gene of interest is expressed, but it is preferred that the plant body be grown until the plant body buds.

A temperature condition for the growing is not particularly limited as long as the plant can survive at the temperature, but is preferably from 15° C. to 30° C., more preferably from 20° C. to 25° C., most preferably about 22° C.

Light and dark conditions for the growing are not particularly limited as long as the plant can survive. For example, the light and dark conditions may be 8- to 16-h light/16-to 8-h dark conditions, or 9- to 13-h light/15-to 11-h dark conditions, and are preferably 11-h light/13-h dark conditions.

The "step of cutting the plant body" in the step (1-2) and/or the step (2-2) is not particularly limited, but it is preferred that the plant body be cut so as to include a site having introduced therein the gene of interest and/or a female organ (e.g., an ear). As a method of cutting the plant body so as to include a site having introduced therein the gene of interest and/or a female organ (e.g., an ear), for example, the plant body may be cut near the center of its stalk, and it is preferred that the plant body be cut so as to include 8 cm to 15 cm from the tip of its stalk (shoot apex).

The "growing the plant body until a seed is ready to be harvested" in the step (2-4) is not particularly limited as long as the plant body can be grown until a seed is ready to be harvested, but desirably includes a step of pollinating the plant body from the viewpoint of increasing the number of seeds to be obtained. The pollination encompasses self-pollination and cross-pollination, and is preferably cross-pollination.

A temperature condition for the growing is not particularly limited as long as a temperature at which the plant body can be grown until a seed is ready to be harvested is adopted, but the temperature is preferably from 15° C. to 30° C., more preferably from 20° C. to 25° C., most preferably about 22° C.

Light and dark conditions for the growing are not particularly limited as long as the plant body can be grown until a seed is ready to be harvested. For example, the light and dark conditions may be 8- to 16-h light/16-to 8-h dark conditions, or 9- to 13-h light/15-to 11-h dark conditions, and are preferably 11-h light/13-h dark conditions.

The "seed having introduced therein the gene of interest" in the step (2-4) is not particularly limited as long as the seed has a nucleic acid molecule containing the base sequence of the gene of interest in its cells, preferably in its genome, but the seed contains a homozygote and/or a heterozygote of the gene of interest.

The method of producing a transformed plant of the present invention may include a step of selecting a seed containing a homozygote of the gene of interest from the "seeds having introduced therein the gene of interest" after the step (2-4).

(Floral Dip/Non-Cutting-Sealing Method 1)

A method of producing a transformed plant, including the following step:

(1) a step of bringing an *Agrobacterium* strain MAFF311303 transformed with an expression vector carrying a gene of interest, or the gene of interest and a drug resistance gene, under control of a promoter capable of inducing expression of the gene of interest in a plant body and with a Ti plasmid which is derived from an *Agrobacterium* strain MAFF301276 and from which a T-DNA region has been removed into contact with a target plant body to inoculate the bacterium thereinto.

(Floral Dip/Non-Cutting-Sealing Method 2)

A method of producing a transformed plant, including the following steps:

(1) a step of bringing an *Agrobacterium* transformed with an expression vector carrying a gene of interest, or the gene of interest and a drug resistance gene, under control of a promoter capable of inducing expression of the gene of interest in a plant body into contact with a target plant body to inoculate the bacterium thereinto; and (2) a step of bringing abscisic acid into contact with the target plant body before the step (1), simultaneously with the step (1), or after the step (1).

(Floral Dip/Non-Cutting-Sealing Method 3)

A method of producing a transformed plant, including the following steps:

(1) a step of bringing an *Agrobacterium* strain MAFF311303 transformed with an expression vector carrying a gene of interest, or the gene of interest and a drug resistance gene, under control of a promoter capable of inducing expression of the gene of interest in a plant body and with a Ti plasmid which is derived from an *Agrobacterium* strain MAFF301276 and from which a T-DNA region has been removed into contact with a target plant body to inoculate the bacterium thereinto; and (2) a step of bringing abscisic acid into contact with the target plant body before the step (1), simultaneously with the step (1), or after the step (1).

[Transformation Agent and Transformation Aid of the Present Invention]

The present invention encompasses the following transformation agent.

A transformation agent, including an *Agrobacterium* strain MAFF311303 transformed with:

a Ti plasmid which is derived from an *Agrobacterium* strain MAFF301276 and from which a T-DNA region has been removed; and an expression vector carrying a gene of interest and a drug resistance gene under control of a promoter capable of inducing expression of the gene of interest in a plant body.

The present invention also encompasses a plant transformation aid using an *Agrobacterium*, including abscisic acid.

The plant transformation aid using an *Agrobacterium*, including abscisic acid, may be used in a plant transformation method involving using an *Agrobacterium* (e.g., the floral dip method). Its mode of use is not particularly limited, but the plant transformation aid including abscisic acid may be used by being brought into contact with the target plant body before, simultaneously with, or after a step of bringing the *Agrobacterium* into contact with a target plant body to inoculate the bacterium thereinto. For example, transformation may be performed in the following manner: a suspension containing the *Agrobacterium* having a gene of interest is mixed with the plant transformation aid including abscisic acid, and the mixed liquid is brought into contact with, or applied or sprayed onto the plant body to be transformed.

(Promoter Capable of Inducing Expression of Gene of Interest in Plant Body)

The promoter capable of inducing expression of the gene of interest in a plant body is not particularly limited, but examples thereof include a CaMV 35S promoter, an *Agrobacterium*-derived promoter (e.g., a Nos (Nopaline synthase) promoter), a drug-inducible promoter (e.g., an alcohol dehydrogenase (alcA) promoter or a UAS promoter), and a plant gene promoter (e.g., ubiquitin promoter). Of those, a CaMV 35S promoter is preferred.

(Gene of Interest)

The gene of interest is not particularly limited as long as the gene can be expressed in a plant cell. Examples thereof include useful genes including: an environmental stress (e.g., a salt stress) tolerance gene; a useful secondary metabolite (e.g., a betalain pigment) synthase gene; a flowering inducing gene; a plant height regulating gene; a transcription factor gene to be a transcription factor gene whose activated by ethanol; transcription is activated by an estrogen; and a transcription factor gene to be activated by dexamethasone. A useful gene may be isolated/utilized by performing, for example, genome editing, or overexpression and/or expression suppression of the gene of interest.

(Drug Resistance Gene)

The drug resistance gene is not particularly limited as long as the seed having introduced therein the gene of interest can be selected from the transformed plant, but examples thereof include a hygromycin resistance gene (hygromycin phosphotransferase; HPT), a bialaphos resistance gene (phosphinothricin N-acetyltransferase; Bar), a kanamycin resistance gene, an ampicillin resistance gene, and a tetracycline resistance gene.

(Expression Vector)

The expression vector is not particularly limited as long as the expression vector carries the promoter capable of inducing expression of the gene of interest in a plant body and the drug resistance gene. Examples thereof include pCAMBIA1301, pCAMBIA-CqCYP76AD1-1, pBIC35BP, pBI121, pER8, pTA70001, and pBICERTOMV. Of those, pCAMBIA1301 is preferred.

The expression vector carrying the gene of interest and the drug resistance gene under control of the promoter capable of inducing expression of the gene of interest in a plant body may be generated by inserting the gene of interest under control of the promoter capable of inducing expression of the gene of interest in a plant body in the expression vector.

(*Agrobacterium*)

The *Agrobacterium* has an ability to incorporate the expression vector into a plant cell. The *Agrobacterium* has an ability to incorporate the expression vector preferably into a nucleus, more preferably into a chromosome.

The *Agrobacterium* to be used in the present invention is not particularly limited, but examples thereof include *Rhizobium radiobacter* (e.g., GV3101 strain (see: Bioimpacts. 2017; 7 (4): 247-254. doi: 10.15171/bi.2017.29. Epub 2017 Sep. 18.), MAFF301276 strain, MAFF212033 strain, and MAFF311303 strain (which may be searched from the MAFF number in the NARO Genebank https://www.gene.affrc.go.jp/databases-micro_search.php)), *Rhizobium rhizogenes* (e.g., ATCC15834 strain (available in American Type Culture Collection) and MAFF211729 strain), and *Rhizobium vitis* (e.g., MAFF 663001 strain). Of those, MAFF 301276 strain and MAFF 311303 strain are preferred in the floral dip/cutting-sealing method and the floral dip/non-cutting-sealing method. In Examples to be described later, it has been recognized that MAFF301276 has an extremely higher transforming ability in *quinoa* plants than other bacterial strains, and that MAFF311303 can specifically infect only female organs despite being nonpathogenic.

In the method of producing a transformed plant of the present invention, two kinds of *Agrobacterium* strains may be used as a mixture.

The combination of two kinds of *Agrobacterium* strains is not particularly limited, but when the floral dip/cutting-sealing method is performed, in the Kd variety, combinations of the GV3301 strain and the ATCC15834 strain, the GV3301 strain and the MAFF211729 strain, the GV3301 strain and the MAFF663001 strain, the MAFF212033 strain and the MAFF311303 strain, and the MAFF311303 strain and the MAFF211729 strain are preferred, and in the mutant ghy or the mutant ghy/rebc, combinations of the GV3301 strain and the MAFF311303 strain, the MAFF301276 strain and the MAFF311303 strain, the MAFF311303 strain and the MAFF211729 strain, and the MAFF211729 strain and the MAFF663001 strain are preferred.

(Target Plant Body)

The target plant body for which the method of producing a transformed plant of the present invention and the transformation agent of the present invention are used is not particularly limited. Examples thereof include angiosperms, gymnosperms, dicotyledons, monocotyledons, amaranthaceous plants, poaceous plants, *Chenopodium* plants, *quinoa* (*Chenopodium quinoa*), rice, barley, wheat, spinach, beet, *Arabidopsis, Amaranthus, Chenopodium album*, and *Medicago truncatula*. Of those, angiosperms are preferred, and *quinoa* is more preferred.

The *quinoa* is not particularly limited, but may be any of the following: the Kd variety, an 85 variety, a 108 variety, a green hypocotyl mutant (ghy) (Imamura T, Takagi H, Miyazato A, Ohki S, Mizukoshi H, and Mori M (2018) Biochemical and Biophysical Research Communications 496 (2): 280-286), a reduced epidermal bladder cells 1 mutant (rebc: mutant of the REBC gene, which encodes a protein (Acc. No. XP_021715187) having a full length of 482 amino acid residues and having a WD40 domain in the region of residues 139 to 432, in which guanine (G) at position 1,139 of the gene has been changed to adenine (A) to change tryptophan (Trp) at amino acid 380 to a STOP), and a mutant ghy/rebc obtained by crossbreeding ghy and the mutant rebc. Of those, the mutant ghy or the mutant ghy/rebc is preferred.

(Ti Plasmid which is Derived from *Agrobacterium* Strain MAFF301276 and from which T-DNA Region has been Removed)

The Ti plasmid which is derived from the *Agrobacterium* strain MAFF301276 and from which a T-DNA region has been removed is not particularly limited as long as the T-DNA region has been removed.

EXAMPLES

The present invention is hereinafter described in detail by way of specific examples. However, the present invention is not limited to the examples.

[Plant Materials]

The Kd variety of *quinoa* used in Examples of the present invention was obtained from Kyoto University, and the 85 variety and the 108 variety were obtained from the U.S. Department of Agriculture (USDA) (Independence Avenue, Washington DC, USA). In addition, EMS-mutagenized seeds (M1) derived from the 108 variety were grown until an M3 generation was obtained, and green hypocotyl (ghy) (Imamura T, Takagi H, Miyazato A, Ohki S, Mizukoshi H, and Mori M (2018) Biochemical and Biophysical Research Communications 496 (2): 280-286) and reduced epidermal bladder cells (rebc) were obtained therefrom. Further, the mutant ghy and the mutant rebc were crossbred to produce ghy/rebc (FIG. 2 to FIG. 5).

[Bacterial Strains and Plasmids]

Bacterial strains used in experiments were the following seven bacterial strains: *Rhizobium radiobacter* (GV3101 strain, MAFF301276 strain, MAFF212033 strain, and MAFF311303 strain), *Rhizobium rhizogenes* (ATCC15834 strain and MAFF211729 strain), and *Rhizobium vitis* (MAFF663001 strain) (Table 1). The MAFF301276 strain, the MAFF212033 strain, the MAFF311303 strain, the MAFF211729 strain, and the MAFF663001 strain, which were newly used in Examples of the present invention, are wild-type strains from Japan obtained from the NARO Genebank (Tsukuba, Japan).

A binary vector pBIC35BP (Mori M, Kaindo M, Okuno T, and Frusawa I (1993) Federation Biochemical Societies 336 (1): 171-174) harbors a bialaphos resistance gene (phosphinothricin N-acetyltransferase; Bar) under control of the 35S promoter of cauliflower mosaic virus (CaMV), a binary vector pCAMBIA1301 harbors an intron-gusA gene (β-glucuronidase; GUS) (Jefferson R A, Kavanagh T A, and Bevan M W (1987) The EMBO Journal 6 (13): 3901-3907) and a hygromycin resistance gene (hygromycin phosphotransferase; HPT) under control of the CaMV 35S promoter, and a binary vector pCAMBIA-CqCYP76AD1-1 harbors a betalain pigment synthesis-related gene CqCYP76AD1-1 under control of the CaMV 35S promoter (FIG. 6) (Imamura T, Takagi H, Miyazato A, Ohki S, Mizukoshi H, and Mori M (2018) Biochemical and Biophysical Research Communications 496 (2): 280-286). The MAFF301276 strain was transformed with the binary vector pCAMBIA1301 and the binary vector pCAMBIA-CqCYP76AD1-1, and the other six bacterial strains were transformed with the binary vector pCAMBIA1301 by a triparental mating method (Wise A A, Liu Z, and Binns A N (2006) Methods in Molecular Biology 343:43-53) before use in infection experiments.

TABLE 1

| Bacterial strain name | Scientific name (pathogenicity type) |
| --- | --- |
| GV3101 | *Rhizobium radiobacter* (Ti) |
| ATCC15834 | *Rhizobium rhizogenes* (Ri) |
| MAFF301276 | *Rhizobium radiobacter* (Ti) |
| MAFF212033 | *Rhizobium radiobacter* (Ri) |
| MAFF311303 | *Rhizobium radiobacter* (nonpathogenic) |
| MAFF211729 | *Rhizobium rhizogenes* (Ti) |
| MAFF663001 | *Rhizobium vitis* (Ti) |

List of bacterial strains used in Examples of the present invention. Five bacterial strains excluding the GV3101 strain and the ATCC15834 strain are wild-type strains from Japan. (Ti) means carrying a Ti plasmid, and (Ri) means carrying an Ri plasmid. In addition, (nonpasogenic) means being nonpathogenic.

[Experiment Using Tissue Culture Technology] (Growing of Aseptic *Quinoa* Plant Body)

*Quinoa* seeds (about 10 seeds) were placed in 1 mL of a sterilizing solution (20 ml/L Plant Preservative Mixture; PPM (Plant Cell Technology, Jefferson, Washington DC, USA), 20 ml/L Tween 20, 1 ml/L 1 M MgCl2), and were stirred for 6 hours using Petite Rotor (WakenBtech Co., Ltd., Kyoto, Japan) (using a 1.5 mL Eppendorf tube). After that, the sterilizing solution in the tube was removed, 500 μL of a sterilizing solution having the same composition was added, and the seeds were washed by being stirred using a pipette. After a similar operation had been performed once, the seeds were plated in a germination medium in a clean bench (Table 2). Then, the seeds were grown at 20° C. under 8-h light/16-h dark conditions.

TABLE 2

| | | | | Transformed callus experiment | | | Redifferentiation medium | | Gall formation experiment | |
| --- | --- | --- | --- | --- | --- | --- | --- | --- | --- | --- |
| | | | Germination | Callus induction | Co-culture | Callus induction/selection | G1 | G2 | Co-culture | Gall induction |
| Sucrose (g/L) | | | 15 | 30 | 30 | 30 | 30 | 30 | 30 | 30 |
| Gelrite (mg/L) | | | 2.5 | 3.2 | 3.2 | 3.2 | 3.2 | 3.2 | 2.5 | 2.5 |
| Acetosyringone (mg/L) | | | | | 10 | | | | 10 | |
| Plant hormone (mg/L) | 2,4-D*[1] | | | 1 | 1 | 1 | 0.01 | 0.01 | | |
| | Kinetin | | | 2 | 2 | 2 | | | | |
| | Benzyladenine | | | | | | 1 | 1 | | |
| | Gibberellin | | | | | | [1] | [2] | | |
| Antibiotic (mg/L) | Carbenicillin | | 100 | 100 | | 100 | 100 | 100 | | 100 |
| | Hygromycin | | | | | 40 | | | | |

Medium composition. *1 represents 2,4-dichlorophenoxyacetic acid. MS medium was used as a base. The pH was adjusted to 5.9. Liquid medium was not supplemented with Gelrite.

(Induction of Gall Formation with *Agrobacterium*)

A bacterial strain used in the experiment was streaked on LB solid medium supplemented with 100 mg/L kanamycin and 100 mg/L hygromycin, and was cultured at 26° C. under a 24-h dark condition for 2 days (Table 3). The proliferated bacteria were transferred to 50 mL of LB liquid medium supplemented with 100 mg/L kanamycin and 100 mg/L hygromycin (using a 300 mL Erlenmeyer flask) through use of a platinum loop, and were cultured using a shaking thermostatic water bath BW201 (Yamato Scientific Co., Ltd., Tokyo, Japan) under the conditions of 26° C., about 24 hours, and about 130 rpm (Table 2). After the culture, the bacterial culture suspension (OD600=about 2.0) was transferred to a 50 ML conical tube, and centrifuged using Mx-301 Highspeed Refrigerated Micro Centrifuge (Tomy Seiko Co., Ltd., Tokyo, Japan) (10 minutes, 60,000 rpm). The supernatant was discarded, followed by addition of 10 mL of sterile water and resuspension using VORTEX-GENIE 2 (Scientific Industries, Bohemia, NY, USA) to produce a bacterial suspension. 1.6 mL of the bacterial suspension and *quinoa* at 3 days after seeding that had been grown under an aseptic state were placed in a plastic Petri dish, and the *quinoa* was cut at the center of its hypocotyl with a scalpel while being dipped in the bacterial suspension. After the cutting, the infected *quinoa* was plated in the co-culture medium, and co-cultured at 20° C. under a 24-h dark condition for 4 days (Table 2). The co-cultured *quinoa* was placed in a 300 mL beaker containing a washing solution obtained by adding 100 mg/L carbenicillin to sterile water, and was washed while being lightly shaken. The washing solution was changed to a fresh one, and a similar washing operation was further performed twice. After the washing, the washing solution adhering to the *quinoa* was removed through sterile filter paper, and the *quinoa* was plated in the gall induction medium (Table 2). After that, culture was performed at 20° C. under 8-h light/16-h dark conditions.

TABLE 3

| LB | |
|---|---|
| Tryptophan (g/L) | 10 |
| Dried yeast extract (g/L) | 5 |
| Sodium chloride (g/L) | 5 |
| Sodium hydroxide (mL/L) | 1.5 |
| Agarose (g/L) | 15 |

LB medium composition list. Liquid medium was not supplemented with agarose.

(Transformed Callus Experiment)

A bacterial strain used in the experiment was streaked on LB solid medium supplemented with 100 mg/L antibiotics (kanamycin and bialaphos for the culture of a bacterial strain harboring the binary vector pBIC35BP, and kanamycin and hygromycin for the culture of a bacterial strain harboring the binary vector pCAMBIA1301), and was cultured at 26° C. under a 24-h dark condition for 2 days (Table 3). The proliferated bacteria were scraped with a dispensing spoon, and transferred to 50 mL of the liquid co-culture medium (in a 100 mL Erlenmeyer flask) (Table 2). After the transfer, culture was performed using a shaking thermostatic water bath BW201 under the conditions of 26° C., about 30 minutes, and about 120 rpm. 4 mL of the bacterial culture suspension (OD600=about 0.2) was placed in a plant culture test tube, and an aseptic *quinoa* section was infected therein for 2 minutes. The excess bacterial culture suspension adhering to the hypocotyl section was removed using sterile filter paper, and the section was plated in the co-culture solid medium (Table 2). After the plating, culture was performed at 20° C. under a 24-h dark condition for 2 days. The co-cultured section was placed in a plant culture test tube containing about 10 mL of a washing solution obtained by adding 100 mg/L carbenicillin to sterile water, and was washed while being stirred with P1000 Pipetman (Gilson, Manhattan, NY, USA). The washing solution was changed to a fresh one, and a similar washing operation was further performed once. After the washing, the washing solution adhering to the section was removed through sterile filter paper, and the section was plated in the callus induction/selection medium (Table 2). After that, the section was cultured at 20° C. under 8-h light/16-h dark conditions, and transferred to fresh medium every 3 weeks. (This technique was a partially modified version of Ohtani's sweet potato transformation method described in Protocols for Plant Transformation (Yutaka Tabei (2012) Transformation Protocols. Kagaku-Dojin Publishing Company, Inc., pp. 71-78).)

(Recognition of gusA by GUS Staining)

In order to recognize the expression of the GUS gene, an infected *quinoa* seedling section ("Induction of Gall Formation with *Agrobacterium*") or an induced callus (see "Transformed Callus Experiment") was immersed in a 5-bromo-4-chloro-3-indolyl-β-D-glucuronidecyclohexylamine salt (X-Gluc) staining solution (Jefferson R A, Kavanagh T A, and Bevan M W (1987) The EMBO Journal 6 (13): 3901-3907) (Table 4). At this time, vacuum infiltration was performed so that the staining solution entered between tissues. After that, culture was performed at 37° C. under a 24-h dark condition. After the culture, the staining solution was removed, followed by immersion in 70% ethanol.

TABLE 4

| GUS staining solution (ml/L) | |
|---|---|
| 20 mg/L X-Gluck*[1] (using DMF*[2] as diluent) | 50 |
| 10 mM EDTA | 20 |
| 12.5 mM [Fe(CN)$_6$]$^{3-}$*[3] | 40 |
| 12.5 mM [Fe(CN)$_6$]$^{4-}$*[4] | 40 |
| Triton X-100 | 3 |
| 1M phosphate buffer pH 7.4 | 100 |
| Methanol | 200 |

X-Gluc staining solution composition. *1 represents 5-bromo-4-chloro-3-indolyl-β-D-glucuronide, *2 represents N,N-dimethylformamide, *3 represents potassium ferricyanide, and *4 represents potassium ferrocyanide.

[Experiment using Floral Dip Method]

(Growing of *Quinoa*)

Seeds were sown in sowing soil (Takii & Co., Ltd., Kyoto, Japan) (using a 200-cell tray), followed by growth in a plant culture chamber at 22° C. under 11-h light/13-h dark conditions.

(Bacterial Inoculation Experiment on *Quinoa* Ear Using Floral Dip Method)

Bacteria used in the experiment were streaked on LB solid medium supplemented with 100 mg/L kanamycin and 100 mg/L hygromycin, and was cultured at 26° C. under a 24-h dark condition for 2 days (Table 3). The proliferated bacteria were transferred to 50 mL of LB liquid medium supplemented with 100 mg/L kanamycin and 100 mg/L hygromycin (in a 300 mL Erlenmeyer flask), and were cultured using a shaking thermostatic water bath BW201 under the conditions of 26° C., about 24 hours, and about 130 rpm. After the culture, the bacterial culture suspension (OD600=about 2.0) was transferred to a 50 mL conical tube, and centrifuged using Mx-301 Highspeed Refrigerated Micro Centrifuge (10 minutes, 60,000 rpm). The supernatant was discarded, followed by addition of 20 mL of a 5% (w/v) sucrose solution containing Silwet L-77 and resuspension using VORTEX-GENIE 2 to produce a bacterial suspension (results shown in Example 1 and results shown in Example 3 were obtained by inoculation experiments using Silwet L-77 at 0.02% (v/v) and 0.04% (v/v), respectively). At the time of inoculation with the bacterial suspension, *quinoa* to be used was placed in a sealed container (Mippail (Fuji System Pack, Tokyo, Japan)) filled with water, and the bacterial suspension was dropped onto an ear using P200 Pipetman (Gilson, Manhattan, NY, USA). After the inoculation, the lid of the sealed container was closed to establish a dark condition, and the container was left to stand in a plant culture chamber at 22° C. for 2 days. After that, the *quinoa* was grown in the plant culture chamber at 22° C. under 11-h light/13-h dark conditions.

(Cutting and Sealing Treatment of Ear Inoculated with Bacterium)

At 2 weeks after bacterial inoculation, the *quinoa* was cut near the center of its hypocotyl. After the cutting, the *quinoa* was placed in a Petri dish or a Tupperware container, a gap in the container was covered with a plastic tape, and the container was placed under a high-humidity condition for 3 days. After that, the *quinoa* was put in a plastic pot for seedling growth (6 cm) containing Ikubyou Baido (Takii & Co., Ltd.), and was grown at 22° C. under 11-h light/13-h dark conditions until seeds were ready to be harvested.

(Measurement of Ratio of GUS-expressing Individuals)

In the case of cutting-sealing treatment (−), *quinoa* at 2 weeks after inoculation treatment was subjected to GUS staining by the same procedure as in "Recognition of gusA by GUS Staining" above. In the case of cutting-sealing treatment (+), *quinoa* at 2 weeks after inoculation treatment was subjected to cutting-sealing treatment (see "Cutting and Sealing Treatment of Ear Inoculated with Bacterium"), and then subjected to GUS staining by the same procedure as in "Recognition of gusA by GUS Staining." After the GUS staining and decolorization treatment, the number of individuals found to exhibit expression was measured. "One individual exhibiting GUS expression" was defined as an individual exhibiting GUS expression at one or more places on its ear, or in the case of female organs, an individual having one or more female organs each exhibiting GUS expression over the entire organ, and GUS staining ratios were measured in ears and female organs (FIG. 1). The measurement of GUS expression in female organs was performed using a stereoscopic microscope Stemi 2000-C (Carl Zeiss, Jena, Germany).

[Analysis of Bacterium and Gall]
(Gall Induction)

Figure 6:
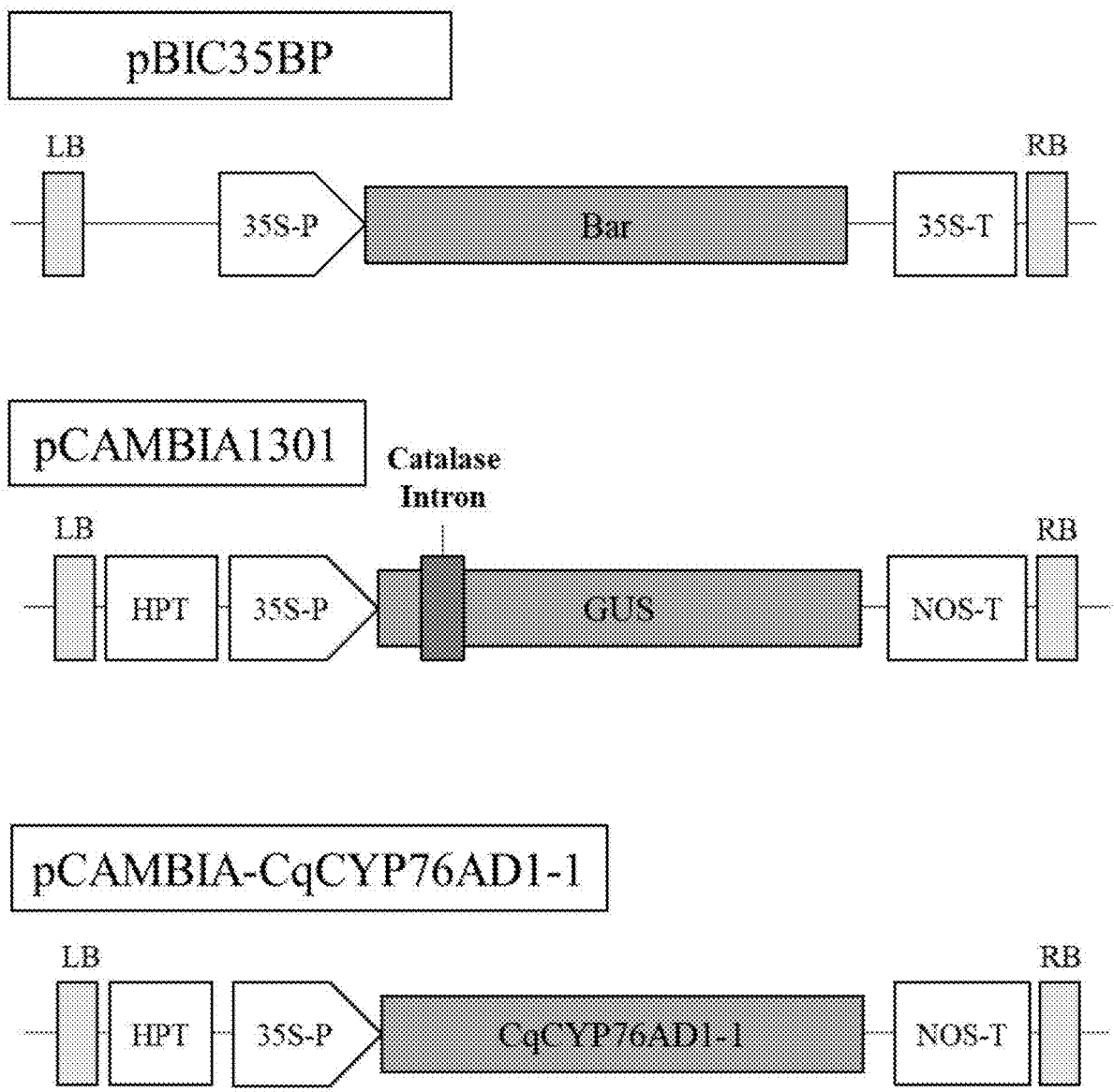
FIG. 6 is a list of vectors used in Examples of the present invention. Bar: bialaphos resistance gene, Gus: β-glucuronidase gene, CqCYP76AD1-1: *quinoa* betalain synthesis-related gene, HPT: hygromycin resistance gene, 35S-P: CaMV 35S promoter, 35S-T: CaMV 35S terminator, NOS-T: NOS terminator, RB: right border, LB: left border.

A transformed strain was produced by introducing the binary vector pCAMBIA1301 or the binary vector pCAMBIA-CqCYP76AD1-1 into the MAFF301276 strain (FIG. 6). Those bacteria were streaked on LB solid medium supplemented with 100 mg/L kanamycin and 100 mg/L hygromycin, and were cultured at 26° C. under a 24-h dark condition for 2 days (Table 3). The proliferated bacteria were transferred to 50 mL of LB liquid medium supplemented with 100 mg/L kanamycin and 100 mg/L hygromycin (using a 300 mL Erlenmeyer flask), and were cultured using a shaking thermostatic water bath BW201 under the conditions of 26° C., about 24 hours, and about 130 rpm. Then, the bacterial culture suspension (OD600=about 2.0) was transferred to a 50 ml conical tube, and centrifuged using Mx-301 Highspeed Refrigerated Micro Centrifuge (10 minutes, 60,000 rpm). The supernatant was discarded, followed by addition of 10 mL of the liquid co-culture medium and resuspension using VORTEX-GENIE 2 to produce a bacterial suspension (Table 2). 1.6 mL of the bacterial suspension and *quinoa* at 7 days after seeding that had been grown under an aseptic state were placed in a plastic Petri dish, and the *quinoa* was cut at the center of its hypocotyl with a scalpel while being dipped in the bacterial suspension. After the cutting, operations similar to those of "Induction of Gall Formation with *Agrobacterium*" were performed.

(DNA Extraction from *Agrobacterium* Strain MAFF301276 and Gall Formed in *Quinoa*)

DNA was extracted from the MAFF301276 strain and a gall induced by the experiment of 3.5.1 through use of DNeasy Plant Mini Kit (QIAGEN, Valencia, CA, USA) in accordance with the attached protocol.

(Analyses of Base Sequence by MinION and Sanger Sequencing)

The extracted DNA was amplified by PCR. The amplified fragment was purified using ExoSAP-IT Express PCR Cleanup Reagents (Thermo Fisher Scientific, Waltham, MA, USA) in accordance with the attached protocol. The purified fragment was used as template DNA, and a sample was adjusted using BigDye Terminator v3.1 Cycle Sequencing Kit (Thermo Fisher Scientific) and subjected to PCR under the following conditions: 96° C./1 minute, followed by 35 cycles of 96° C./10 seconds, 50° C./10 seconds, and 60° C./2.5 minutes. After sequencing reaction, the sample was purified using ethanol and formaldehyde, and analyzed for its base sequence using ABI PRISM 3130x1 Genetic Analyzer (Applied Biosystems, Foster City, CA, USA). Further, the same DNA was subjected to analysis with MinION (Oxford Nanopore Technologies, Oxford, UK), which was commissioned to the Laboratory of Plant Gene Technology of Ishikawa Prefectural University (Lu H, Giordano F, and Ning Z (2016) Genomics Proteomics Bioinformatics 14 (5): 265-279). The results of those analyses, and Blast and Blastx (https://blast.ncbi.nlm.nih.gov/Blast.cgi) were used to analyze the presence or absence of a read carrying both of the introduced gene and the *quinoa* genome.

(PCR Analysis)

Five kinds of primers were designed (FIG. 7 and Table 5), and in order to examine the introduction of the T-DNA region of a Ti plasmid derived from the MAFF301276 strain into a *quinoa* genome region where the insertion of T-DNA was predicted by Blast (*Quinoa* genome database Contig: Cqu_c08939), PCR was performed using a thermal cycler Biometra TAdvanced (Analytik Jena, Jena, Germany) under the following conditions: initial thermal denaturation at 98.0° C./2 minutes, followed by 45 cycles of 98.0° C./10 seconds, 51.6° C./30 seconds, and 72.0° C./5 minutes.

TABLE 5

| PCR | | | Sequence (5'→3') |
|---|---|---|---|
| Set 1 (2 + 4) (Quinoa × RCq1) | Forward | GTGGATTTGTTACAAATGGGACCCG (SEQ ID NO: 1) | |
| | Reverse | GTGCTTGAGAGGAGAATGATAGCGA (SEQ ID NO: 2) | |
| Set 2 (3 + 4) (Quinoa × RCq1) | Forward | GTGGATTTGTTACAAATGGGACCCG (SEQ ID NO: 3) | |
| | Reverse | CCATACATGATCGGAGTTGGACAAG (SEQ ID NO: 4) | |
| Set 3 (1 + 2) (Quinoa genome) | Forward | TGGGGATCAGTTTTGGATGGTTAGG (SEQ ID NO: 5) | |
| | Reverse | GTGCTTGAGAGGAGAATGATAGCGA (SEQ ID NO: 6) | |
| Set 4 (2 + 5) (Quinoa × RCq1) | Forward | GACTGTCATACATCTCGAATTAGTGACT (SEQ ID NO: 7) | |
| | Reverse | GTGCTTGAGAGGAGAATGATAGCGA (SEQ ID NO: 8) | |
| Set 5 (3 + 5) (Quinoa × RCq1) | Forward | GACTGTCATACATCTCGAATTAGTGACT (SEQ ID NO: 9) | |
| | Reverse | CCATACATGATCGGAGTTGGACAAG (SEQ ID NO: 10) | |
| Set 6 (1 + 3) (Quinoa genome) | Forward | TGGGGATCAGTTTTGGATGGTTAGG (SEQ ID NO: 11) | |
| | Reverse | CCATACATGATCGGAGTTGGACAAG (SEQ ID NO: 12) | |

Figure 7:
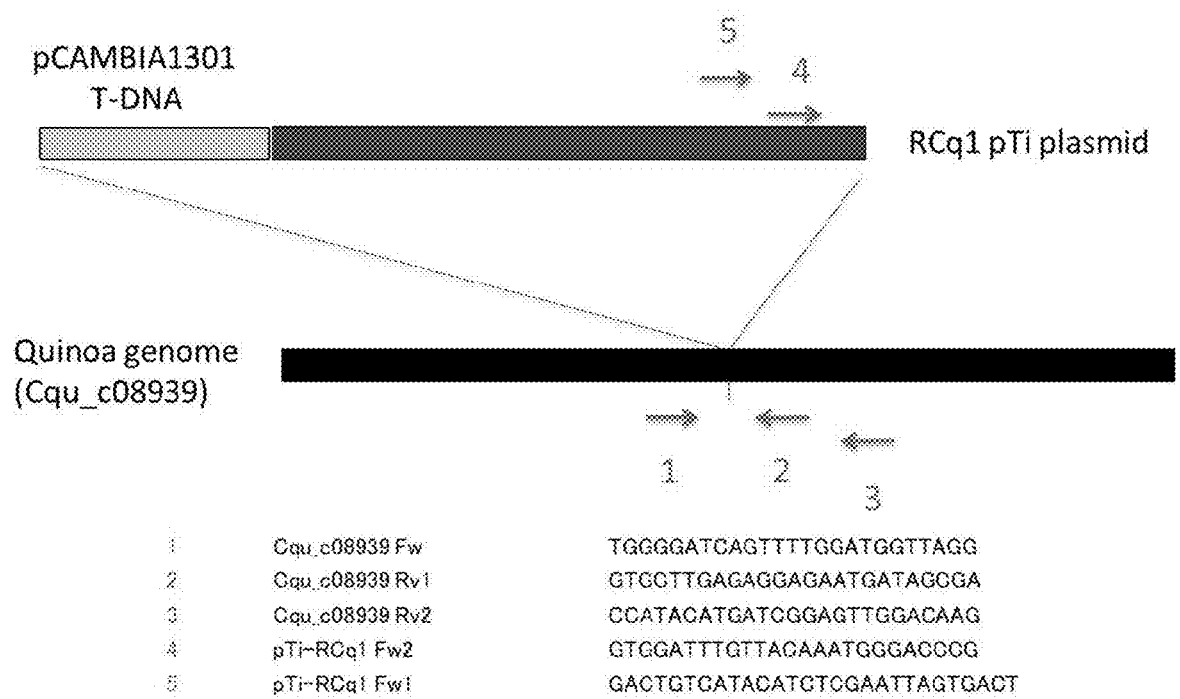
FIG. 7 is an illustration of the positions of designed primers. Arrows (1 to 5) indicate the positions of designed primers (1 to 5).

Numbers 1 to 5 in parentheses correspond to primers (1 to 5) in FIG. 7.

(Production of Bacterium Suited for Floral Dip Method in *Quinoa* and Infection Experiment)

Through utilization of the characteristics of the MAFF301276 strain and the MAFF311303 strain, a bacterial strain suited for the floral dip method was produced by the following procedure. (1) The T-DNA region is removed from the Ti plasmid carried by the MAFF301276 strain (pTiMAFF301276 strain T-DNA). (2) The Ti plasmid from which T-DNA has been removed (pTiMAFF301276 strain ΔT-DNA) is introduced into the MAFF311303 strain. (3) The binary vector pCAMBIA1301 is introduced into the MAFF311303 strain carrying the pTiMAFF301276 strain ΔT-DNA (MAFF311303pTiMAFF301276ΔT-DNA).

With use of the produced bacterial strain, a floral dip experiment on *quinoa* was performed by the procedure of "Bacterial Inoculation Experiment on *Quinoa* Ear Using Floral Dip Method." After that, GUS staining and measurement of the ratio of GUS-expressing individuals were performed by the procedure of "Measurement of Ratio of GUS-expressing Individuals."

Example 1

[Construction of Floral Dip/Cutting-Sealing Method]

A gene introduction was attempted using the floral dip method.

Figure 8:
FIG. 8 shows GUS non-expression in a *quinoa* ear subjected to a floral dip experiment (cutting-sealing treatment-).
Figure 8:
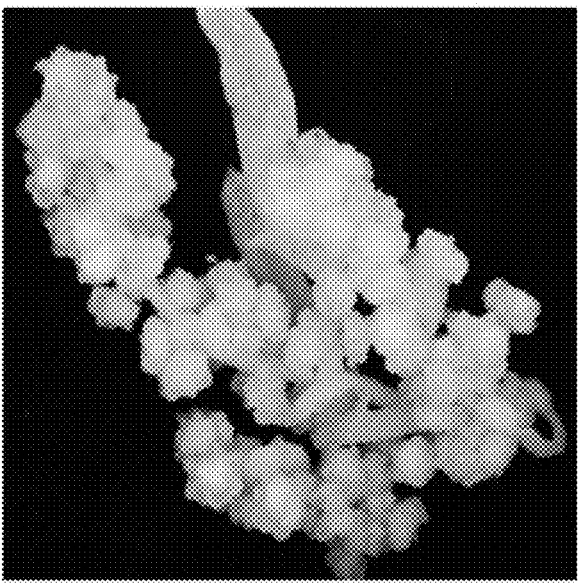
Figure 9:
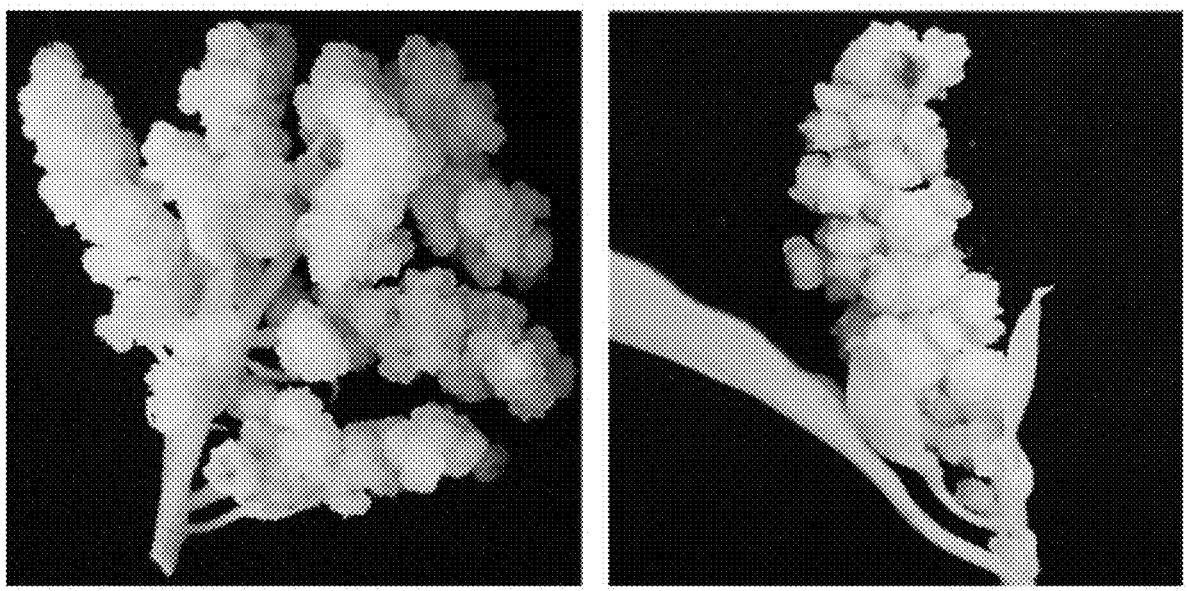
FIG. 9 shows GUS expression in a *quinoa* ear subjected to a floral dip method (cutting-sealing treatment+).
Figure 10:
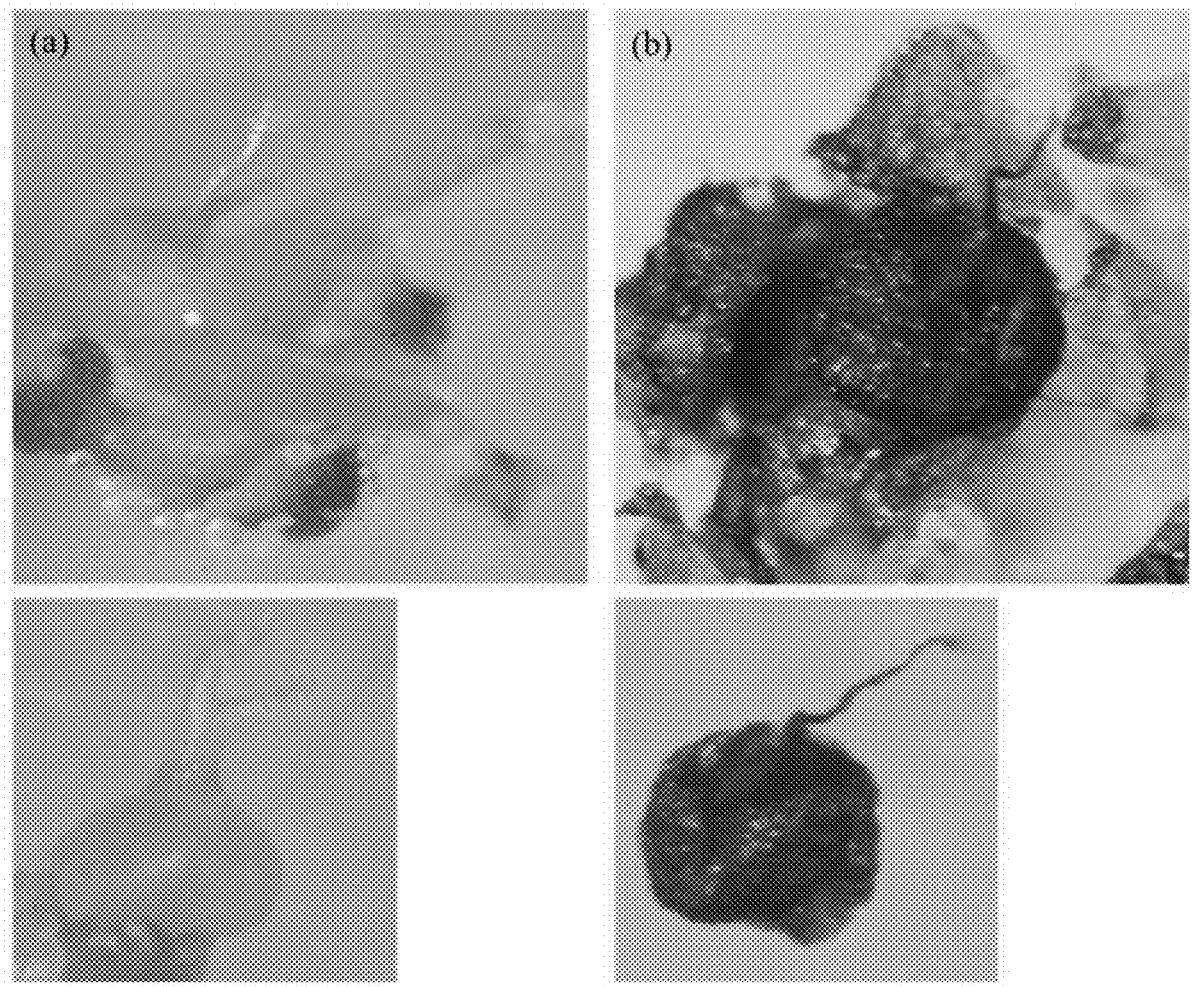
FIG. 10 show GUS expression in a female organ of the Kd variety. (a) A female organ of a non-infected individual; and (b) a female organ found to exhibit GUS expression.

With use of the GV3101 strain having introduced therein the binary vector pCAMBIA1301, an attempt was made to transform ears of the Kd variety at 30 days, 40 days, 45 days, 50 days, and 55 days after seeding with the GUS gene by the conventional floral dip method. As a result, GUS staining in the ears was not found (FIG. 8). In view of this, at 2 weeks after the inoculation treatment of the GV3101 strain, the stalk of the *quinoa* inoculated with the bacterium was cut, and subjected to high-humidity sealing treatment for 3 days. As a result, GUS expression was found in the ears of the *quinoa* subjected to the inoculation experiment at 40 days, 45 days, and 50 days after seeding (FIG. 9 and Table 6). When a stained site of the ears was dismantled, GUS staining was found in a female organ (FIG. 10). Transformation with the GUS gene by a similar method was also attempted with the MAFF301276 strain, the MAFF212033 strain, the MAFF311303 strain, ATCC15834 strain, the MAFF211729 strain, and the MAFF663001 strain, and as a result, similar results were obtained.

Figure 11:
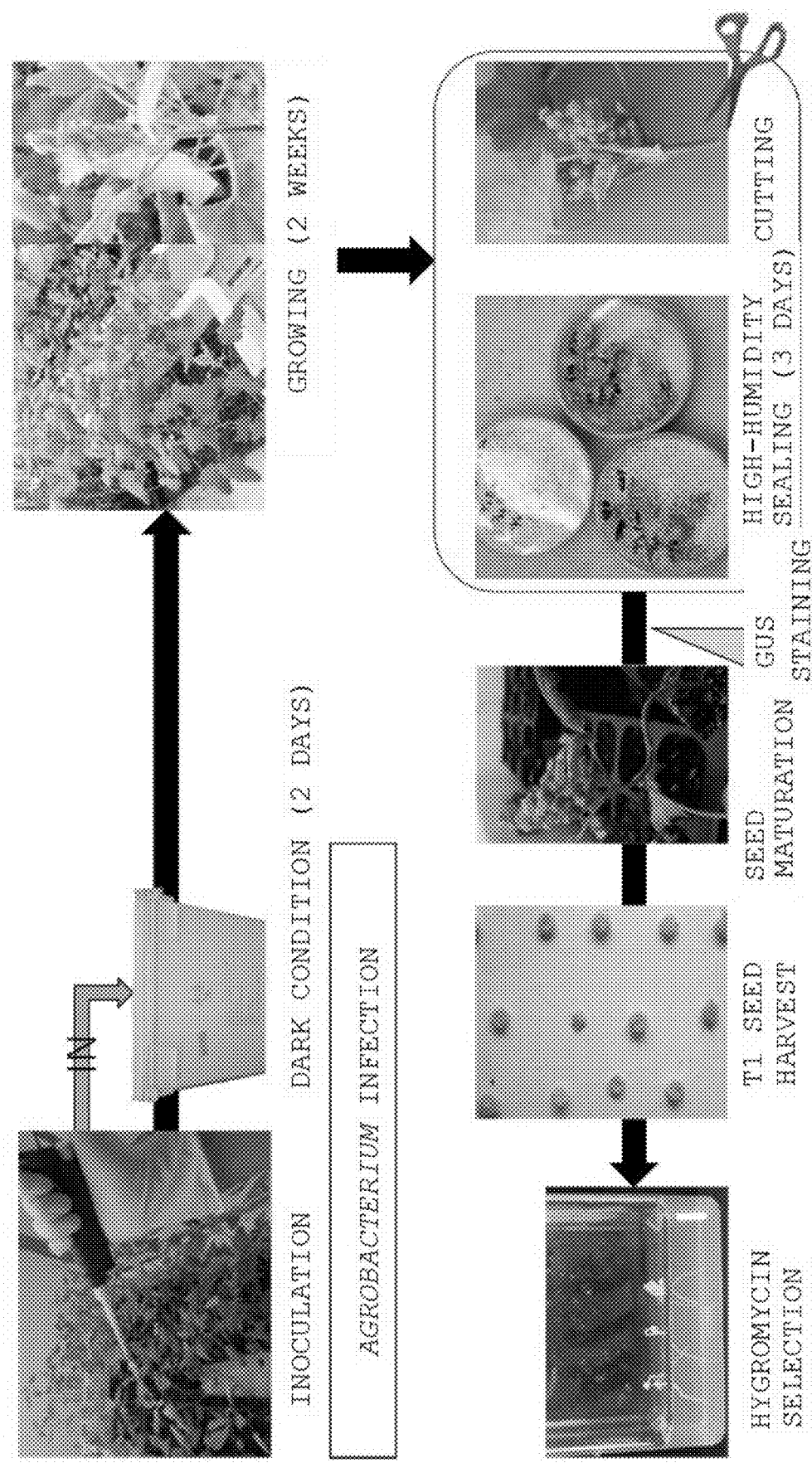
FIG. 11 shows the procedure of a "floral dip/cutting-sealing method," which is an improved version of a floral dip method. In a cutting-sealing treatment (−) group, GUS staining was performed at 2 weeks after infection treatment. In a cutting-sealing treatment (+) group, cutting-sealing treatment was performed at 2 weeks after infection treatment, and then GUS staining was performed.

This technique, which was obtained by adding high-humidity/dark-condition (sealing) treatment to the floral dip method was named "floral dip/cutting-sealing method" (FIG. 11).

TABLE 6

| Cutting-sealing treatment (−) | | | | | Number of days elapsed after seeding | Cutting-sealing treatment (+) | | | | |
|---|---|---|---|---|---|---|---|---|---|---|
| 55* | 50* | 45* | 40* | 30* | (days)* | 30* | 40* | 45* | 50* | 55* |
| 5 | 3 | 4 | 6 | 3 | Number of tested ears (ears)* | 3 | 6 | 8 | 3 | 7 |
| 0 | 0 | 0 | 0 | 0 | GUS-expressing ears (ears)* | 0 | 2 | 4 | 1 | 0 |

Comparison by GUS staining of *quinoa* with differences in terms of cutting-sealing treatment and growth stages at testing Example 2

[Transformation Experiment on Dedifferentiated Cells (Calluses)]

(Comparison of Transformed Callus Formation Abilities of Seven *Agrobacterium* Strains in Kd Variety)

Figure 12:
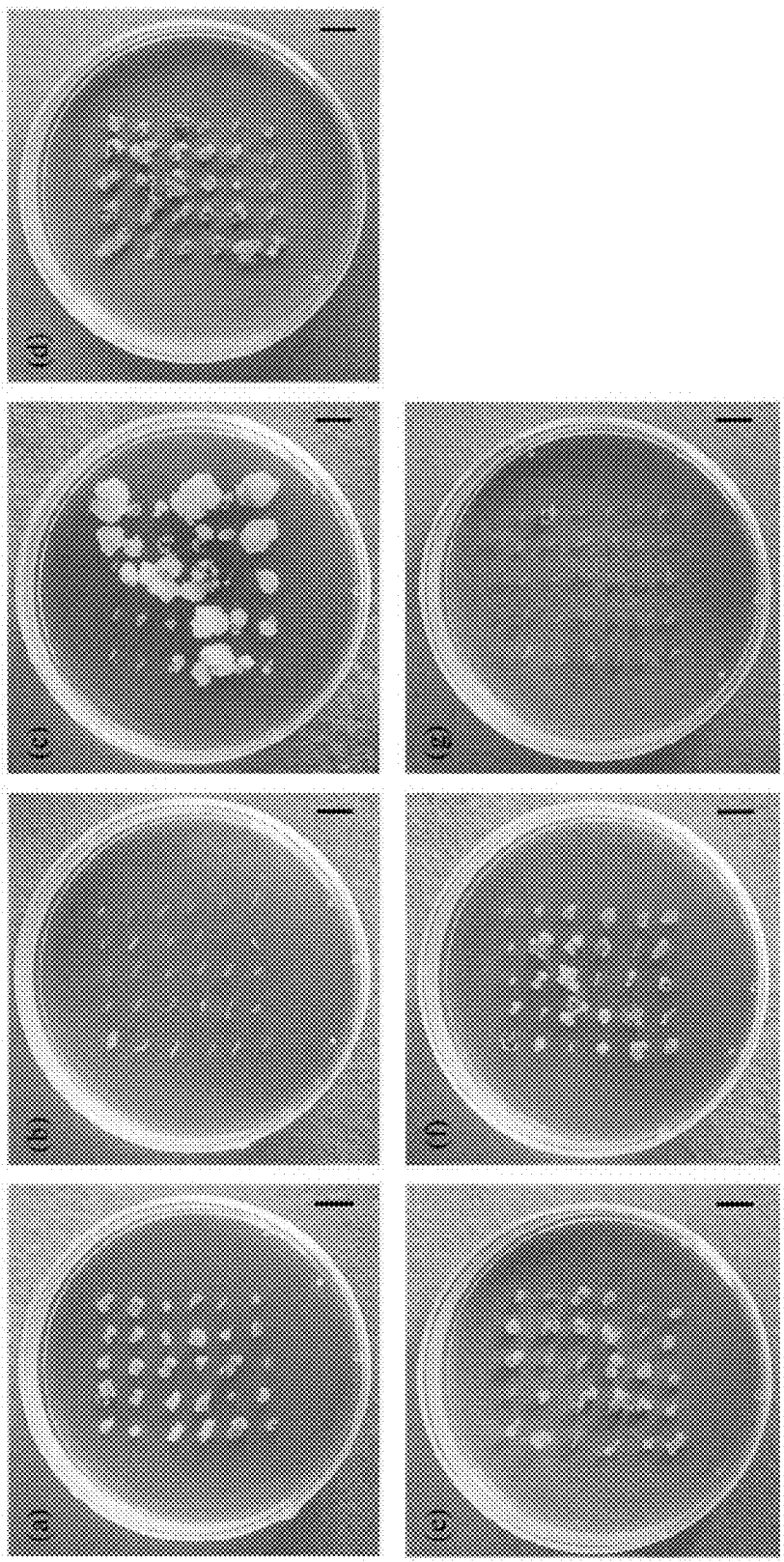
FIG. 12 show calluses induced from hypocotyl sections of the Kd variety infected with seven *Agrobacterium* strains. (a) Calluses infected with a GV3101 strain; (b) calluses infected with an ATCC15834 strain; (c) calluses infected with an MAFF301276 strain; (d) calluses infected with an MAFF212033 strain; (e) calluses infected with an MAFF311303 strain; (f) calluses infected with an MAFF211729 strain; and (g) calluses infected with an MAFF663001 strain.
Figure 13:
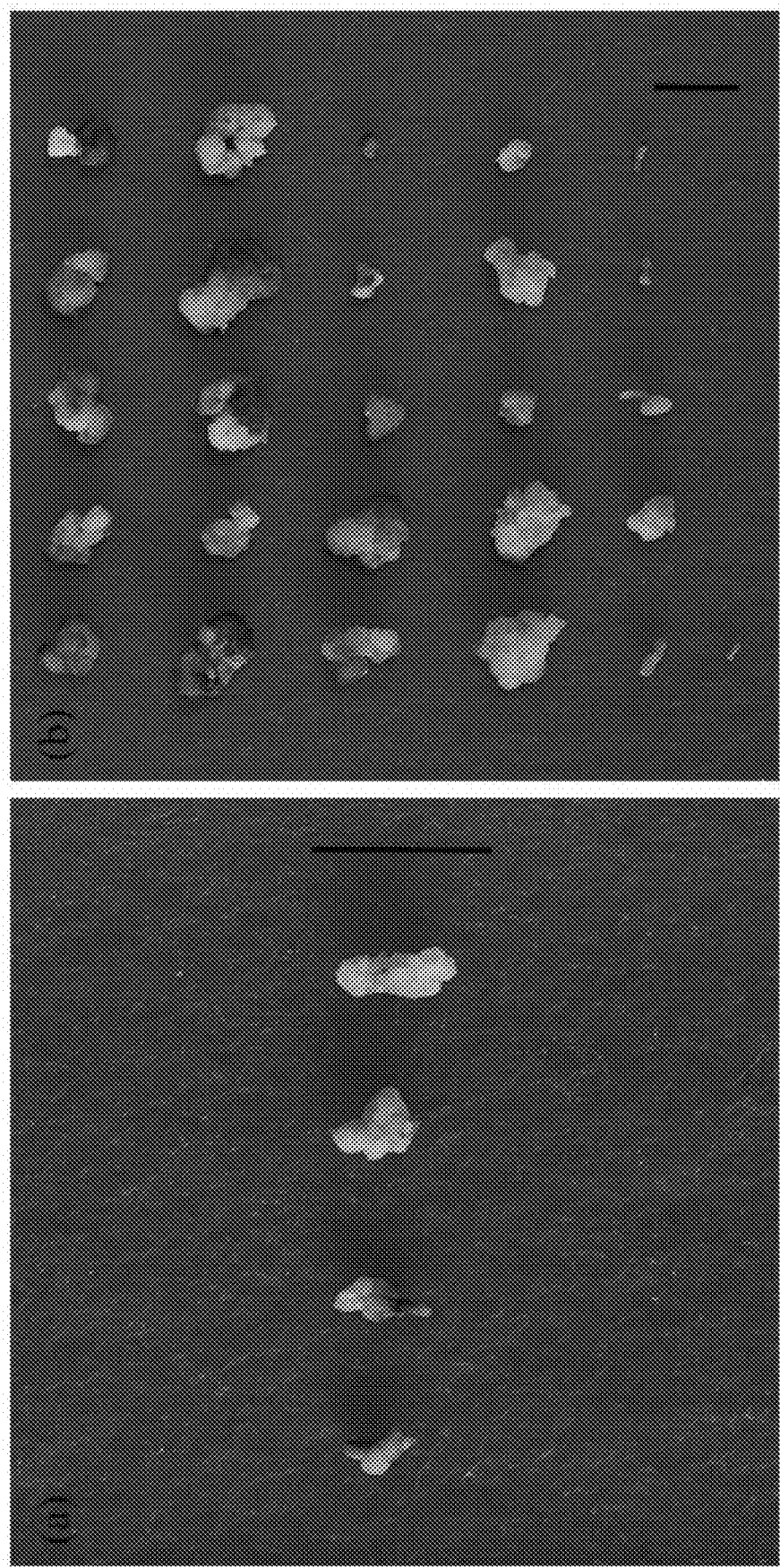
FIG. 13 show GUS expression in calluses induced from hypocotyl sections of the Kd variety infected with seven *Agrobacterium* strains. (a) Transformed calluses of the Kd variety infected with the GV3101 strain; and (b) transformed calluses of the Kd variety infected with the MAFF301276 strain. GUS staining was performed for calluses at 6 weeks after infection treatment. The scale bars each represent 1 cm.
Figure 14:
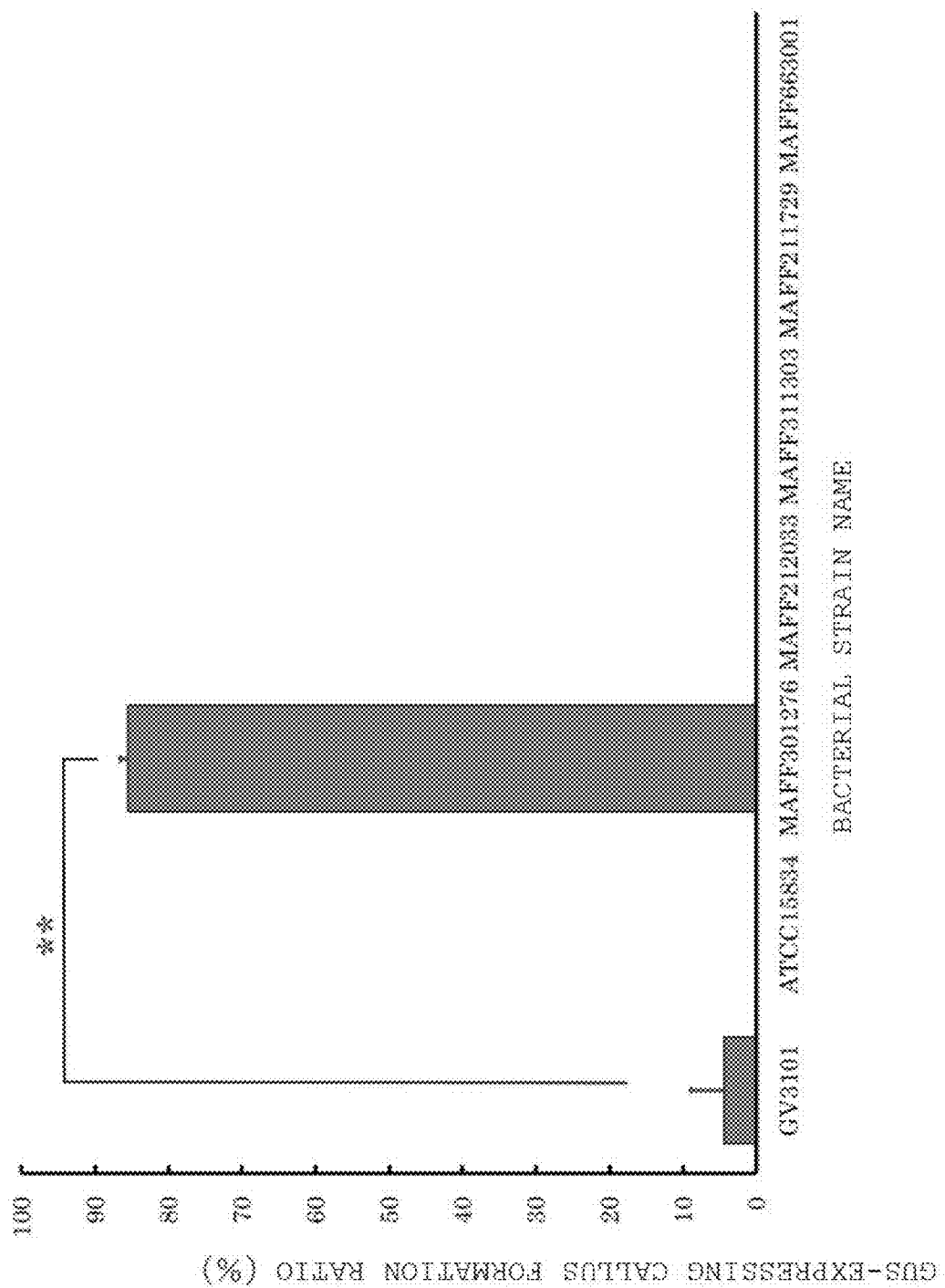
FIG. 14 shows transformed callus formation ratios of hypocotyl sections of the Kd variety infected with seven *Agrobacterium* strains. GUS staining was performed for calluses at 6 weeks after infection treatment. ** represents the presence of a statistically significant difference at 1% level (T-test). The graph shows the mean±standard deviation of three infection experiments in which hypocotyl sections (n=30) of *quinoa* were tested.

Induction of transformed calluses was attempted by infecting hypocotyl sections of the Kd variety with seven *Agrobacterium* strains having the binary vector pCAMBIA1301 (GV3101 strain, ATCC15834 strain, MAFF301276 strain, MAFF212033 strain, MAFF311303 strain, MAFF211729 strain, and MAFF663001 strain). As a result, GUS expression was found in calluses induced with the GV3101 strain and the MAFF301276 strain (FIG. 12 and FIG. 13). The transformation efficiencies of the GV3101 strain and the MAFF301276 strain were 4.4±7.7% and 85.6±1.9%, respectively (mean±standard deviation) (FIG. 14 and Table 7).

TABLE 7

| Bacterial strain name | Number of sections used in experiment | Number of GUS-expressing calluses formed | (%) |
|---|---|---|---|
| GV3101 | 30 | 1.3 ± 2.3 | (4.4 ± 7.7) |
| ATCC15834 | 30 | 0 | (0) |
| MAFF301276 | 30 | 25.7 ± 0.6 | (85.6 ± 1.9) |
| MAFF212033 | 30 | 0 | (0) |
| MAFF311303 | 30 | 0 | (0) |
| MAFF211729 | 30 | 0 | (0) |
| MAFF663001 | 30 | 0 | (0) |

Transformed callus formation ratios of the Kd variety infected with seven *Agrobacterium* strains. GUS staining was performed for calluses at 6 weeks after infection treatment. Values represent the mean±standard deviation of three infection experiments in which hypocotyl sections (n=30) of *quinoa* were tested.
(Comparison of Transformed Callus Formation Abilities in Six Varieties of *Quinoa* Subjected to Infection Experiment with GV3101 Strain and MAFF301276 Strain of *Agrobacterium*)

Figure 15:
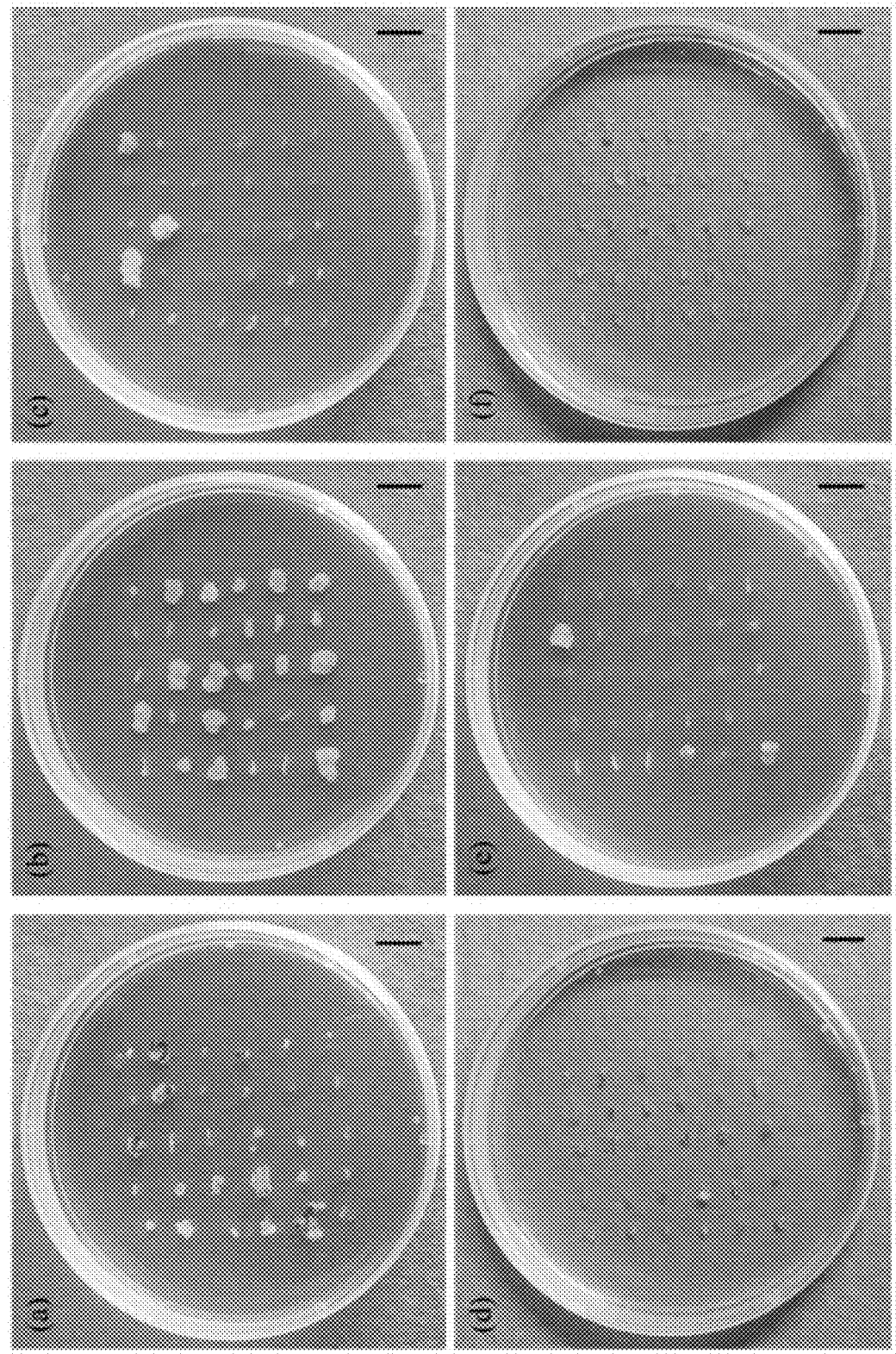
FIG. 15 show calluses induced from hypocotyl sections of *quinoa* infected with the *Agrobacterium* GV3101 strain. (a) Calluses of the Kd variety; (b) calluses of a 85 variety; (c) calluses of a 108 variety; (d) calluses (hypocotyl sections) of the mutant rebc; (e) calluses of the mutant ghy; and (f) calluses (hypocotyl sections) of the mutant ghy/rebc. FIG.

*Quinoa* forms bladder cells, which are involved in stress tolerance, on its shoot apex and leaf surfaces. In consideration of the influence of the bladder cells on the transformation of *quinoa*, the mutant (rebc) reduced in ability to form those tissues, and the mutant (ghy/rebc) reduced in both of betalain pigment synthesis ability and bladder cell formation ability were also investigated for their transformation efficiencies. When six varieties of *quinoa*, i.e., the Kd variety, the 85 variety, the 108 variety, the mutant ghy, the mutant rebc, and the mutant ghy/rebc were infected with the GV3101 strain, calluses were formed in five varieties other than the mutant ghy/rebc (FIG. 15). Of those, varieties recognized to exhibit GUS expression were the 85 variety, the mutant rebc, and the mutant ghy with GUS-expressing callus formation ratios of 21.1±6.9%, 6.7±3.3%, and 1.1±1.9% (mean±standard deviation), respectively (FIGS. 16, FIG. 17, and Table 8). Meanwhile, when the six varieties of *quinoa* were infected with the MAFF301276 strain, transformed calluses were formed in all the *quinoa* varieties, and GUS-expressing callus formation ratios were increased in all the varieties as compared to the infection experiment using the GV3101 strain (FIG. 18 to FIG. 20 and Table 9). The transformation efficiency was found to be 60% or more in each of the Kd variety, the 85 variety, and the mutant rebc, and was highest at 80.0±15.8% in the 85 variety (mean±standard deviation).

TABLE 8

| Bacterial strain name | Number of sections used in experiment | Number of GUS-expressing calluses formed | (%) |
|---|---|---|---|
| Kd | 30 | 0 | (0) |
| 85 | 30 | 6.3 ± 1.2 | (21.1 ± 4.0) |
| 108 (WT) | 30 | 0 | (0) |

TABLE 8-continued

| Bacterial strain name | Number of sections used in experiment | Number of GUS-expressing calluses formed | (%) |
|---|---|---|---|
| rebc1 | 30 | 2.0 ± 0.6 | (6.7 ± 1.9) |
| ghy | 30 | 0.3 ± 0.3 | (1.1 ± 1.1) |
| ghy/rebc1 | 30 | 0 | (0) |

Transformed callus formation ratios of the six varieties of *quinoa* infected with the *Agrobacterium* strain GV3101. GUS staining was performed for calluses at 6 weeks after infection treatment. Values represent the mean±standard deviation of three infection experiments in which hypocotyl sections (n=30) of *quinoa* were tested.

TABLE 9

| Bacterial strain name | Number of sections used in experiment | Number of GUS-expressing calluses formed | (%) |
|---|---|---|---|
| Kd | 30 | 21.0 ± 3.6 | (70.0 ± 12.0) |
| 85 | 30 | 24.0 ± 3.0 | (80.0 ± 10.0) |
| 108 (WT) | 30 | 10.7 ± 5.7 | (35.6 ± 19.0) |
| rebc1 | 30 | 18.7 ± 9.2 | (62.2 ± 30.8) |
| ghy | 30 | 6.7 ± 4.0 | (22.2 ± 13.5) |
| ghy/rebc1 | 30 | 7.0 ± 3.0 | (23.3 ± 10.0) |

Transformed callus formation ratios of the six varieties of *quinoa* infected with the *Agrobacterium* MAFF301276. GUS staining was performed for calluses at 6 weeks after infection treatment. Values represent the mean±standard deviation of three infection experiments in which hypocotyl sections (n=30) of *quinoa* were tested.
(Analyses of T-DNA Insertion Site in *Quinoa* Seedling Gall Tissue Using Next-Generation Sequencer and PCR)

In order to determine the site of gene introduction into the *quinoa* genome by the MAFF301276 strain, the genomic DNA of the MAFF301276 strain and the genomic DNA of the gall induced by the MAFF301276 strain (FIG. 21) were subjected to analysis using a next-generation sequencer MinION, which was outsourced to the Laboratory of Plant Gene Technology of Ishikawa Prefectural University. The results of the analysis of the genomic DNA extracted from the gall revealed that there was one read in which the binary vector pCAMBIA1301 and the *quinoa* genome were fused among 3,000,000 reads (about 8 Gbp) (FIG. 22). Analysis of the genome insertion region with Blastx revealed the presence of a hygromycin gene derived from the binary vector pCAMBIA1301, and two auxin synthesis genes (iaaH and iaaM) and a cytokinin synthase gene (ipt) derived from the MAFF301276 strain pTi plasmid, and two kinds of T-DNAs were inserted into the genome in a state of being fused to each other. In addition, the results of similar analysis for the genomic DNA of *quinoa* gall infected with the MAFF301276 strain having the binary vector pCAMBIA-CqCYP76AD1-1 revealed that two kinds of T-DNAs were inserted into the *quinoa* genome in a state of being fused to each other as with the binary vector pCAMBIA1301. Five kinds of primers were designed for a site in which the T-DNA of the MAFF301276 strain and the *quinoa* genome were adjacent to each other, and PCR analysis was performed with six pairs (FIG. 7 and Table 5), and as a result, gene amplification was found for primer sets 1, 2, 4, and 5 representing a connecting portion between the bacterium and the *quinoa* genome. The results of the analyses using the PCR and the next-generation sequencer revealed that the MAFF301276 strain was capable of introducing a gene into the *quinoa* genome.

Example 3

[Production of Transformed *Quinoa* by Floral Dip/Cutting-Sealing Method]
(Comparison of GUS Gene Introduction Abilities of Seven *Agrobacterium* Strains for Four Varieties of *Quinoa* in Floral Dip/Cutting-Sealing Method)

Evaluation was performed for *quinoa* varieties and *Agrobacterium* strains suited for the floral dip/cutting-sealing method capable of gene introduction into female organs. Four varieties of *quinoa* (Kd, ghy, rebc, and ghy/rebc) at from 50 days to 60 days after seeding, and seven *Agrobacterium* strains having introduced therein the binary vector pCAMBIA1301 (GV3101, ATCC15834, MAFF301276, MAFF212033, MAFF311303, MAFF211729, and MAFF663001) were subjected to the floral dip/cutting-sealing method in various combinations, and gene introduction was evaluated by GUS staining (Table 10). As a result, individuals using the MAFF212033 strain, the MAFF311303 strain, and the MAFF211729 strain were found to exhibit GUS expression in their female organs, and particularly in the case of using the MAFF311303 strain, GUS expression was found at high ratios (FIG. 23b, FIG. 24, and FIG. 25). Such GUS expression also occurred in calyx and anther tissues, and hence was conceived to be non-female organ-specific GUS expression. Previous experiments had required cutting-sealing treatment in gene introduction into *quinoa* by the floral dip method. However, in the infection experiments using the MAFF15834 strain, the MAFF301276 strain, the MAFF311303 strain, and the MAFF663001 strain, GUS expression in ears was found in the case of cutting-sealing treatment (−), and the MAFF301276 strain, which had the highest transformed callus formation ability (FIG. 14 and Table 8), was found to achieve GUS expression in ears of all the *quinoa* varieties tested (FIG. 26). In addition, the two *quinoa* mutant varieties in which bladder formation was suppressed tended to have high ratios of GUS-expressing individuals. However, GUS expression in female organs was not found under those cutting-sealing treatment (−) conditions (FIG. 23a).

LRB3W1 and a cell wall-degrading enzyme-producing *Serratia marcescens* strain B2 increased an inhibitory effect on the growth of a filamentous fungus (Someya N, Tsuchiya K, Yoshida T, T. Noguchi M, Akuthu K, and Sawada H (2007) Biocontrol Science. 12 (1): 1-6; Shigenobu Yoshida (2009) Interactions among Different Microbial Species and Their Possible Roles on Biological Control. Plant Protection 63 (10): 619-623). When such interaction is present between *Agrobacterium* strains, gene introduction efficiency into female organs can be expected to be improved by co-inoculation of two *Agrobacterium* strains. In view of this, inoculation experiments were performed on the Kd variety and the mutant ghy at from 50 days to 60 days after seeding using 21 combinations in which bacterial suspensions of two bacterial strains out of the seven *Agrobacterium* strains used in Example 3 were mixed at 1:1 (Table 10). The results were as follows: combinations recognized to show staining in female organs were the following five test groups in the Kd variety: GV3301 strain×ATCC15834 strain, GV3301 strain×MAFF211729 strain, GV3301 strain×MAFF663001 strain, MAFF212033 strain×MAFF311303 strain, and MAFF311303 strain×MAFF211729 strain (Table 11), and were the following four test groups in the mutant ghy: GV3301 strain×MAFF311303 strain, MAFF301276 strain× MAFF311303 strain, MAFF311303 strain×MAFF211729 strain, and MAFF211729 strain×MAFF663001 strain (Table 12). Such GUS staining in female organs also occurred in calyx and anther tissues as in the results of Example 3, and hence the expression was conceived to be non-female organ-specific. Meanwhile, combinations recognized to show GUS expression in ears in the case of cutting-sealing treatment (−) were the following five test groups in the Kd variety: GV3301 strain×MAFF301276 strain, GV3301 strain× MAFF663001 strain, ATCC15834 strain×MAFF211729 strain, MAFF301276 strain×MAFF211729 strain, and MAFF301276 strain×MAFF663001 strain (Table 11), and were the following seven test groups in the mutant ghy:

TABLE 10

| Bacterial strain name | GV3101 | ATCC15834 | MAFF301276 | MAFF212033 | MAFF311303 | MAFF211729 | MAFF663001 |
|---|---|---|---|---|---|---|---|
| GV3101 | GV3101* | GV3101* ATCC15834 | GV3101* MAFF301276* | GV3101* MAFF212033* | GV3101* MAFF311303* | GV3101* MAFF211729* | GV3101* MAFF663001* |
| ATCC15834 | | ATCC15834 | ATCC15834 MAFF301276* | ATCC15834 MAFF212033* | ATCC15834 MAFF311303* | ATCC15834 MAFF211729* | ATCC15834 MAFF663001* |
| MAFF301276 | | | MAFF301276* | MAFF301276* MAFF212033* | MAFF301276* MAFF311303* | MAFF301276* MAFF211729* | MAFF301276* MAFF663001* |
| MAFF212033 | | | | MAFF212033* | MAFF212033* MAFF311303* | MAFF212033* MAFF211729* | MAFF212033* MAFF663001* |
| MAFF311303 | | | | | MAFF311303* | MAFF311303* MAFF211729* | MAFF311303* MAFF663001* |
| MAFF211729 | | | | | | MAFF211729* | MAFF211729* MAFF663001* |
| MAFF663001 | | | | | | | MAFF663001* |

List of infection solutions used in floral dip/cutting-sealing experiments. The boxes with an "*" show bacterial strains used in Example 3, and other boxes show combinations of bacterial strains in a co-inoculation experiment.

(Influence of Co-inoculation of two *Agrobacterium* Strains on Transformation Efficiency in Floral Dip/Cutting-Sealing Method)

There is a report that co-inoculation of an antifungal substance-producing *Pseudomonas fluorescens* strain GV3301 strain×MAFF301276 strain, ATCC15834 strain× MAFF301276 strain, ATCC15834 strain×MAFF211729 strain, MAFF301276 strain×MAFF212033 strain, MAFF301276 strain×MAFF311303 strain, MAFF301276 strain×MAFF211729 strain, and MAFF301276 strain× MAFF663001 strain (Table 12). Also in the co-inoculation experiment with two bacterial strains, GUS expression in female organs was not found under the cutting-sealing treatment (−) condition.

TABLE 11

| Combination of bacteria | | Cutting-sealing treatment* | Number of individuals | Ratio of individuals expressing GUS in ears (%) | Ratio of individuals expressing GUS in female organs (%) |
|---|---|---|---|---|---|
| GV3101 | | − | 10 | 0.0 | 0.0 |
| ATCC15834 | | − | 10 | 0.0 | 0.0 |
| MAFF301276* | | − | 10 | 50.0 | 0.0 |
| MAFF212033 | | − | 10 | 0.0 | 0.0 |
| MAFF311303 | | − | 10 | 10.0 | 0.0 |
| MAFF211729 | | − | 10 | 0.0 | 0.0 |
| MAFF663001 | | − | 10 | 0.0 | 0.0 |
| GV3101 | × ATCC15834 | − | 10 | 0.0 | 0.0 |
| GV3101* | × MAFF301276 | − | 10 | 50.0 | 0.0 |
| GV3101 | × MAFF212033 | − | 10 | 0.0 | 0.0 |
| GV3101 | × MAFF311303 | − | 10 | 0.0 | 0.0 |
| GV3101 | × MAFF211729 | − | 10 | 0.0 | 0.0 |
| GV3101 | × MAFF663001 | − | 10 | 10.0 | 0.0 |
| ATCC15834 | × MAFF301276 | − | 10 | 0.0 | 0.0 |
| ATCC15834 | × MAFF212033 | − | 10 | 0.0 | 0.0 |
| ATCC15834 | × MAFF311303 | − | 10 | 0.0 | 0.0 |
| ATCC15834 | × MAFF211729 | − | 10 | 10.0 | 0.0 |
| ATCC15834 | × MAFF663001 | − | 10 | 0.0 | 0.0 |
| MAFF301276 | × MAFF212033 | − | 10 | 0.0 | 0.0 |
| MAFF301276 | × MAFF311303 | − | 11 | 0.0 | 0.0 |
| MAFF301276* | × MAFF211729 | − | 11 | 18.2 | 0.0 |
| MAFF301276* | × MAFF663001 | − | 20 | 50.0 | 0.0 |
| MAFF212033 | × MAFF311303 | − | 10 | 0.0 | 0.0 |
| MAFF212033 | × MAFF211729 | − | 10 | 0.0 | 0.0 |
| MAFF212033 | × MAFF663001 | − | 10 | 0.0 | 0.0 |
| MAFF311303 | × MAFF211729 | − | 17 | 0.0 | 0.0 |
| MAFF311303 | × MAFF663001 | − | 10 | 0.0 | 0.0 |
| MAFF211729 | × MAFF663001 | − | 10 | 0.0 | 0.0 |
| GV3101 | | + | 10 | 30.0 | 0.0 |
| ATCC15834 | | + | 10 | 30.0 | 0.0 |
| MAFF301276* | | + | 10 | 60.0 | 0.0 |
| MAFF212033 | | + | 10 | 30.0 | 0.0 |
| MAFF311303 | | + | 10 | 80.0 | 50.0 |
| MAFF211729 | | + | 10 | 20.0 | 0.0 |
| MAFF663001 | | + | 10 | 40.0 | 0.0 |
| GV3101 | × ATCC15834 | + | 10 | 70.0 | 10.0 |
| GV3101* | × MAFF301276 | + | 10 | 50.0 | 0.0 |
| GV3101 | × MAFF212033 | + | 10 | 0.0 | 0.0 |
| GV3101 | × MAFF311303 | + | 10 | 0.0 | 0.0 |
| GV3101 | × MAFF211729 | + | 10 | 70.0 | 10.0 |
| GV3101 | × MAFF663001 | + | 10 | 100.0 | 30.0 |
| ATCC15834* | × MAFF301276 | + | 10 | 70.0 | 0.0 |
| ATCC15834 | × MAFF212033 | + | 10 | 20.0 | 0.0 |
| ATCC15834 | × MAFF311303 | + | 10 | 30.0 | 0.0 |
| ATCC15834 | × MAFF211729 | + | 10 | 20.0 | 0.0 |
| ATCC15834 | × MAFF663001 | + | 10 | 10.0 | 0.0 |
| MAFF301276* | × MAFF212033 | + | 10 | 30.0 | 0.0 |
| MAFF301276* | × MAFF311303 | + | 10 | 70.0 | 0.0 |
| MAFF301276* | × MAFF211729 | + | 10 | 20.0 | 0.0 |
| MAFF301276* | × MAFF663001 | + | 20 | 65.0 | 0.0 |
| MAFF212033 | × MAFF311303 | + | 10 | 10.0 | 10.0 |
| MAFF212033 | × MAFF211729 | + | 10 | 30.0 | 0.0 |
| MAFF212033 | × MAFF663001 | + | 10 | 0.0 | 0.0 |
| MAFF311303 | × MAFF211729 | + | 20 | 30.0 | 5.0 |
| MAFF311303 | × MAFF663001 | + | 10 | 20.0 | 0.0 |
| MAFF211729 | × MAFF663001 | + | 10 | 0.0 | 0.0 |

Results of co-inoculation experiment with two bacterial strains on Kd variety by floral dip/cutting-sealing method.
In *cutting-sealing treatment, "−" represents the absence of cutting-sealing treatment, and cutting-sealing treatment "+" represents the presence of cutting-sealing treatment.
Boxed rows show groups found to show GUS staining in female organs.
The measurement method is described in "Measurement of Ratio of GUS-expressing Individuals" (FIG. 1).

Results of co-inoculation experiment with two bacterial strains on Kd variety by floral dip/cutting-sealing method. In *cutting-sealing treatment, "−" represents the absence of cutting-sealing treatment, and cutting-sealing treatment "+" represents the presence of cutting-sealing treatment. Boxed rows show groups found to show GUS staining in female organs. The measurement method is described in "Measurement of Ratio of GUS-expressing Individuals" (FIG. 1).

TABLE 12

| Combination of bacteria | | Cutting-sealing treatment* | Number of individuals | Ratio of individuals expressing GUS in ears (%) | Ratio of individuals expressing GUS in female organs (%) |
|---|---|---|---|---|---|
| GV3101 | | − | 10 | 0.0 | 0.0 |
| ATCC15834 | | − | 10 | 0.0 | 0.0 |
| MAFF301276* | | − | 8 | 25.0 | 0.0 |
| MAFF212033 | | − | 7 | 0.0 | 0.0 |
| MAFF311303 | | − | 10 | 0.0 | 0.0 |
| MAFF211729 | | − | 10 | 0.0 | 0.0 |
| MAFF663001 | | − | 10 | 10.0 | 0.0 |
| GV3101 | × ATCC15834 | − | 10 | 0.0 | 0.0 |
| GV3101* | × MAFF301276 | − | 10 | 90.0 | 0.0 |
| GV3101 | × MAFF212033 | − | 9 | 0.0 | 0.0 |
| GV3101 | × MAFF311303 | − | 8 | 0.0 | 0.0 |
| GV3101 | × MAFF211729 | − | 8 | 0.0 | 0.0 |
| GV3101 | × MAFF663001 | − | 10 | 0.0 | 0.0 |
| ATCC15834* | × MAFF301276 | − | 10 | 80.0 | 0.0 |
| ATCC15834 | × MAFF212033 | − | 10 | 0.0 | 0.0 |
| ATCC15834 | × MAFF311303 | − | 10 | 0.0 | 0.0 |
| ATCC15834 | × MAFF211729 | − | 10 | 20.0 | 0.0 |
| ATCC15834 | × MAFF663001 | − | 10 | 0.0 | 0.0 |
| MAFF301276* | × MAFF212033 | − | 10 | 90.0 | 0.0 |
| MAFF301276* | × MAFF311303 | − | 10 | 50.0 | 0.0 |
| MAFF301276* | × MAFF211729 | − | 8 | 75.0 | 0.0 |
| MAFF301276* | × MAFF663001 | − | 10 | 70.0 | 0.0 |
| MAFF212033 | × MAFF311303 | − | 8 | 0.0 | 0.0 |
| MAFF212033 | × MAFF211729 | − | 20 | 0.0 | 0.0 |
| MAFF212033 | × MAFF663001 | − | 10 | 0.0 | 0.0 |
| MAFF311303 | × MAFF211729 | − | 10 | 0.0 | 0.0 |
| MAFF311303 | × MAFF663001 | − | 10 | 0.0 | 0.0 |
| MAFF211729 | × MAFF663001 | − | 10 | 0.0 | 0.0 |
| GV3101 | | + | 10 | 0.0 | 0.0 |
| ATCC15834 | | + | 10 | 0.0 | 0.0 |
| MAFF301276* | | + | 10 | 60.0 | 0.0 |
| MAFF212033 | | + | 10 | 30.0 | 0.0 |
| MAFF311303 | | + | 10 | 20.0 | 0.0 |
| MAFF211729 | | + | 10 | 60.0 | 10.0 |
| MAFF663001 | | + | 10 | 20.0 | 0.0 |
| GV3101 | × ATCC15834 | + | 10 | 10.0 | 0.0 |
| GV3101* | × MAFF301276 | + | 10 | 90.0 | 0.0 |
| GV3101 | × MAFF212033 | + | 10 | 40.0 | 0.0 |
| GV3101 | × MAFF311303 | + | 8 | 87.5 | 12.5 |
| GV3101 | × MAFF211729 | + | 10 | 50.0 | 0.0 |
| GV3101 | × MAFF663001 | + | 10 | 0.0 | 0.0 |
| ATCC15834* | × MAFF301276 | + | 10 | 90.0 | 0.0 |
| ATCC15834 | × MAFF212033 | + | 10 | 20.0 | 0.0 |
| ATCC15834 | × MAFF311303 | + | 10 | 0.0 | 0.0 |
| ATCC15834 | × MAFF211729 | + | 10 | 0.0 | 0.0 |
| ATCC15834 | × MAFF663001 | + | 10 | 0.0 | 0.0 |
| MAFF301276* | × MAFF212033 | + | 10 | 70.0 | 0.0 |
| MAFF301276* | × MAFF311303 | + | 10 | 80.0 | 10.0 |
| MAFF301276* | × MAFF211729 | + | 10 | 70.0 | 0.0 |
| MAFF301276* | × MAFF663001 | + | 10 | 80.0 | 0.0 |
| MAFF212033 | × MAFF311303 | + | 10 | 50.0 | 0.0 |
| MAFF212033 | × MAFF211729 | + | 20 | 10.0 | 0.0 |
| MAFF212033 | × MAFF663001 | + | 10 | 10.0 | 0.0 |
| MAFF311303 | × MAFF211729 | + | 10 | 20.0 | 20.0 |
| MAFF311303 | × MAFF663001 | + | 10 | 10.0 | 0.0 |
| MAFF211729 | × MAFF663001 | + | 10 | 50.0 | 10.0 |

Results of co-inoculation experiment with two bacterial strains on mutant ghy by floral dip/cutting-sealing method.
In *cutting-sealing treatment, "−" represents the absence of cutting-sealing treatment, and cutting-sealing treatment "+" represents the presence of cutting-sealing treatment.
Boxed rows show groups found to show GUS staining in female organs.
The measurement method is described in "Measurement of Ratio of GUS-expressing Individuals" (FIG. 1).

Results of co-inoculation experiment with two bacterial strains on mutant ghy by floral dip/cutting-sealing method. In *cutting-sealing treatment, "−" represents the absence of cutting-sealing treatment, and cutting-sealing treatment "+" represents the presence of cutting-sealing treatment. Boxed rows show groups found to show GUS staining in female organs. The measurement method is described in "Measurement of Ratio of GUS-expressing Individuals" (FIG. 1).

Example 4

[Production of Transformed *Quinoa* by Floral Dip/Non-Cutting-Sealing Method Using Improved Bacterium (MAFF311303pTiMAFF301276ΔT-DNA)]
(Introduction of gusA Gene into Four Varieties of *Quinoa* by Floral Dip/Non-Cutting-Sealing Method Using Improved Bacterium (MAFF311303pTiMAFF301276ΔT-DNA))

The MAFF311303 strain was found to cause GUS expression in female organs at high ratios through the floral dip/cutting-sealing method (FIG. 23*b*). However, the MAFF311303 strain is nonpathogenic, and hence, presumably, does not carry vir genes and has a low gene introduction ability. Meanwhile, the MAFF301276 strain introduced T-DNA into *quinoa* calluses and *quinoa* ears with high efficiency (FIG. 14, Table 8, and FIG. 26). However, the MAFF301276 strain was not found to achieve gene introduction into female organs (FIG. 23). Further, even in the case of performing co-inoculation of the MAFF301276 strain and the MAFF311303 strain, when the cutting-sealing treatment was not performed, GUS expression in female organs was not found (Table 11 and Table 12). In view of this, MAFF311303pTiMAFF301276ΔT-DNA bringing together the characteristics of the MAFF301276 strain and the MAFF311303 strain was produced. The binary vector pCAMBIA1301 was introduced into this bacterial strain, and then four varieties of *quinoa* (Kd, ghy, rebc, and ghy/rebc) were inoculated therewith by the conventional floral dip method (without cutting-sealing treatment). As a result, female organ-specific GUS expression was recognized in the mutant ghy and the mutant ghy/rebc (FIG. 27 to FIG. 29).

(Influence of Abscisic Acid on Transformation Efficiency in Floral Dip/Non-Cutting-Sealing Method Using Improved Bacterium (MAFF311303pTiMAFF301276ΔT-DNA))

Abscisic acid (ABA) has an antagonistic relationship with salicylic acid (SA), which is involved in the induction of systemic acquired resistance (SAR) of plants (Durner J, Shah J, and Klessig D F (1997) Trends in Plant Science. 2 (7): 266-274: Yasuda M, Ishikawa A, Jikumaru Y, Seki M, Umezawa T, Asami T, Maruyama-Nakashita A, Kudo T, Shinozaki K, Yoshida S, and Nakashita H (2008) Plant Cell 20 (6): 1678-1692.). Accordingly, the addition of ABA was suspected to suppress SAR to increase transformation efficiency in a floral dip experiment on *quinoa*. 500 mM ABA was added to a bacterial suspension of MAFF311303pTiMAFF301276ΔT-DNA harboring the binary vector pCAMBIA1301, and four varieties of *quinoa* (Kd, ghy, rebc, and ghy/rebc) were inoculated therewith by the conventional floral dip method (without cutting-sealing treatment). As a result, the mutant ghy/rebc was recognized to exhibit female organ-specific GUS expression in 60% of its individuals, which was 6 times as high as that in the case of adding no ABA (FIG. 30 and FIG. 31).

Example 5

(Evaluation of Redifferentiation Conditions in Mutant ghy)

A medium was produced by partially modifying spinach redifferentiation medium composition reported in the literature (Jinhua Bao (2009) Establishment of Transformation System for Spinach based on *Agrobacterium* Method and Introduction of Useful Gene, Chiba University Graduate School doctoral dissertation), and was used in the experiment (Table 2). Non-transformed calluses induced from seedling sections of the Kd variety were cultured under preset conditions shown in Table 13. A "+" group for the redifferentiation inducing light condition was cultured in an incubator at 20° C. under 8-h light/16-h dark conditions, and a "−" group was placed in a steel can in an incubator under the same conditions, and was cultured under a light-shielding condition. In groups with GA concentrations of 1 and 2, non-transformed calluses were plated on redifferentiation media supplemented with gibberellin at 1 mg/L and 2 mg/L, respectively.

Transformed calluses were successfully formed in the mutant ghy variety incapable of synthesizing betalain pigments. In view of this, an attempt was made to induce redifferentiation from calluses of the mutant ghy. 2,4-Dichlorophenoxyacetic acid (2,4-D) serving as a plant hormone having an auxin-like action, and benzyladenine and kinetin each serving as a plant hormone having a cytokinin-like action were combined at various concentrations, and redifferentiation was attempted. Calluses plated in media containing the cytokinin-like plant hormones turned green, and calluses plated in benzyladenine-containing media turned darker green. In addition, when the concentrations of both of 2,4-D and the cytokinin-like plant hormone (benzyladenine or kinetin) were increased, hard and rounded calluses were obtained. Further, adventitious roots were redifferentiated in a medium containing only 0.01 mg/L or 0.1 mg/L 2,4-D, 0 mg/L to 0.1 mg/L 2,4-D and kinetin, or only 1 mg/L or 2 mg/L benzyladenine. In particular, calluses plated in a medium containing 1 mg/L kinetin and 0.01 mg/L 2,4-D, or only 1 mg/L kinetin showed remarkable elongation of adventitious roots. However, redifferentiation of any other organ was not found.

TABLE 13

| Group | Light condition | Bacterial infection (bialaphos resistance gene) | Bialaphos |
| --- | --- | --- | --- |
| (1) | + | + | + |
| (2) | − | + | + |
| (3) | + | − | + |
| (4) | − | − | + |
| (5) | + | + | − |
| (6) | − | + | − |
| (7) | + | − | − |
| (8) | − | − | − |

Preset callus inducing conditions. Light condition "+": at 20° C. under 8-h light/16-h dark conditions, light condition "−": shielded from light in a steel can in an incubator at 20° C. under 8-h light/16-h dark conditions. Bacterial infection treatment "+": infection treatment (see "Transformed Callus Experiment") was performed, bacterial infection treatment "−": infection treatment was not performed. Bialaphos "+": a callus induction medium supplemented with 5 mg/L bialaphos was used, bialaphos "−": a callus induction medium supplemented with no bialaphos was used.

Example 6

[Transformation of rebc Mutant *Quinoa* with wild-type REBC Gene by Floral Dip/Cutting-Sealing Method]

As a plant body to be used in transformation, there was used rebc mutant *quinoa* having a trait of having a markedly reduced number of bladder cells (individual recognized to have a c.1139G>A (p.Trp380*) mutation in the REBC gene (gene encoding Acc.No. XP_021715187) involved in bladder formation regulation) produced by the inventors of the present invention through 0.2% ethyl methanesulfonate (EMS) treatment of *quinoa* seeds.

Individuals about 2 months (flowering stage) after sowing of seeds of the M3 generation of the rebc mutant *quinoa* were transformed by the floral dip/cutting-sealing method of the present invention using the improved bacterium (MAFF311303pTiMAFF301276ΔT-DNA) having introduced therein the binary vector pCAMBIA1301 having inserted therein the wild-type REBC gene (SEQ ID NO: 14) connected to a REBC promoter (SEQ ID NO: 13) (FIG. 34).

As a result of the transformation, transformants in which bladders were restored were obtained (FIG. 35).

The obtained transformants were subjected to sequencing of the REBC gene, and it was recognized that the base sequence of the REBC gene was of the mutant type (FIG. 36, SEQ ID NO: 15).

This suggested that the restoration of the bladders through the transformation was highly likely due to the introduced gene.

In view of the foregoing, for the transformed plants in which bladders were restored, the genome of the transformants was sequenced utilizing a next-generation sequencer.

As a result, it was able to be recognized that the REBC gene had been introduced into the genome of the transformed plants (FIG. 37). At the same time, the introduction site was also identified (Chr16, 75355785 bp).

It was recognized from the above-mentioned results that the transformation using the floral dip/cutting-sealing method of the present invention enabled the expression of the bladders of a plant body (restoration of its bladder expression function), and the plant body was a transformant (rebc mutation-complemented individual).

The obtained transformants were pollinated (crossbred) with each other, and then seeds (transformed progeny) harvested from the resultant transformant were sown and grown.

As a result, the phenotypes of the progeny were separated into a wild-type having bladders (with the introduced gene) and a rebc mutant type (without the introduced gene) (FIG. 38).

It was recognized from the result that the transformation using the floral dip/cutting-sealing method of the present invention allowed the gene introduced through the transformation (e.g., bladder expression function gene) to be inherited by the progeny.

[General Remark]

In Examples of the present invention, at first, an attempt to produce a transformed plant through tissue culture was made using the Kd variety of *quinoa* and the *Agrobacterium* (*Rhizobium radiobacter*) strain GV3101, but failed in construction of a redifferentiation system and gene introduction.

No redifferentiation system for *quinoa* had been established, and hence a transformation experiment was performed by the floral dip method. However, when the floral dip method widely used in *Arabidopsis* (Clough S J and Bent A F (1998) The Plant Journal 16 (6): 735-743) was performed, GUS expression in ears was not found (FIG. 8). In view of this, ears infected with the GV3101 strain were subjected to cutting/high-humidity sealing treatment. As a result, GUS expression was recognized in ears of *quinoa* (FIG. 9). This result revealed that the cutting-sealing treatment enabled gene introduction into *quinoa*. Further, GUS expression in female organs was recognized (FIG. 10). There is a report that, in the floral dip method for *Arabidopsis*, the *Agrobacterium* targets a female reproductive organ (Desfeux C, Clough S J, and Bent A F (2000) Plant Physiology 123 (3): 895-904). Accordingly, transformed seeds are also obtained in *quinoa* through application of the floral dip/cutting-sealing method (FIG. 11).

Koga et al. have revealed that the cutting of the leaf sheath of a rice plant (*Oryza sativa* L.) reduces its resistance, whole plant specific resistance (WPSR), to infection with a rice blast pathogen *Magnaporthe grisea* (Koga H, Dohi H, Nakayachi O, and Mori M (2004) Physiological and Molecular Plant Pathology 64 (2): 67-72). This phenomenon involves abscisic acid (ABA) synthesized in the plant body through cutting treatment (Koga H, Dohia K, and Mori M (2004) Physiological and Molecular Plant Pathology 65 (1): 3-9), and ABA acts antagonistically to salicylic acid, which induces the systemic acquired resistance (SAR) of the plant (Yasuda M, Ishikawa A, Jikumaru Y, Seki M, Umezawa T, Asami T, Maruyama-Nakashita A, Kudo T, Shinozaki K, Yoshida S, and Nakashita H (2008) Plant Cell 20 (6): 1678-1692.). That is, it is conceived that the cutting treatment suppressed the salicylic acid-mediated resistance of the plant to enable gene introduction by the GV3101 strain.

GUS expression in ears subjected to the floral dip/cutting-sealing method was found only in *quinoa* at from 40 days to 50 days after seeding (Table 6). It has been revealed that, in floral dip experiments of *Arabidopsis*, transformed seeds are obtained only when infection treatment is performed 5 days or more before flowering, and hence a period in which gene introduction can be performed is limited (Desfeux C, Clough S J, and Bent A F (2000) Plant Physiology 123 (3): 895-904). This is considered to be because a cap structure formed on the stigma of an *Arabidopsis* female organ 3 days before flowering blocks the *Agrobacterium* from accessing an ovule (Smyth D R, Bowman J L, and Meyerowitz E M (1990) The Plant Cell 2:755-767). Also in floral dip experiments of *quinoa*, the gene introduction period was limited (Table 6), and hence it is conceived that *Arabidopsis* and *quinoa* are similar to each other in mode of gene introduction into the plant body.

Through use of a transformed callus formation ratio as an indicator, *quinoa* varieties and *Agrobacterium* strains suited for the transformation of *quinoa* were selected. As a result of the infection experiment on seedling sections of the Kd variety and seedling sections of the mutant ghy using the GV3101 strain, GUS expression was recognized in 6.98% of the calluses of the Kd variety and 6.78% of the calluses of the mutant ghy (FIGS. 32 and Table 14). In addition, spot-like GUS expression was recognized in all transformed calluses of the Kd variety. In the transformed calluses of the mutant ghy, spot-like GUS expression was recognized in one individual, and 2 $mm^2$ or more of GUS expression was recognized in three individuals. It is conceived that spot-like transient GUS expression is not transformed, and only the mutant ghy is transformed. The possibility was suggested that betalain pigments having antifungal activity and antibacterial activity (Polturak G, Grossman N, Vela-Corcia D, Dong Y, Nudel A, Pliner M, Levy M, Rogachev I, and Aharoni A (2017) Proceedings of the National Academy of Sciences of the United States of America 114 (34): 9062-9067; Canadanovic-Brunet J M, Savatovic S S, and Cetkovic G S (2011) Czech Journal of Food Sciences 29 (6): 575-585) act in an inhibitory manner in the transformation of the Kd variety. Both varieties show similar frequencies of gene expression (Table 14), and hence it is conceived that the betalains probably do not influence the access of the *Agrobacterium* to the plant body and gene introduction. In view of the foregoing, it is conceived that the betalain pigments influence the incorporation of T-DNA into the *quinoa* genome.

It was suggested that the betalain pigments acted in an inhibitory manner in the transformation of *quinoa*. Meanwhile, the 85 variety of *quinoa* showed the highest transformation efficiency in the transformation experiments with the GV3101 strain and the MAFF301276 strain (FIG. 17, FIG. 20, Table 9, and Table 10). Accordingly, it is conceived that the 85 variety is a *quinoa* variety useful for transformation with the *Agrobacterium*. The hypocotyl (at 5 days after seeding) of the 85 variety subjected to the transformed callus experiment shows a red color as with the Kd variety and the 108 variety. However, a mature ear of the 85 variety shows an orange color. There is a report that *quinoa* synthesizes phenolic compounds in different amounts depending on varieties (Tang Y, Li X, Zhang B, Chen P X, Liu R, and Tsao R6 (2015) Food Chemistry 166:380-388). Phenols generally have stress tolerance and antibacterial activity, but there is a report that a plurality of phenolic compounds including acetosyringone induce vir genes of the *Agrobacterium* (Bhattacharya A, Sood P, and Citovsky V (2010) Molecular Plant Pathology 11 (5): 705-719). Detailed functions of phenolic compounds synthesized by the 85 variety have not been elucidated, but it is conceivable that the 85 variety may contain such a substance as to activate vir genes of the GV3101 strain and the MAFF301276 strain.

When *quinoa* seedlings were inoculated with the MAFF301276 strain and the MAFF311303 strain, gene introduction was found near the shoot apex (FIG. 33). Those two bacterial strains belong to G1 in classification by genetic properties (genomovar). Bacterial strains belonging to this group are frequently isolated from galls formed in plants (Portier P, Saux M L, Mougel C, Lerondelle C, Chapulliot D, Thiouslouse J, and Nesme X (2006) Applied and Environmental Microbiology 72 (11): 7123-7131), and are predicted to have a wide host range. In particular, the MAFF301276 strain showed high transformation efficiency (85.6±1.1%) in the infection experiment on hypocotyl sections of the Kd variety (FIG. 14 and Table 8). In addition, in the infection experiment on hypocotyl sections of six varieties of *quinoa*, transformed calluses were formed in all the varieties tested (FIG. 20 and Table 10). Those results show that the MAFF301276 strain has a strong ability to infect *quinoa* and a wide host range. Jin et al. suggest that an increase in vir gene expression is involved in the pathogenicity of the *Agrobacterium* and the widening of its host range (Jin S G, Komari T, Gordon M P, and Nester E W (1987) Journal of Bacteriology 169 (10): 4417-4425). Accordingly, it was presumed that the vir genes on the Ti plasmid were involved in the excellent characteristics of the MAFF301276 strain. Gene introduction into the *quinoa* genome by the MAFF301276 strain was demonstrated by the results of genetic analysis using a next-generation sequencer and PCR analysis (FIG. 22). In addition, those analyses revealed that the pTi plasmid derived from the MAFF301276 strain and part of the binary vector pCAMBIA1301 were incorporated as a fusion (FIG. 22). It is unknown whether the fusion of two T-DNAs occurred in the bacterium, or occurred in the process of gene introduction into the host plant. However, it is conceivable that the fusion of T-DNAs may be involved in the excellent infection ability of the MAFF301276 strain.

Meanwhile, the MAFF311303 strain lacks the vir gene cluster indispensable for gene introduction, and is classified as nonpathogenic. It is interesting how the MAFF311303 strain classified as nonpathogenic introduces the GUS gene into plant cells. An action on the host plant side is also important for infection with the *Agrobacterium*, and acetosyringone secreted from a damage site of a plant is involved in the activation of vir genes (Bhattacharya A, Sood P, and Citovsky V (2010) Molecular Plant Pathology 11 (5): 705-719). In addition, it is known that the VIP1 protein of *Arabidopsis* is involved in T-DNA transfer into a host nucleus (Tzfira T, Vaidya M, and Citovsky V (2001) The EMBO Journal 20 (13): 3596-3607). However, the action on the host plant side in infection with the *Agrobacterium* has not been completely elucidated. Accordingly, it was presumed that the introduction of the GUS gene by the nonpathogenic MAFF311303 strain occurred as a result of a novel action on the plant side. In addition, in the infection experiment on hypocotyl sections of the Kd variety, the MAFF311303 strain was unable to form transformed calluses (FIG. 14 and Table 8), and hence it was presumed that the above-mentioned action occurs specifically to tissues near the shoot apex. The MAFF301276 strain and the MAFF311303 strain are wild-type strains, and there are few research reports thereon (Kouki Ota and Koushi Nishiyama (1984) Studies on the Crown Gall Diseases of Flower Crops. Occurrence of the Disease and the Characterization of the Causal Bacterium. The Journal of General Plant Pathology (Ann. Phytopath. Soc. Japan) 50:197-204). With remarkable progress of next-generation sequencer technology, it has now become possible to obtain unknown genomic information within a short period of time and easily. It is conceived that, through genomic analysis and RNA analysis of each bacterial strain, the excellent transforming ability of the MAFF301276 strain, and the mechanism of gene introduction by the MAFF311303 strain can be elucidated to contribute to the construction of a novel *Agrobacterium* strain having high transformation efficiency. In addition, such *Agrobacterium* strain is expected to be utilized as a potent gene introduction tool in plant species for which gene introduction with *Agrobacterium* is difficult.

With the production of transformed calluses with the MAFF301276 strain, the remaining challenge is to establish a redifferentiation system. In view of this, redifferentiation medium was investigated using the mutant ghy incapable of synthesizing betalain pigments conceived to influence redifferentiation. As a result, redifferentiation of adventitious roots, which had not been found investigation of redifferentiation of the Kd variety, was able to be recognized. In view of this, it is conceived that the betalain pigments are involved in the formation of roots. The possibility was suggested that the induction of redifferentiation of ghy calluses was enabled by investigating, for example, the period of callus induction, the kinds and concentrations of plant hormones in the redifferentiation medium, culture conditions, such as light and temperature, and tissues to be tested.

In the floral dip/cutting-sealing method using four varieties of *quinoa* and seven *Agrobacterium* strains, the MAFF301276 strain was found to cause GUS expression in ears of all the *quinoa* varieties tested irrespective of the presence or absence of the cutting-sealing treatment (FIG. 26). The results agree with the results of the transformed callus formation experiment (FIG. 20 and Table 10). Accordingly, it is conceived that the MAFF301276 strain has pathogenicity strong enough to overcome SAR irrespective of the variety of *quinoa*. Meanwhile, GUS gene introduction into female organs by the floral dip/cutting-sealing method was not found (FIG. 23). The bacterial strains found to cause GUS expression in female organs were MAFF212033, MAFF311303, and MAFF211729, which are conceived to be hypovirulent bacterial strains on the basis of the results of the gene introduction experiment by tissue culture and the floral dip method (FIG. 14, FIG. 26a, and Table 8). Those results suggest that there is no correlation between the strength of pathogenicity and the ability to approach a female organ.

Irrespective of the presence or absence of the cutting-sealing treatment, the GUS expression ratios in ears of the bladder cell-suppressed mutants (rebc and ghy/rebc) were high (FIG. 26). Accordingly, it was suggested that the mutant rebc and the mutant ghy/rebc were effective for gene introduction by the floral dip method. Bladder cells, which those two mutants lack, are present so as to cover the ear of quinoa (FIG. 2 to FIG. 5). Accordingly, it was presumed that the bladder cells serve as a physical barrier against the access of the Agrobacterium to a plant surface. This presumption was presumed to be elucidated by visualizing the behavior of the Agrobacterium through use of the GUS gene or green fluorescent protein (GFP).

Two Agrobacterium bacterial strains (MAFF301276 strain and MAFF311303 strain) selected by tissue culture and the floral dip/cutting-sealing method were used to produce the MAFF311303pTiMAFF301276ΔT-DNA strain. This bacterial strain was inoculated into the mutant ghy and the mutant ghy/rebc by the floral dip method (without cutting-sealing treatment), and as a result, female organ-specific GUS expression was found (FIG. 27 to FIG. 29). This result suggests that the MAFF311303 strain acquired strong pathogenicity of the MAFF301276 strain to overcome SAR, to thereby enable gene introduction into female organs. That is, when the MAFF311303pTiMAFF301276ΔT-DNA strain and quinoa mutants are used, a general-purpose floral dip method without cutting-sealing treatment can be applied to provide transformed seeds of quinoa. In addition, through application of ABA capable of suppressing SAR (Koga H, Dohia K, and Mori M (2004) Physiological and Molecular Plant Pathology 65 (1): 3-9; Yasuda M, Ishikawa A, Jikumaru Y, Seki M, Umezawa T, Asami T, Maruyama-Nakashita A, Kudo T, Shinozaki K, Yoshida S, and Nakashita H (2008) Plant Cell 20 (6): 1678-1692.), an increase in transformation efficiency was found for the mutant ghy/rebc (FIG. 30 and FIG. 31). Accordingly, the use of ABA may be effective for improving the efficiency of transformation of quinoa female organs by this technique. The final stage, namely the selection of seeds, has been arrived at.

The existence of quinoa mutants and a novel Agrobacterium strain is important for the novel method of transforming quinoa constructed in Examples of the present invention. However, when the analyses of betalain pigments synthesized by the 85 variety of quinoa, and of the excellent abilities of the MAFF301276 strain and the MAFF311303 strain to transform quinoa are advanced, a general-purpose quinoa transformation method can be expected to be established. In addition, the establishment of the method of transforming quinoa can be expected to further advance quinoa research, to thereby produce quinoa having novel characteristics. For example, quinoa contains plant toxins called saponins in its seeds, and quinoa cultivated in saline land has an increased saponin content in some cases (Norio Yamamoto (2014) Crops, Man, and Life in the Central Andes. Senri Ethnological Reports 117). In addition, quinoa has threshability, and hence mechanization for mass production is difficult (Yuji Fujikura, Akio Hongo, and Norio Yamamoto (2009) Domestication of Plants: Is quinoa a cultivated plant?—An Essay on Cultivation of Minor Grain from the Andes-. Senri Ethnological Reports 84:225-244). Accordingly, when those traits are deleted, excellent characteristics of quinoa can be sufficiently exhibited as a solution to a food crisis. The achievements of Examples of the present invention can contribute to the progress of quinoa research at the genetic level.

Besides, it was recognized that the gene introduced by the novel method of transforming quinoa constructed in Examples of the present invention was able to be inherited by progeny. That is, the novel method of transforming quinoa constructed in Examples of the present invention can provide a seed having introduced therein a gene of interest (seed expressing the function of the gene of interest).

TABLE 14

|  | Kd | ghy |
|---|---|---|
| Number of sections (sections) | 43 | 59 |
| gusA-expressing callus formation ratio (%) | 6.98 | 6.78 |
| Formation ratio of calluses exhibiting 2 $mm^2$ or more gusA expression (%) | 0 | 5.08 |

Results of infection experiment on Kd variety and ghy using GV3101 strain.

INDUSTRIAL APPLICABILITY

According to the present invention, the method of transforming quinoa was able to be provided.

The invention claimed is:

1. A method of producing a transformed plant, a seed of the plant, or a callus of the plant, the method comprising the following steps:
   - (1-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
   - (1-2) a step of cutting the plant body; and
   - (1-3) a step of placing the cut plant body including a site having introduced therein the gene of interest under high-humidity and dark conditions to obtain a plant body having introduced the gene of interest;

or
   - (2-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
   - (2-2) a step of cutting the plant body;
   - (2-3) a step of placing the cut plant body including a site having introduced therein the gene of interest under high-humidity and dark conditions; and
   - (2-4) a step of growing the plant body until a seed is ready to be harvested, to thereby obtain a seed having introduced therein the gene of interest;

or
   - (3-1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto;
   - (3-2) a step of placing the inoculated plant body under high-humidity and dark conditions;
   - (3-3) a step of cutting the plant body;
   - (3-4) a step of placing the cut plant body including a site having introduced therein the gene of interest under high-humidity and dark conditions; and
   - (3-5) a step of producing a callus from the plant body, and wherein the *Agrobacterium* is an *Agrobacterium* strain MAFF311303 transformed with the expression vector carrying a gene of interest under control of a promoter capable of inducing expression of the gene of interest in a plant body and with a Ti plasmid which is derived from an *Agrobacterium* strain MAFF301276, wherein a T-DNA region has been removed from the Ti plasmid.

2. The method according to claim 1, wherein the plant body is *quinoa*.

3. The method according to claim 1, further comprising a step of bringing abscisic acid into contact with the target plant body before the step (1-1) or the step (2-1), simultaneously with the step (1-1) or the step (2-1), or between the step (1-1) and the step (1-2) or between the step (2-1) and the step (2-2).

4. A method of producing a transformed plant, comprising the following step:
   - (1) a step of bringing an *Agrobacterium* strain MAFF311303 transformed with an expression vector carrying a gene of interest under control of a promoter capable of inducing expression of the gene of interest in a plant body and with a Ti plasmid which is derived from an *Agrobacterium* strain MAFF301276, wherein a T-DNA region has been removed from the Ti plasmid into contact with a target plant body to inoculate the *Agrobacterium* thereinto.

5. The method according to claim 4, further comprising a step of bringing abscisic acid into contact with the target plant body before the step (1), simultaneously with the step (1) or after the step (1).

6. A method of producing a seed of a transformed plant, comprising the following steps:
   - (1) a step of bringing an *Agrobacterium* transformed with an expression vector carrying a gene of interest under control of a promoter capable of inducing expression of the gene of interest in a plant body into contact with a target plant body to inoculate the *Agrobacterium* thereinto; and
   - (2) a step of growing the plant body until a seed is ready to be harvested, to thereby obtain a seed having introduced therein the gene of interest, and wherein the *Agrobacterium* is an *Agrobacterium* strain MAFF311303 transformed with the expression vector carrying a gene of interest under control of a promoter capable of inducing expression of the gene of interest in a plant body and with a Ti plasmid which is derived from an *Agrobacterium* strain MAFF301276, wherein a T-DNA region has been removed from the Ti plasmid.

7. The method according to claim 6, further comprising a step of bringing abscisic acid into contact with the target plant body before the step (1), simultaneously with the step (1) or after the step (1).

* * * * *

SEQUENCE LISTING

```
<160> NUMBER OF SEQ ID NOS: 15

<210> SEQ ID NO 1
<211> LENGTH: 25
<212> TYPE: DNA
<213> ORGANISM: Artificial Sequence
<220> FEATURE:
<223> OTHER INFORMATION: Set1 Forward primer

<400> SEQUENCE: 1
gtggatttgt tacaaatggg acccg                                         25

<210> SEQ ID NO 2
<211> LENGTH: 25
<212> TYPE: DNA
<213> ORGANISM: Artificial Sequence
<220> FEATURE:
<223> OTHER INFORMATION: Set1 Reverese primer
```

```
<400> SEQUENCE: 2
gtgcttgaga ggagaatgat agcga                                              25

<210> SEQ ID NO 3
<211> LENGTH: 25
<212> TYPE: DNA
<213> ORGANISM: Artificial Sequence
<220> FEATURE:
<223> OTHER INFORMATION: Set 2 Forward primer

<400> SEQUENCE: 3
gtggatttgt tacaaatggg acccg                                              25

<210> SEQ ID NO 4
<211> LENGTH: 25
<212> TYPE: DNA
<213> ORGANISM: Artificial Sequence
<220> FEATURE:
<223> OTHER INFORMATION: Set 2 Reverese primer

<400> SEQUENCE: 4
ccatacatga tcggagttgg acaag                                              25

<210> SEQ ID NO 5
<211> LENGTH: 25
<212> TYPE: DNA
<213> ORGANISM: Artificial Sequence
<220> FEATURE:
<223> OTHER INFORMATION: Set 3 Forward primer

<400> SEQUENCE: 5
tggggatcag ttttggatgg ttagg                                              25

<210> SEQ ID NO 6
<211> LENGTH: 25
<212> TYPE: DNA
<213> ORGANISM: Artificial Sequence
<220> FEATURE:
<223> OTHER INFORMATION: Set 3 Reverese primer

<400> SEQUENCE: 6
gtgcttgaga ggagaatgat agcga                                              25

<210> SEQ ID NO 7
<211> LENGTH: 28
<212> TYPE: DNA
<213> ORGANISM: Artificial Sequence
<220> FEATURE:
<223> OTHER INFORMATION: Set 4 Forward primer

<400> SEQUENCE: 7
gactgtcata catctcgaat tagtgact                                           28

<210> SEQ ID NO 8
<211> LENGTH: 25
<212> TYPE: DNA
<213> ORGANISM: Artificial Sequence
<220> FEATURE:
<223> OTHER INFORMATION: Set 4 Reverese primer

<400> SEQUENCE: 8
gtgcttgaga ggagaatgat agcga                                              25

<210> SEQ ID NO 9
<211> LENGTH: 28
```

```
<212> TYPE: DNA
<213> ORGANISM: Artificial Sequence
<220> FEATURE:
<223> OTHER INFORMATION: Set 5 Forward primer

<400> SEQUENCE: 9
gactgtcata catctcgaat tagtgact                                           28

<210> SEQ ID NO 10
<211> LENGTH: 25
<212> TYPE: DNA
<213> ORGANISM: Artificial Sequence
<220> FEATURE:
<223> OTHER INFORMATION: Set 5 Reverese primer

<400> SEQUENCE: 10
ccatacatga tcggagttgg acaag                                              25

<210> SEQ ID NO 11
<211> LENGTH: 25
<212> TYPE: DNA
<213> ORGANISM: Artificial Sequence
<220> FEATURE:
<223> OTHER INFORMATION: Set 6 Forward primer

<400> SEQUENCE: 11
tggggatcag ttttggatgg ttagg                                              25

<210> SEQ ID NO 12
<211> LENGTH: 25
<212> TYPE: DNA
<213> ORGANISM: Artificial Sequence
<220> FEATURE:
<223> OTHER INFORMATION: Set 6 Reverese primer

<400> SEQUENCE: 12
ccatacatga tcggagttgg acaag                                              25

<210> SEQ ID NO 13
<211> LENGTH: 2500
<212> TYPE: DNA
<213> ORGANISM: Chenopodium quinoa

<400> SEQUENCE: 13
tgctaaaatt taattcattc tacacatttt cctaaaatac gtagggtata ttcttggtta         60
aagtgtgtta ccataagttt aagggattac actaaccatg gtgattggtg ataggtga         120 agagacaaga aggtcatcaa ctacatagaa tattagttta aaattcaatg tgacatgata        180
agttgatttg acatttagct tgccattaga gatgttagtg aacttaatcc atacgtgtat        240
tttgaaatct actccgtagg aagtaaaagg gaaaagtaat tgtttagag gtgttaaatt         300 ctaaacctat tattagtcta aatatattta atgaagtttg agtaaaatct atgaataatt        360
aacatattca aatttgacac acatgtcaat atatgacttt atagatgtat aattaaatat        420
agtaaaaaaa taaaaagttg atattttaaa gctttatatt aatacctatt taacaatata        480
tttcttgata caattcattg ttaataattt attatagaac tatggtaata gttagtgtat        540
gaatattgaa aaaaaatcta agttcttgtt taattcacct tattttgtt gaactgaaat         600 tatttttca ttaaactgta attattttta ctgaactgaa ttttttttg gtgaactgaa          660 attattttg ttgaagtgaa attatttta ttgattctct attatatttc ttctttaaaa         720
ttaccgagtt ttacagtatt aaaattatat ttactggact aaaattattt tactgaagtg        780
```

```
aaattatttt accgaatatt attttttcaa ggtgaagtaa accgggtcta acatgtcatt    840
tattcgaaga cggagagagt atgatttgtt tccttcgata ccaaaaaatt gaaattgtgg    900
caagtacttc gtgcttcctc tttgttttaa taagtgttac acttcttttt ttggcaaaaa    960
gctacctttc ttttacaatt tttaaatact tcaactaccc cacttacctt attttattta    1020
agtcaattaa attgcctaaa actatgtgcc ggtcaaattg taacacttat taaaacacga    1080
agggagtata tggttattgt accggaaaga aagggttagt taaccaacct agtataatgc    1140
tactatagga gctgtaacca aatcatgcct tagcactgat acaatctagt ttggtaaatt    1200 aggttttta aaaggttcgg ttataggatc aagattgatg aaaacagaat tttcattaaa    1260 atgttttgg tgcaaatctc tctctgggat taacctgcat ctgtcacgtg caattatcct    1320
actgatgtac gagtaataat atttatcacc aatcccttat catctatcga gaatgttgtc    1380
cgtagcctgt tttgaacctt attatcagta ttcagtgtaa gttgatagac agctatgctg    1440
tttgttagca gtgacttttt atgttttca cccgtcattc ttctctattt cttcgatgca    1500
aatcctataa tttgccaatc gatgcaataa tttcttggta tatggtctta tatactgtta    1560
taggagtgct aaatgcttct atcagcagtg gtatggttcg ttttttgcta ttataaatgc    1620
tctccctaag cttgaatgac tgatggtctg ctgggcacag caacaactag aagcttgtca    1680
atgataagtt atgaatattt tattagtgat ttttggttat cgaggttaat gtactgaaaa    1740
actagctcaa ctggttcttt ttcgtgcgat ttcggttcat gaaaattcca taacaaattt    1800
tgggtaatag actcggaata cattttaat atggttttgc cctaactctg tgagactgtg    1860
atctagagat atgtatgttc aaattctgag ggtagaggat ctatagtagc ccctgaggtt    1920
tgcctgtatg attgcatctt actattgatt ctggatgact ctctggatct acattggata    1980
tcacgtgaat gagaagtttt gcttaaaatc tgagaggagt ttacatgcca tgctaaggtg    2040
cctaatgatc cacatcttaa ggttaatggt tgatgagcat gttgaactaa tgaactatcc    2100
atatcgttta gtcttagcca ttatgcagac acaattatgc tattttgata ggcagtggct    2160
cgtcatgtag gtccctagtg aggcctactg tgcaaaagcg aggaaaaccc catccctccg    2220
tttcctttgc catctccatg tcctcattag gaccacatat agggttttct ctctctttct    2280
acgtataata catgtacgag gtgtacccag actgccaatt tgaacaaat tccccccctc    2340 cccaacccat cctaaaatga aataaattac aaaggaaata gaaacaacat agctaagttt    2400
cgtgaaataa tgattgaaca aactctctgt cattgaataa atgcatggtt ttgcatgcat    2460 atatacccccc tagctcccaa aaacctagtt ccaacgccgc                        2500

<210> SEQ ID NO 14
<211> LENGTH: 1449
<212> TYPE: DNA
<213> ORGANISM: Chenopodium quinoa

<400> SEQUENCE: 14
atgcacgcac acacaaagat ttccctagtt cacatctcca ctcctgtttt ttctcttgcg     60
atggatcgcc agctcagtca caagaaaagc ctttcttgct tctttgatga agattttaca    120
gaagatcaat cacccagctt tcaacacctc tctaagcata accaaaattt tcttgctcgc    180
cttcatggca cccatttcta ccctgatacc tcaccgatga tgtctcaaag ccctgaatca    240
tcctggtctc cctctccttc gttaacccc tctcatcctt ctcttctcta ctgctgtatc    300
tcctctctcc gtcgtgatgg tgatatttat tctctcactg tattcggtga cctagtctta    360
actggttcaa gtagtcgtcg agtctatgca tggcagtcac ttgactgcca tgcaaagggt    420
```

```
tacatacaat ctagctccgg cgaagtccgg gccatgcaag tctatgatga catgctcttc      480
actgcacata aggatcataa aattaggata tggaacatga gaacttgcag tggtagcttt      540
agggctagaa aagtccttac cttaccttgt gctagccatt tcaagagttt catttgtagg      600
tctgttgtcc cacaccatag gttaactgct aataagccaa ttacaccaca acataggggat     660 attatctctt gcatggcttt ttactatgtt gaaagtattt tatacactgg ctcatttgat      720
aaaactatca aagcttggaa gttaagtgta agaagtgta tcgactcgtt tgtagctcat       780
ggtgaccaca tcaatgacat ggtggtcaac caacaaagtg gctacctttt tacttgttct      840
tcagatggaa cagtaaagat gtggttaagg gtttatggtg aacacagcca tgtccttatt     900
aaggtcttta gttttcatac ctaccctatt tatgccttgg ctttaggtgt gtcaccatca     960
caaaggagtt tcttgtattc cggatcttct gatggatgta taaatttctg ggtgcaagag     1020
atttctactc actacaatca cggtggagtc ttagaagggc atcagtttgc ggttctttgc    1080
ctagtgaccc tagataattt ggtgattagt gggtctgagg actcgacgat caggatttgg    1140
aggcgagaga agtaagatt tactcatgag tgtcttgctg ttttagaagg gcatagaggg    1200
cctgtgagat gcttggctgc ttctttgcag gacgagcttg taacgagttt cttggtttat   1260
agtgctagct tggatcagac atttaaggtg tggagagtaa agctcttgcg agaaatgaag   1320
aaatcccctg gccgccatag caatggagat gatgatacgg aagatacaaa ttctgcaggg   1380
tgtgagccta gccctgtgtt gtctccttca tgggttaaga agaagcttca atgtcgtagt   1440
cttaaatag                                                          1449

<210> SEQ ID NO 15
<211> LENGTH: 1140
<212> TYPE: DNA
<213> ORGANISM: Chenopodium quinoa

<400> SEQUENCE: 15
atgcacgcac acacaaagat ttccctagtt cacatctcca ctcctgtttt ttctcttgcg      60
atggatcgcc agctcagtca caagaaaagc cttttcttgct tctttgatga agattttaca    120
gaagatcaat cacccagctt tcaacacctc tctaagcata accaaaattt tcttgctcgc     180
cttcatggca cccatttcta ccctgatacc tcaccgatga gtgtctcaaag ccctgaatca    240 tcctggtctc cctctccttc gttaaccccc tctcatcctt ctcttctcta ctgctgtatc    300
tcctctctcc gtcgtgatgg tgatatttat tctctcactg tattcggtga cctagtctta   360
actggttcaa gtagtcgtcg agtctatgca tggcagtcac ttgactgcca tgcaaagggt    420
tacatacaat ctagctccgg cgaagtccgg gccatgcaag tctatgatga catgctcttc    480
actgcacata aggatcataa aattaggata tggaacatga gaacttgcag tggtagcttt    540
agggctagaa aagtccttac cttaccttgt gctagccatt tcaagagttt catttgtagg    600
tctgttgtcc cacaccatag gttaactgct aataagccaa ttacaccaca acataggggat   660 attatctctt gcatggcttt ttactatgtt gaaagtattt tatacactgg ctcatttgat    720
aaaactatca aagcttggaa gttaagtgta agaagtgta tcgactcgtt tgtagctcat     780
ggtgaccaca tcaatgacat ggtggtcaac caacaaagtg gctacctttt tacttgttct    840
tcagatggaa cagtaaagat gtggttaagg gtttatggtg aacacagcca tgtccttatt    900
aaggtcttta gttttcatac ctaccctatt tatgccttgg ctttaggtgt gtcaccatca    960
caaaggagtt tcttgtattc cggatcttct gatggatgta taaatttctg ggtgcaagag   1020
```

-continued

```
atttctactc actacaatca cggtggagtc ttagaagggc atcagtttgc ggttctttgc    1080
ctagtgaccc tagataattt ggtgattagt gggtctgagg actcgacgat caggatttag   1140
```